United States Patent
Adachi et al.

(10) Patent No.: US 11,283,026 B2
(45) Date of Patent: Mar. 22, 2022

(54) COMPOUND HAVING TETRAAZATRIPHENYLENE RING STRUCTURE, LIGHT-EMITTING MATERIAL, AND ORGANIC ELECTROLUMINESCENT DEVICE

(71) Applicants: Hodogaya Chemical Co., Ltd., Tokyo (JP); Kyushu University, National University Corporation, Fukuoka (JP)

(72) Inventors: Chihaya Adachi, Fukuoka (JP); Takuma Yasuda, Fukuoka (JP); Katsuyuki Shizu, Fukuoka (JP); Takehiro Takahashi, Tokyo (JP)

(73) Assignees: Hodogaya Chemical Co., Ltd., Tokyo (JP); Kyulux, Inc., Fukuoka (JP)

( * ) Notice: Subject to any disclaimer, the term of this patent is extended or adjusted under 35 U.S.C. 154(b) by 27 days.

(21) Appl. No.: 15/302,027

(22) PCT Filed: Apr. 15, 2015

(86) PCT No.: PCT/JP2015/002077
§ 371 (c)(1),
(2) Date: Oct. 5, 2016

(87) PCT Pub. No.: WO2015/159541
PCT Pub. Date: Oct. 22, 2015

(65) Prior Publication Data
US 2017/0125700 A1    May 4, 2017

(30) Foreign Application Priority Data

Apr. 18, 2014  (JP) .............................. JP2014-086315

(51) Int. Cl.
*H01L 51/00* (2006.01)
*C07D 471/14* (2006.01)
(Continued)

(52) U.S. Cl.
CPC ........ *H01L 51/0072* (2013.01); *C07D 401/14* (2013.01); *C07D 471/14* (2013.01);
(Continued)

(58) Field of Classification Search
CPC .... C09K 2211/1074; C09K 2211/1044; H01L 2251/5384
See application file for complete search history.

(56) References Cited

U.S. PATENT DOCUMENTS 6,713,781 B1 * 3/2004 Chen ................... H01L 51/0072
257/103
7,282,586 B1    10/2007 Yen et al.
(Continued)

FOREIGN PATENT DOCUMENTS

CN    102659790 B  *  2/2015
JP    2005-281136 A     10/2005
(Continued)

OTHER PUBLICATIONS

Huang et al., The contributions of molecular vibrations and higher triplet levels to the intersystem crossing mechanism in metal-free organic emitters., J. Mater. Chem. C., 2017 (5), 6269. (Year: 2017).*
(Continued)

*Primary Examiner* — Jennifer A Boyd
*Assistant Examiner* — Sean M DeGuire
(74) *Attorney, Agent, or Firm* — Locke Lord LLP; James E. Armstrong, IV; Nicholas J. DiCeglie, Jr.

(57) ABSTRACT

A compound that emits fluorescence and delayed fluorescence is provided as a material for an organic electroluminescent device of high efficiency, and an organic photoluminescent device and an organic electroluminescent device of high efficiency and high luminance are provided using this compound. The compound of general formula (1) hav-
(Continued)

ing a tetraazatriphenylene ring structure is used as a constituent material of at least one organic layer in an organic electroluminescent device that includes a pair of electrodes, and one or more organic layers sandwiched between the pair of electrodes.

[Chemical Formula 1]

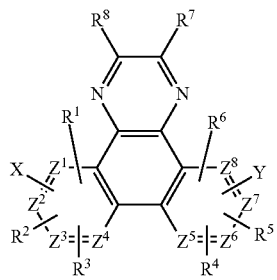

(1)

14 Claims, 3 Drawing Sheets

(51) Int. Cl.
*C07D 401/14* (2006.01)
*C09K 11/06* (2006.01)
*H01L 51/50* (2006.01)

(52) U.S. Cl.
CPC .......... *C09K 11/06* (2013.01); *H01L 51/0061* (2013.01); *H01L 51/0071* (2013.01); *C09K 2211/1044* (2013.01); *H01L 51/5012* (2013.01); *H01L 51/5072* (2013.01); *H01L 51/5096* (2013.01)

(56) References Cited

U.S. PATENT DOCUMENTS

2002/0074935 A1* 6/2002 Kwong ............... H01L 51/5024
  313/504
2012/0193619 A1 8/2012 Taka et al.

FOREIGN PATENT DOCUMENTS

| JP | 2005281136 A | * | 10/2005 |
|---|---|---|---|
| JP | 2005-330219 A | | 12/2005 |
| JP | 2005330219 A | * | 12/2005 |
| JP | 2006-135145 A | | 5/2006 |
| JP | 2006-351398 A | | 12/2006 |
| JP | 2007-189001 A | | 7/2007 |
| JP | 2007189001 A | * | 7/2007 |
| JP | 2014-009224 A | | 1/2014 |
| WO | 2011/046166 A1 | | 4/2011 |

OTHER PUBLICATIONS

International Search Report dated Jul. 21, 2015, issued for PCT/JP2015/002077.
Office Action issued in corresponding Japanese Patent Application No. JP 2019-154365, dated Sep. 23, 2020 (with English Translation).

* cited by examiner

COMPOUND HAVING TETRAAZATRIPHENYLENE RING STRUCTURE, LIGHT-EMITTING MATERIAL, AND ORGANIC ELECTROLUMINESCENT DEVICE

TECHNICAL FIELD

The present invention relates to compounds suitable for an organic electroluminescent device, which is a preferred self-emitting device for various display devices, and to such organic electroluminescent devices. Specifically, this invention relates to compounds having a tetraazatriphenylene ring structure, light-emitting materials formed of such compounds, and to organic electroluminescent devices using the compounds.

BACKGROUND ART

An organic electroluminescent device is a self-emitting device, and has been actively studied for their brighter, superior visibility, and the ability to display clearer images in comparison with liquid crystal devices.

In an attempt to improve the device luminous efficiency, there have been developed devices that use phosphorescent materials to generate phosphorescence, specifically that make use of the emission from a triplet excitation state. According to the excitation state theory, phosphorescent materials are expected to greatly improve luminous efficiency as much as about four times that of conventional fluorescence.

In 1993, M. A. Baldo et al. at Princeton University achieved 8% external quantum efficiency with a phosphorescent device using an iridium complex.

Devices that use light emission caused by thermally activated delayed fluorescence (TADF) have also been developed. In 2011, Adachi et al. at Kyushu University, National University Corporation achieved 5.3% external quantum efficiency with a device using a thermally activated delayed fluorescent material (refer to Non-Patent Document 1, for example).

In an organic electroluminescent device (hereinafter, referred to as "organic EL device"), carriers are injected from each of both electrodes, i.e., positive and negative electrodes to a light-emitting substance to generate a light-emitting substance in an excited state so as to emit light. It is generally said that in the case of a carrier injection type organic EL device, 25% of generated excitons are excited to an excited singlet state and the remaining 75% are excited to an excited triplet state. Accordingly, it is conceivable that utilization of light to be emitted from the excited triplet state, i.e., phosphorescence should provide higher energy use efficiency. However, in the phosphorescence, the excited triplet state has a long lifetime, and hence deactivation of energy occurs through saturation of an excited state and interactions with excitons in an excited triplet state, with the result that a high quantum yield is not obtained in many cases in general.

In view of the foregoing, an organic EL device utilizing a material which emits delayed fluorescence is conceivable. A certain kind of fluorescent substance emits fluorescence via intersystem crossing or the like leading to energy transition to an excited triplet state and the subsequent reverse intersystem crossing to an excited singlet state through triplet-triplet annihilation or thermal energy absorption. In the organic EL device, it is considered that the latter material which emits thermally activated delayed fluorescence is particularly useful. In this case, when a delayed fluorescent material is utilized in the organic EL device, excitons in an excited singlet state emit fluorescence as per normal. On the other hand, excitons in an excited triplet state absorb heat produced from a device and undergo intersystem crossing to an excited singlet to emit fluorescence. The fluorescence in this case is light emission from the excited singlet and hence is light emission at the same wavelength as fluorescence. However, the fluorescence has a longer lifetime of light to be emitted, i.e., a longer emission lifetime than those of normal fluorescence and phosphorescence by virtue of reverse intersystem crossing from an excited triplet state to an excited singlet state, and hence is observed as fluorescence delayed as compared to the normal fluorescence and phosphorescence. This can be defined as delayed fluorescence. Through the use of such thermally activated type exciton transfer mechanism, i.e., through thermal energy absorption after carrier injection, the ratio of a compound in an excited singlet state, which has usually been generated only at a ratio of 25%, can be increased to 25% or more. The use of a compound which emits intense fluorescence and delayed fluorescence even at a low temperature of less than 100° C. results in sufficient intersystem crossing from an excited triplet state to an excited singlet state by means of heat of a device, contributing to emission of delayed fluorescence. Thus, the luminous efficiency is drastically improved (refer to Patent Document 1 and Patent Document 2, for example).

Compounds of the following general formula (X) having a tetraazatriphenylene structure are proposed as electron transport material (refer to Patent Document 3, for example).

[Chemical Formula 1]

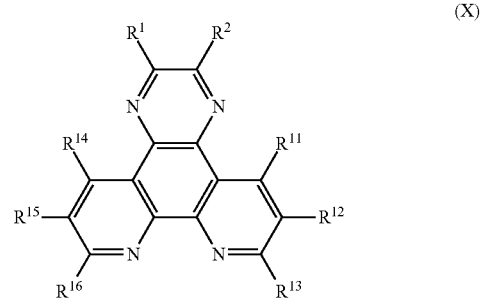

(X)

However, these compounds are not disclosed as material that emits light by itself, and the related art neither discloses nor indicates producing delayed fluorescence.

CITATION LIST

Patent Documents

Patent Document 1: JP-A-2004-241374
Patent Document 2: JP-A-2006-024830
Patent Document 3: JP-A-2005-281136

Non-Patent Documents

Non-Patent Document 1: Appl. Phys. Let., 98, 083302 (2011)
Non-Patent Document 2: Synth. Commun., 11, 513 (1981)
Non-Patent Document 3: Appl. Phys. Let., 101, 093306 (2012)
Non-Patent Document 4: Chem. Commun., 48, 11392 (2012)

Non-Patent Document 5: NATURE 492, 235 (2012)
Non-Patent Document 6: Organic EL Symposium, the 1st Regular presentation Preprints, 19 (2005)

SUMMARY OF THE INVENTION

Problems to be Solved by the Invention

An object of the present invention is to provide a compound that emits fluorescence and delayed fluorescence as a material for a high-efficiency organic EL device, and to provide an organic photoluminescent device (hereinafter, referred to as "organic PL device"), and an organic EL device of high efficiency and high luminance using this compound.

Means for Solving the Problems

To achieve the above object, the present inventors focused on compounds having a heterocyclic ring structure such as a carbazole ring, a phenoxazine ring, and an acridane ring, and/or a diarylamino group structure such as a diphenylamino group on a tetraazatriphenylene ring structure, and designed and chemically synthesized compounds using, as indexes, a difference between excited triplet energy and excited singlet energy ($\Delta E_{ST}$), and oscillator strength (f) which are obtained by theoretical calculation. As a result of actually measuring the emission (PL) spectrums of the chemically synthesized compounds, the present inventors found novel compounds having a tetraazatriphenylene ring structure which emit delayed fluorescence. The present inventors produced various test organic EL devices using these compounds, and the present invention was completed after thorough evaluations of device characteristics.

1) Specifically, the present invention is a compound of the following general formula (1) having a tetraazatriphenylene ring structure.

[Chemical Formula 2]

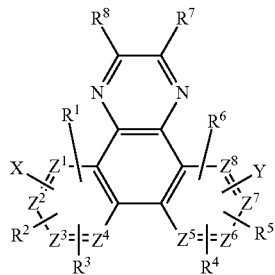

(1)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group, and Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group.

$R^1$ to $R^8$ may be the same or different from each other, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^8$ may bind to each other via a single bond, substituted or unsubstituted methylene, an oxygen atom, or a sulfur atom to form a ring.

$Z^1$ to $Z^8$ represent a carbon atom or a nitrogen atom, wherein at least one of $Z^1$ to $Z^4$ is a nitrogen atom, and at least one of $Z^5$ to $Z^8$ is a nitrogen atom, and in this case the nitrogen atoms do not have the hydrogen atoms or the substituents of $R^1$ to $R^6$.

2) The present invention is a compound having a tetraazatriphenylene ring structure according to 1). The compound is represented by the following general formula (1a).

[Chemical Formula 3]

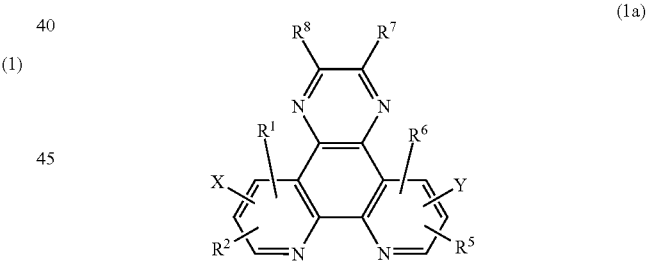

(1a)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group, and Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group.

$R^1$ to $R^2$, and $R^5$ to $R^8$ may be the same or different from each other, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^2$, and $R^5$ to $R^8$ may bind to each other via a single bond, substituted or unsubstituted methylene, an oxygen atom, or a sulfur atom to form a ring.

3) The present invention is a compound having a tetraazatriphenylene ring structure according to 1). The compound is represented by the following general formula (1a-1).

[Chemical Formula 4]

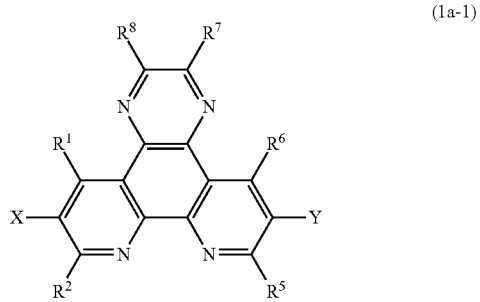

(1a-1)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group, and Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group.

$R^1$ to $R^2$, and $R^5$ to $R^8$ may be the same or different from each other, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^2$, and $R^5$ to $R^8$ may bind to each other via a single bond, substituted or unsubstituted methylene, an oxygen atom, or a sulfur atom to form a ring.

4) The present invention is a compound having a tetraazatriphenylene ring structure according to 1). The compound is represented by the following general formula (1a-2).

[Chemical Formula 5]

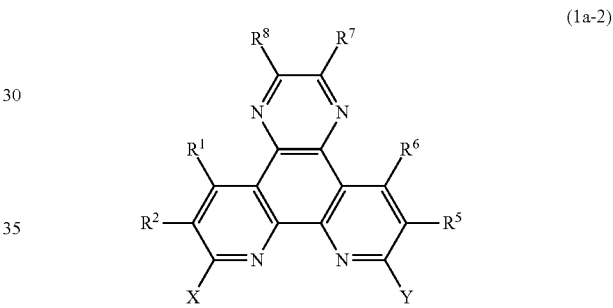

(1a-2)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group, and Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group.

$R^1$ to $R^2$, and $R^5$ to $R^8$ may be the same or different from each other, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^2$, and $R^5$ to $R^8$ may bind to each other via a single bond, substituted or unsubstituted methylene, an oxygen atom, or a sulfur atom to form a ring.

5) The present invention is a compound having a tetraazatriphenylene ring structure according to 1). The compound is represented by the following general formula (1a-3).

[Chemical Formula 6]

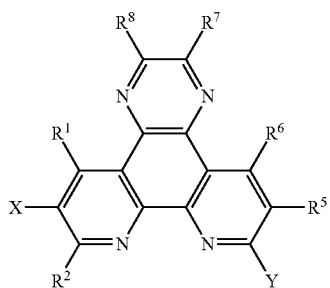

(1a-3)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group, and Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group.

$R^1$ to $R^2$, and $R^5$ to $R^8$ may be the same or different from each other, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^2$, and $R^5$ to $R^8$ may bind to each other via a single bond, substituted or unsubstituted methylene, an oxygen atom, or a sulfur atom to form a ring.

6) The present invention is a compound having a tetraazatriphenylene ring structure according to 1). The compound is represented by the following general formula (1a-4).

[Chemical Formula 7]

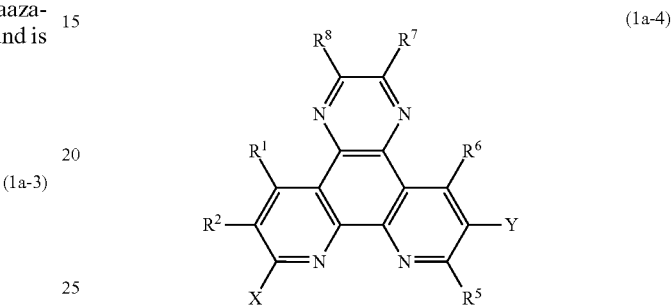

(1a-4)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group, and Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group.

$R^1$ to $R^2$, and $R^5$ to $R^8$ may be the same or different from each other, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^2$, and $R^5$ to $R^8$ may bind to each other via a single bond, substituted or unsubstituted methylene, an oxygen atom, or a sulfur atom to form a ring.

7) The present invention is a compound having a tetraazatriphenylene ring structure according to 1), wherein X and Y in the general formula (1) may be the same or different, and represent a group selected from substituted or unsubstituted carbazolyl, substituted or unsubstituted phenoxazinyl, substituted or unsubstituted phenothiazinyl, substituted or unsubstituted acridinyl, substituted or unsubstituted phenazinyl, and a disubstituted amino group substituted with an aromatic hydrocarbon group or a condensed polycyclic aromatic group.

8) The present invention is a light-emitting material including the compound having a tetraazatriphenylene ring structure according to 1).

9) The present invention is a light-emitting material according to 8) that emits thermally activated delayed fluorescence.

10) The present invention is an organic electroluminescent device that includes a pair of electrodes, and one or more organic layers sandwiched between the pair of electrodes, wherein the compound having a tetraazatriphenylene ring structure according to 1) is used as a constituent material of at least one organic layer.

11) The present invention is an organic electroluminescent device according to 10) in which the organic layer is a light emitting layer.

12) The present invention is an organic electroluminescent device according to 11) which emits delayed fluorescence.

13) The present invention is an organic electroluminescent device according to 10) in which the organic layer is an electron transport layer.

14) The present invention is an organic electroluminescent device according to 10) in which the organic layer is a hole blocking layer.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by X in general formula (1) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzoazepinyl, dibenzofuranyl, dibenzothienyl, naphthyridinyl, phenanthrolinyl, acridinyl, phenazinyl, phenoxazinyl, phenoselenazinyl, phenothiazinyl, phenotellurazinyl, phenophosphazinyl, and carbolinyl.

Specific examples of the "substituent" in the "substituted aromatic hydrocarbon group", the "substituted aromatic heterocyclic group", or the "substituted condensed polycyclic aromatic group" represented by X in general formula (1) include:

a deuterium atom, cyano, nitro;

halogen atoms such as a fluorine atom, a chlorine atom, a bromine atom, and an iodine atom;

linear or branched alkyl of 1 to 6 carbon atoms, such as methyl, ethyl, n-propyl, isopropyl, n-butyl, isobutyl, tert-butyl, n-pentyl, isopentyl, neopentyl, and n-hexyl;

linear or branched alkyloxy of 1 to 6 carbon atoms, such as methyloxy, ethyloxy, and propyloxy;

alkenyl such as vinyl, and allyl;

aryloxy such as phenyloxy, and tolyloxy;

arylalkyloxy such as benzyloxy, and phenethyloxy;

aromatic hydrocarbon groups or condensed polycyclic aromatic groups, such as phenyl, biphenylyl, terphenylyl, naphthyl, anthracenyl, phenanthrenyl, fluorenyl, indenyl, pyrenyl, perylenyl, fluoranthenyl, and triphenylenyl;

aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, phenoxazinyl, phenothiazinyl, carbolinyl, acridinyl, and phenazinyl;

arylvinyl such as styryl, and naphthylvinyl;

acyl such as acetyl, and benzoyl;

dialkylamino groups such as dimethylamino, and diethylamino;

disubstituted amino groups substituted with an aromatic hydrocarbon group or a condensed polycyclic aromatic group, such as diphenylamino, and dinaphthylamino;

diaralkylamino groups such as dibenzylamino, and diphenethylamino;

disubstituted amino groups substituted with an aromatic heterocyclic group, such as dipyridylamino, and dithienylamino;

dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl.

These substituents may be further substituted with the substituents exemplified above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" represented X in general formula (1) include the same groups exemplified for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by X in the general formula (1). These groups may have a substituent. Examples of the substituent include the same groups exemplified for the "substituent" in the "substituted aromatic hydrocarbon group", the "substituted aromatic heterocyclic group", or the "substituted condensed polycyclic aromatic group" represented by X in the general formula (1). The "substituent" may have the same forms exemplified above.

X in general formula (1) represents preferably a "substituted or unsubstituted aromatic heterocyclic group", a "substituted or unsubstituted condensed polycyclic aromatic group", or a "disubstituted amino group substituted with a group selected from an aromatic hydrocarbon group or a condensed polycyclic aromatic group", more preferably a "substituted or unsubstituted aromatic heterocyclic group" or a "disubstituted amino group substituted with an aromatic hydrocarbon group", particularly preferably carbazolyl, phenoxazinyl, phenothiazinyl, acridinyl, phenazinyl, or diphenylamino. Preferred as acridinyl and phenazinyl are 9,9-dimethyl-9,10-dihydroacridinyl, and 10-phenylphenazinyl.

The substituents of these groups are preferably carbazolyl, and a disubstituted amino group substituted with an aromatic hydrocarbon group, more preferably carbazolyl, and diphenylamino.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by Y in general formula (1) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by Y in general formula (1) include:

a deuterium atom, cyano, nitro;

halogen atoms such as a fluorine atom, a chlorine atom, a bromine atom, and an iodine atom;

linear or branched alkyloxy of 1 to 6 carbon atoms, such as methyloxy, ethyloxy, and propyloxy;

alkenyl such as vinyl, and allyl;

aryloxy such as phenyloxy, and tolyloxy;

arylalkyloxy such as benzyloxy, and phenethyloxy;

aromatic hydrocarbon groups or condensed polycyclic aromatic groups, such as phenyl, biphenylyl, terphenylyl, naphthyl, anthracenyl, phenanthrenyl, fluorenyl, indenyl, pyrenyl, perylenyl, fluoranthenyl, and triphenylenyl; and aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, phenoxazinyl, phenothiazinyl, carbolinyl, acridinyl, and phenazinyl.

These substituents may be further substituted with the substituents exemplified above. These substituents may bind to each other via a single bond, substituted or unsubstituted methylene, an oxygen atom, or a sulfur atom to form a ring.

Specific examples of the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by Y in general formula (1) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

Specific examples of the "substituent" in the "linear or branched alkyloxy of 1 to 6 carbon atoms having a substituent", or the "cycloalkyloxy of 5 to 10 carbon atoms having a substituent" represented by Y in general formula (1) include:

a deuterium atom, cyano, nitro;

halogen atoms such as a fluorine atom, a chlorine atom, a bromine atom, and an iodine atom;

linear or branched alkyloxy of 1 to 6 carbon atoms, such as methyloxy, ethyloxy, and propyloxy;

alkenyl such as vinyl, and allyl;

aryloxy such as phenyloxy, and tolyloxy;

arylalkyloxy such as benzyloxy, and phenethyloxy;

aromatic hydrocarbon groups or condensed polycyclic aromatic groups, such as phenyl, biphenylyl, terphenylyl, naphthyl, anthracenyl, phenanthrenyl, fluorenyl, indenyl, pyrenyl, perylenyl, fluoranthenyl, and triphenylenyl; and aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, phenoxazinyl, phenothiazinyl, carbolinyl, acridinyl, and phenazinyl.

These substituents may be further substituted with the substituents exemplified above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by Y in general formula (1) include the same groups exemplified for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by X in the general formula (1). These groups may have a substituent. Examples of the substituent include the same groups exemplified for the "substituent" in the "substituted aromatic hydrocarbon group", the "substituted aromatic heterocyclic group", or the "substituted condensed polycyclic aromatic group" represented by X in the general formula (1). The "substituent" may have the same forms exemplified above.

Specific examples of the "aryloxy" in the "substituted or unsubstituted aryloxy" represented by Y in general formula (1) include phenyloxy, biphenylyloxy, terphenylyloxy, naphthyloxy, anthracenyloxy, phenanthrenyloxy, fluorenyloxy, indenyloxy, pyrenyloxy, and perylenyloxy.

Specific examples of the "substituent" in the "substituted aryloxy" represented by Y in general formula (1) include:

a deuterium atom, trifluoromethyl, cyano, nitro;

halogen atoms such as a fluorine atom, a chlorine atom, a bromine atom, and an iodine atom;

linear or branched alkyl of 1 to 6 carbon atoms, such as methyl, ethyl, n-propyl, isopropyl, n-butyl, isobutyl, tert-butyl, n-pentyl, isopentyl, neopentyl, and n-hexyl;

linear or branched alkyloxy of 1 to 6 carbon atoms, such as methyloxy, ethyloxy, and propyloxy;

alkenyl such as vinyl, and allyl;

aralkyl such as benzyl, naphthylmethyl, and phenethyl;

aryloxy such as phenyloxy, and tolyloxy;

arylalkyloxy such as benzyloxy, and phenethyloxy;

aromatic hydrocarbon groups or condensed polycyclic aromatic groups, such as phenyl, biphenylyl, terphenylyl, naphthyl, anthracenyl, phenanthrenyl, fluorenyl, indenyl, pyrenyl, perylenyl, fluoranthenyl, and triphenylenyl;

aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, phenoxazinyl, phenothiazinyl, carbolinyl, acridinyl, and phenazinyl;

arylvinyl such as styryl, and naphthylvinyl;

acyl such as acetyl, and benzoyl;

dialkylamino groups such as dimethylamino, and diethylamino;

disubstituted amino groups substituted with an aromatic hydrocarbon group or a condensed polycyclic aromatic group, such as diphenylamino, and dinaphthylamino;

diaralkylamino groups such as dibenzylamino, and diphenethylamino;

disubstituted amino groups substituted with an aromatic heterocyclic group, such as dipyridylamino, and dithienylamino;

dialkenylamino group such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with the substituents exemplified above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" represented by Yin general formula (1) include the same groups exemplified for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by X in the general formula (1). These groups may have a substituent. Examples of the substituent include the same groups exemplified for the "substituent" in the "substituted aromatic hydrocarbon group", the "substituted aromatic heterocyclic group", or the "substituted condensed polycyclic aromatic group" represented by X in the general formula (1). The "substituent" may have the same forms exemplified above.

Y in general formula (1) represents preferably a "substituted or unsubstituted aromatic heterocyclic group", or a "substituted or unsubstituted condensed polycyclic aromatic group", more preferably a "substituted or unsubstituted aromatic heterocyclic group", particularly preferably phenoxazinyl, phenothiazinyl, acridinyl, phenazinyl, or carbazolyl in which a disubstituted amino group substituted with an aromatic hydrocarbon group or a condensed polycyclic aromatic group is present as a substituent. Preferred as acridinyl and phenazinyl are 9,9-dimethyl-9,10-dihydroacridinyl, and 10-phenylphenazinyl.

The substituents of these groups are preferably carbazolyl, and a disubstituted amino group substituted with an aromatic hydrocarbon group, more preferably carbazolyl, and diphenylamino.

Specific examples of the "linear or branched alkyl of 1 to 6 carbon atoms", the "cycloalkyl of 5 to 10 carbon atoms" or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R^1$ to $R^8$ in general formula (1) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R^1$ to $R^8$ in general formula (1) include:

a deuterium atom, cyano, nitro;

halogen atoms such as a fluorine atom, a chlorine atom, a bromine atom, and an iodine atom;

linear or branched alkyloxy of 1 to 6 carbon atoms, such as methyloxy, ethyloxy, and propyloxy;

alkenyl such as vinyl, and allyl;

aryloxy such as phenyloxy, and tolyloxy;

arylalkyloxy such as benzyloxy, and phenethyloxy;

aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; and aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, phenoxazinyl, phenothiazinyl, carbolinyl, acridinyl, and phenazinyl.

These substituents may be further substituted with the substituents exemplified above. These substituents may bind to each other via a single bond, substituted or unsubstituted methylene, an oxygen atom, or a sulfur atom to form a ring.

Specific examples of the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $R^1$ to $R^8$ in general formula (1) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

Specific examples of the "substituent" in the "linear or branched alkyloxy of 1 to 6 carbon atoms having a substituent", or the "cycloalkyloxy of 5 to 10 carbon atoms having a substituent" represented by $R^1$ to $R^8$ in general formula (1) include:

a deuterium atom, cyano, nitro;

halogen atoms such as a fluorine atom, a chlorine atom, a bromine atom, and an iodine atom;

linear or branched alkyloxy of 1 to 6 carbon atoms, such as methyloxy, ethyloxy, and propyloxy;

alkenyl such as vinyl, and allyl;

aryloxy such as phenyloxy, and tolyloxy;

arylalkyloxy such as benzyloxy, and phenethyloxy;

aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; and aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, phenoxazinyl, phenothiazinyl, carbolinyl, acridinyl, and phenazinyl.

These substituents may be further substituted with the substituents exemplified above. These substituents may bind to each other via a single bond, substituted or unsubstituted methylene, an oxygen atom, or a sulfur atom to form a ring.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R^1$ to $R^8$ in general formula (1) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, furyl, pyrrolyl, thienyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, phenoxazinyl, phenothiazinyl, and carbolinyl. These may bind to each other via a single bond, substituted or unsubstituted methylene, an oxygen atom, or a sulfur atom to form a ring.

Specific examples of the "substituent" in the "substituted aromatic hydrocarbon group", the "substituted aromatic heterocyclic group", or the "substituted condensed polycyclic aromatic group" represented by $R^1$ to $R^8$ in general formula (1) include:

a deuterium atom, trifluoromethyl, cyano, nitro;

halogen atoms such as a fluorine atom, a chlorine atom, a bromine atom, and an iodine atom;

linear or branched alkyl of 1 to 6 carbon atoms, such as methyl, ethyl, n-propyl, isopropyl, n-butyl, isobutyl, tert-butyl, n-pentyl, isopentyl, neopentyl, and n-hexyl;

linear or branched alkyloxy of 1 to 6 carbon atoms, such as methyloxy, ethyloxy, and propyloxy;

alkenyl such as vinyl, and allyl;

aralkyl such as benzyl, naphthylmethyl, and phenethyl;

aryloxy such as phenyloxy, and tolyloxy;

arylalkyloxy such as benzyloxy, and phenethyloxy;

aromatic hydrocarbon groups or condensed polycyclic aromatic groups, such as phenyl, biphenylyl, terphenylyl, naphthyl, anthracenyl, phenanthrenyl, fluorenyl, indenyl, pyrenyl, perylenyl, fluoranthenyl, and triphenylenyl;

aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, phenoxazinyl, phenothiazinyl, carbolinyl, acridinyl, and phenazinyl;

arylvinyl such as styryl, and naphthylvinyl;

acyl such as acetyl, and benzoyl;

dialkylamino groups such as dimethylamino, and diethylamino;

disubstituted amino groups substituted with an aromatic hydrocarbon group or a condensed polycyclic aromatic group, such as diphenylamino, and dinaphthylamino;

diaralkylamino groups such as dibenzylamino, and diphenethylamino;

disubstituted amino groups substituted with an aromatic heterocyclic group, such as dipyridylamino, and dithienylamino;

dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with the substituents exemplified above. These substituents may bind to each other via a single bond, substituted or unsubstituted methylene, an oxygen atom, or a sulfur atom to form a ring.

Specific examples of the "aryloxy" in the "substituted or unsubstituted aryloxy" represented by $R^1$ to $R^8$ in general formula (1) include phenyloxy, biphenylyloxy, terphenylyloxy, naphthyloxy, anthracenyloxy, phenanthrenyloxy, fluorenyloxy, indenyloxy, pyrenyloxy, and perylenyloxy. These may bind to each other via a single bond, substituted or unsubstituted methylene, an oxygen atom, or a sulfur atom to form a ring.

Specific examples of the "substituent" in the "substituted aryloxy" represented by $R^1$ to $R^8$ in general formula (1) include:

a deuterium atom, trifluoromethyl, cyano, nitro;

halogen atoms such as a fluorine atom, a chlorine atom, a bromine atom, and an iodine atom;

linear or branched alkyl of 1 to 6 carbon atoms, such as methyl, ethyl, n-propyl, isopropyl, n-butyl, isobutyl, tert-butyl, n-pentyl, isopentyl, neopentyl, and n-hexyl;

linear or branched alkyloxy of 1 to 6 carbon atoms, such as methyloxy, ethyloxy, and propyloxy;

alkenyl such as vinyl, and allyl;

aralkyl such as benzyl, naphthylmethyl, and phenethyl;

aryloxy such as phenyloxy, and tolyloxy;

arylalkyloxy such as benzyloxy, and phenethyloxy;

aromatic hydrocarbon groups or condensed polycyclic aromatic groups, such as phenyl, biphenylyl, terphenylyl, naphthyl, anthracenyl, phenanthrenyl, fluorenyl, indenyl, pyrenyl, perylenyl, fluoranthenyl, and triphenylenyl;

aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, phenoxazinyl, phenothiazinyl, carbolinyl, acridinyl, and phenazinyl;

arylvinyl such as styryl, and naphthylvinyl;

acyl such as acetyl, and benzoyl;

dialkylamino groups such as dimethylamino, and diethylamino;

disubstituted amino groups substituted with an aromatic hydrocarbon group or a condensed polycyclic aromatic group, such as diphenylamino, and dinaphthylamino;

diaralkylamino groups such as dibenzylamino, and diphenethylamino;

disubstituted amino groups substituted with an aromatic heterocyclic group, such as dipyridylamino, and dithienylamino;

dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with the substituents exemplified above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" represented by $R^1$ to $R^8$ in general formula (1) include the same groups exemplified for the "aromatic hydrocarbon group", the "aromatic heterocyclic group", or the "condensed polycyclic aromatic group"

in the "substituted or unsubstituted aromatic hydrocarbon group", the "substituted or unsubstituted aromatic heterocyclic group", or the "substituted or unsubstituted condensed polycyclic aromatic group" represented by X in the general formula (1). These groups may have a substituent. Examples of the substituent include the same groups exemplified for the "substituent" in the "substituted aromatic hydrocarbon group", the "substituted aromatic heterocyclic group", or the "substituted condensed polycyclic aromatic group" represented by X in the general formula (1). The "substituent" may have the same forms exemplified above.

In general formula (1) of the present invention, $Z^1$ to $Z^8$ represent a carbon atom or a nitrogen atom.

Any one to three of $Z^1$ to $Z^4$ are nitrogen atoms, and any one to four of $Z^5$ to $Z^8$ are nitrogen atoms.

In this case, when any one of $Z^1$ to $Z^4$ is a nitrogen atom, the hydrogen atom or the substituent of $R^3$ does not exist. When any two of $Z^1$ to $Z^4$ are nitrogen atoms, the hydrogen atoms or the substituents of $R^2$ and $R^3$ do not exist. When any three of $Z^1$ to $Z^4$ are nitrogen atoms, the hydrogen atoms or the substituents of $R^1$, $R^2$, and $R^3$ do not exist.

Similarly, when any one of $Z^5$ to $Z^8$ is a nitrogen atom, the hydrogen atom or the substituent of $R^4$ does not exist. When any two of $Z^5$ to $Z^8$ are nitrogen atoms, the hydrogen atoms or the substituents of $R^4$ and $R^5$ do not exist. When any three of $Z^5$ to $Z^8$ are nitrogen atoms, the hydrogen atoms or the substituents of $R^4$, $R^5$, and $R^6$ do not exist. When any four of $Z^5$ to $Z^8$ are nitrogen atoms, the hydrogen atoms or the substituents of $R^4$, $R^5$, $R^6$, and Y do not exist.

In general formula (1) of the present invention, it is preferable that any one of $Z^1$ to $Z^4$ is a nitrogen atom, and any one of $Z^5$ to $Z^8$ is a nitrogen atom. More preferably, $Z^4$ and $Z^5$ are nitrogen atoms.

The compounds of the general formula (1) having a tetraazatriphenylene ring structure of the present invention can emit delayed fluorescence and have a stable thin-film state as well as high luminous efficiency because of a small difference between excited triplet energy and excited singlet energy ($\Delta E_{ST}$), and a comparatively high oscillator strength (f) which are obtained by theoretical calculation.

The compounds of the general formula (1) having a tetraazatriphenylene ring structure of the present invention can be used as a constituent material of the light emitting layer of an organic EL device. With the use of the compounds of the present invention that emit delayed fluorescence, the luminous efficiency dramatically improves.

The compounds of the general formula (1) having a tetraazatriphenylene ring structure of the present invention can be used as a constituent material of the electron transport layer of an organic EL device. By using the material having higher rates of electron injection and mobility than conventional materials, the electron transport efficiency from the electron transport layer to the light emitting layer improves. This improves the luminous efficiency, and lowers the driving voltage, and thereby improves the durability of the organic EL device.

The compounds of the general formula (1) having a tetraazatriphenylene ring structure of the present invention can also be used as a constituent material of the hole blocking layer of an organic EL device. By using the material having an excellent hole blocking ability and superior electron transportability and higher stability in the thin-film state than conventional materials, it is possible to lower the driving voltage and improve the current resistance while maintaining high luminous efficiency, thereby improving the maximum emission luminance of the organic EL device.

Effects of the Invention

The compounds of the general formula (1) having a tetraazatriphenylene ring structure of the present invention are useful as a light-emitting material (a dopant compound) of the light emitting layer of an organic EL device, or as a constituent material of the electron transport layer or the hole blocking layer of an organic EL device. The compounds can emit delayed fluorescence, and have a stable thin-film state with excellent heat resistance. An organic EL device produced by using the compounds can have high efficiency, high luminance, and low driving voltage.

MODE FOR CARRYING OUT THE INVENTION

Figure 1:
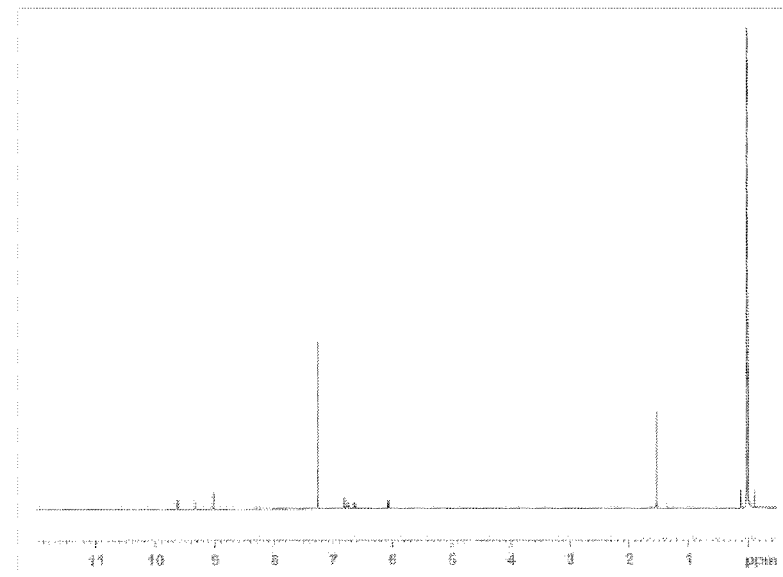
FIG. 1 is a $^1$H-NMR chart of the compound of Example 1 of the present invention (Compound 1).

The compounds of general formula (1) having a tetraazatriphenylene ring structure of the present invention can be synthesized, for example, as follows. First, a bromo group is introduced to 1,10-phenanthroline through bromination with bromine, N-bromosuccinimide, or the like, and the resulting compound is reacted with potassium bromide and a mixture of sulfuric acid and nitric acid to synthesize 1,10-phenanthroline-5,6-dione having a bromo group. After a further reaction with ethylenediamine, a tetraazatriphenylene derivative having a bromo group is synthesized. The compound having a tetraazatriphenylene ring structure of the present invention can then be synthesized through a condensation reaction, for example, a Buchwald-Hartwig reaction between the tetraazatriphenylene derivative having a bromo group and an amine such as a nitrogen-containing heterocyclic ring, or through a cross-coupling reaction, for example, Suzuki coupling, with a borate ester compound synthesized from a corresponding halogenated aryl (refer to Non-Patent Document 2, for example).

The compound having a tetraazatriphenylene ring structure of the present invention also can be synthesized as follows. First, tetraazatriphenylene is synthesized through reaction of 1,10-phenanthroline-5,6-dione with ethylenediamine, and the product is brominated with a compound such as N-bromosuccinimide to synthesize a tetraazatriphenylene derivative having a bromo group. The reaction product is then subjected to a cross-coupling reaction such as Suzuki coupling, or a condensation reaction such as the Buchwald-Hartwig reaction, as above.

Bromo-substituted compounds having different substitution positions can be obtained by using different bromination reagents, or by performing the reaction under different conditions.

The starting material 1,10-phenanthroline may be replaced with a homolog of 1,10-phenanthroline, specifically, an isomer having nitrogen atoms at different positions of the phenanthroline ring. In this case, the compound having a tetraazatriphenylene ring structure of the present invention can be synthesized as a compound having nitrogen atoms at different positions of the tetraazatriphenylene ring.

The following presents specific examples of preferred compounds among the compounds of general formula (1) having a tetraazatriphenylene ring structure. The present invention, however, is not restricted to these compounds.

[Chemical Formula 8]

(Compound 1)

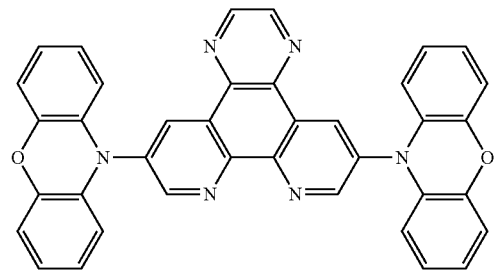

[Chemical Formula 9]

(Compound 2)

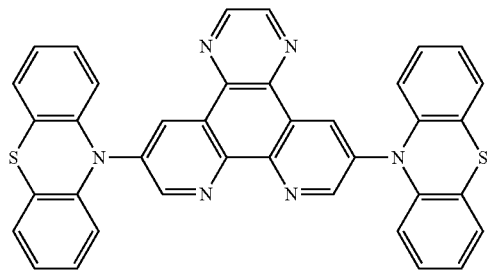

[Chemical Formula 10]

(Compound 3)

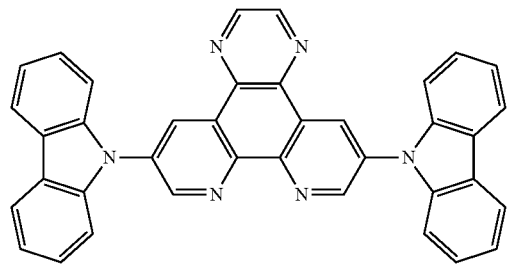

[Chemical Formula 11]

(Compound 4)

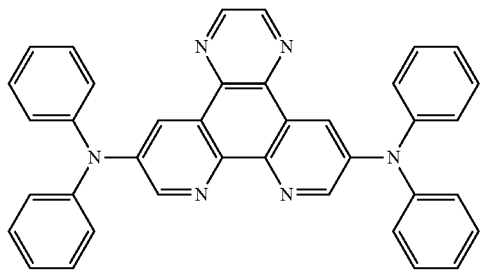

[Chemical Formula 12]

(Compound 5)

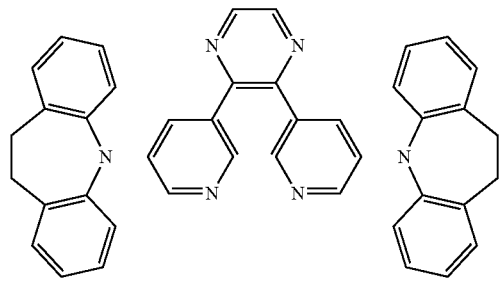

[Chemical Formula 13]

(Compound 6)

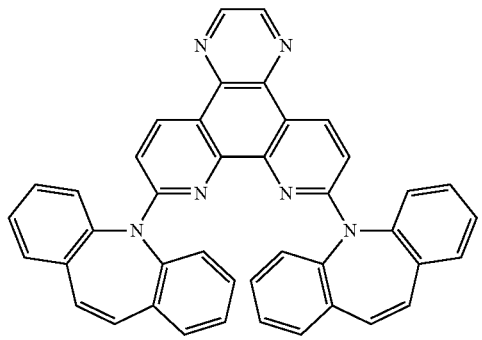

[Chemical Formula 14]
(Compound 7)
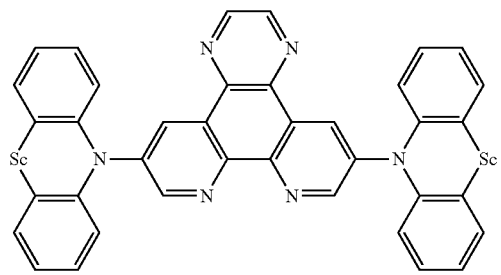
[Chemical Formula 15]
(Compound 8)
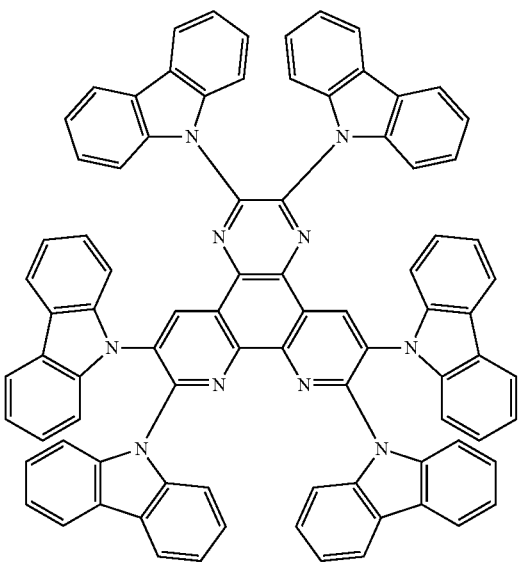
[Chemical Formula 16]
(Compound 9)
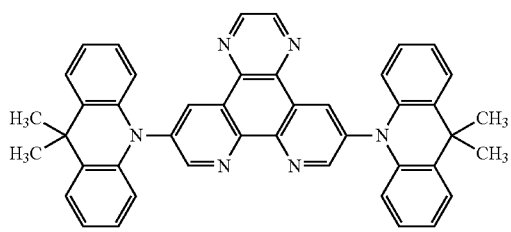
[Chemical Formula 17]
(Compound 10)
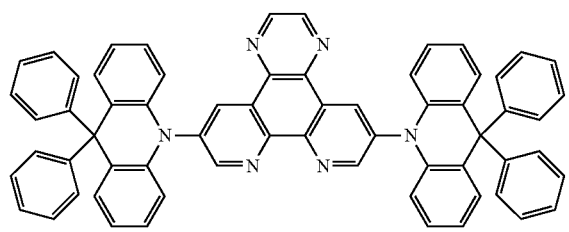
[Chemical Formula 18]
(Compound 11)
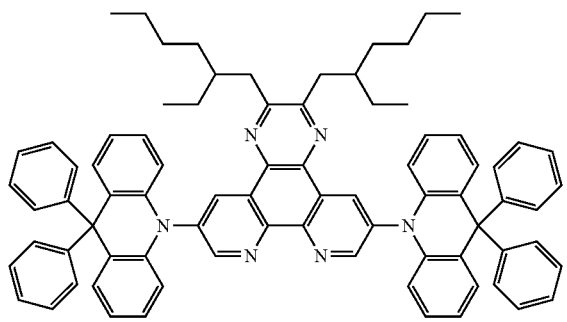
[Chemical Formula 19]
(Compound 12)
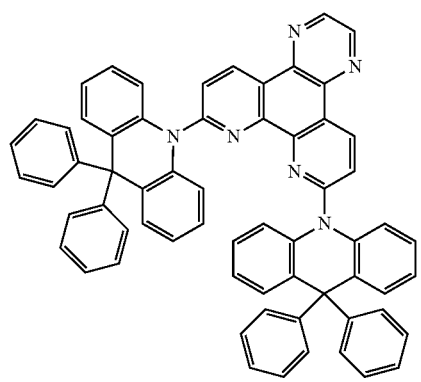

[Chemical Formula 20]
(Compound 13)
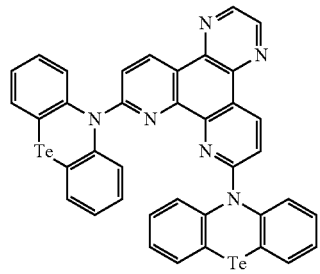
[Chemical Formula 21]
(Compound 14)
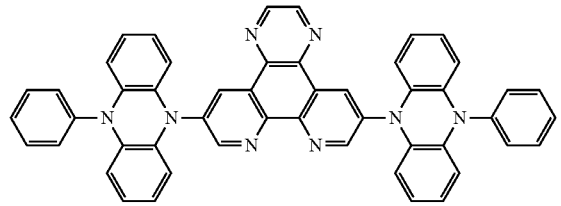
[Chemical Formula 22]
(Compound 15)
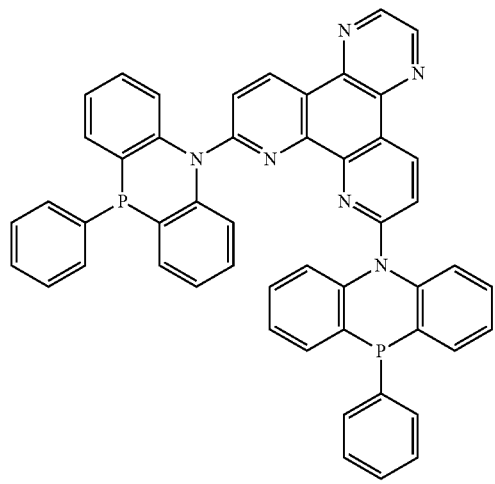
[Chemical Formula 23]
(Compound 16)
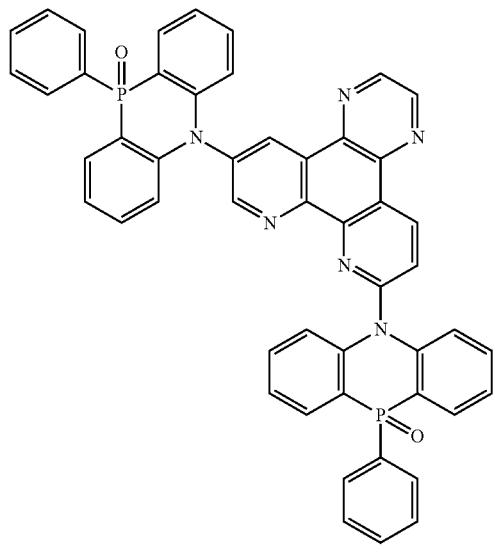
[Chemical Formula 24]
(Compound 17)
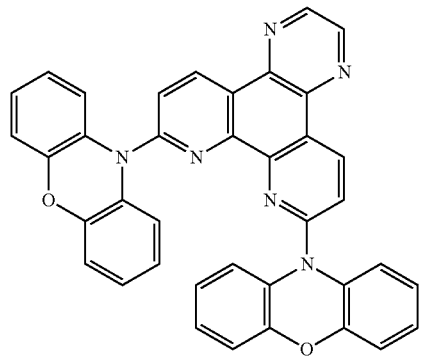
[Chemical Formula 25]
(Compound 18)
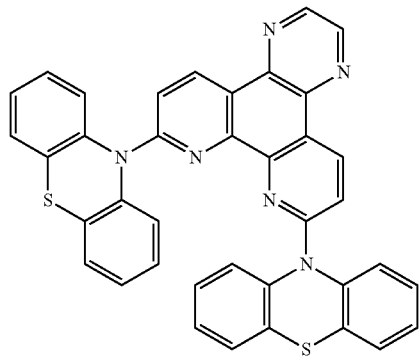

[Chemical Formula 26]
(Compound 19)
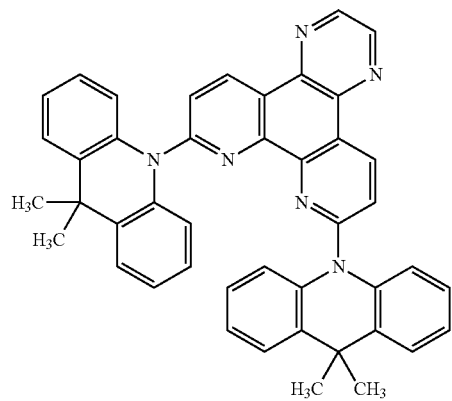
[Chemical Formula 27]
(Compound 20)
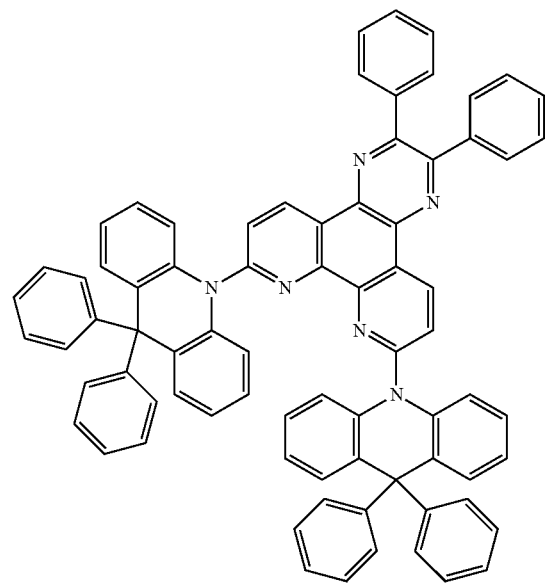
[Chemical Formula 28]
(Compound 21)
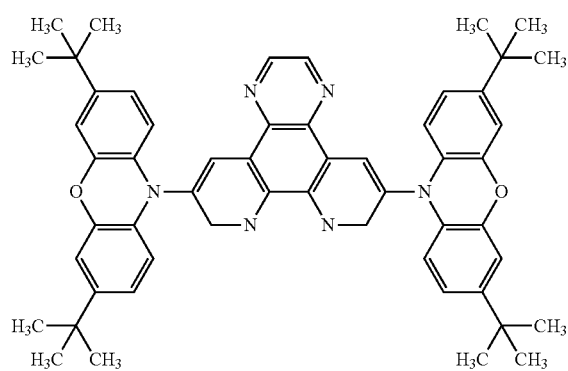
[Chemical Formula 29]
(Compound 22)
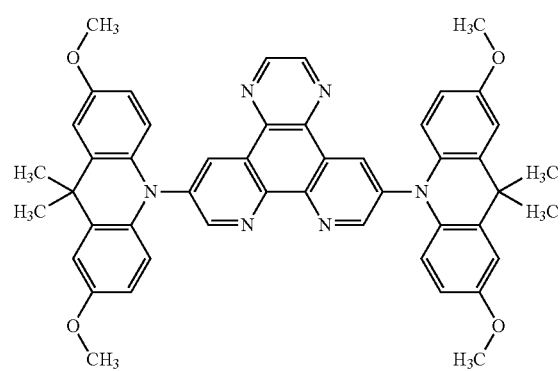
[Chemical Formula 30]
(Compound 23)
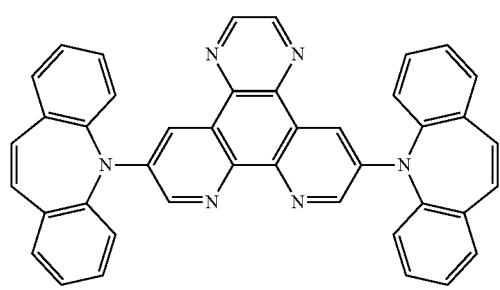
[Chemical Formula 31]
(Compound 24)
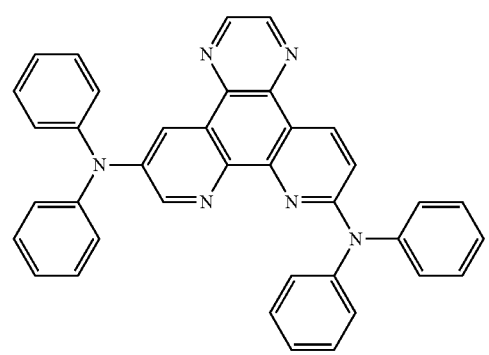

-continued
[Chemical Formula 32]
(Compound 25)
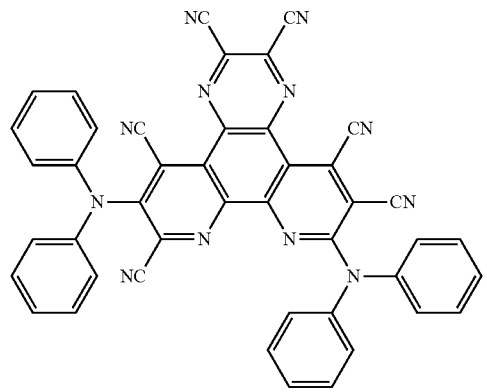
[Chemical Formula 33]
(Compound 26)
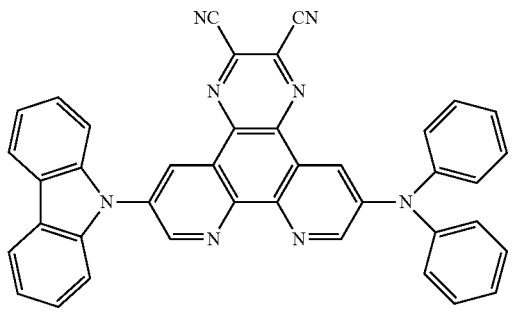
[Chemical Formula 34]
(Compound 27)
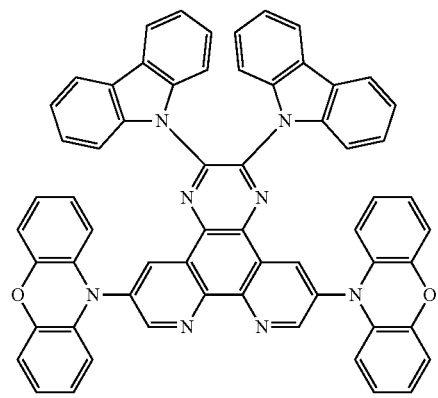
[Chemical Formula 35]
(Compound 28)
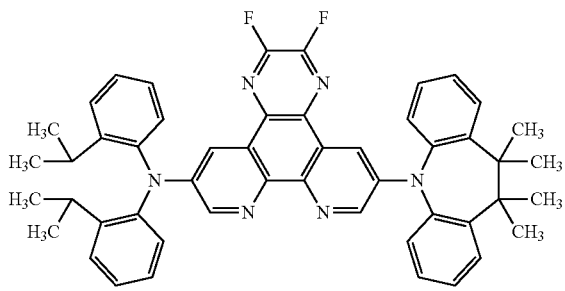
[Chemical Formula 36]
(Compound 29)
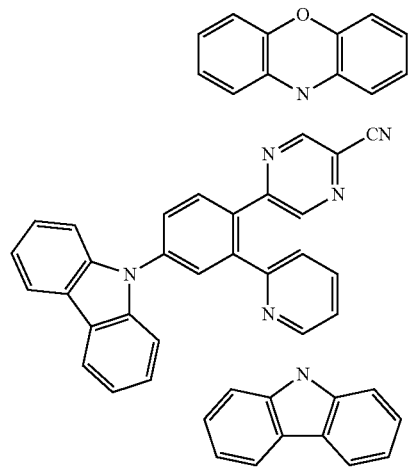
[Chemical Formula 37]
(Compound 30)
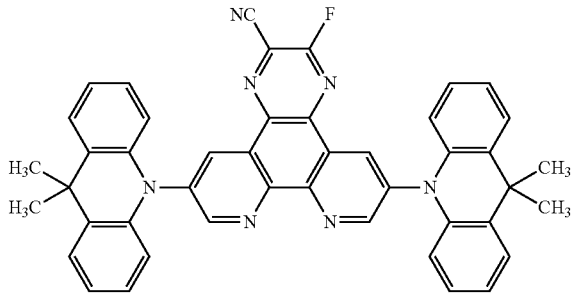

-continued
[Chemical Formula 38]
(Compound 31)
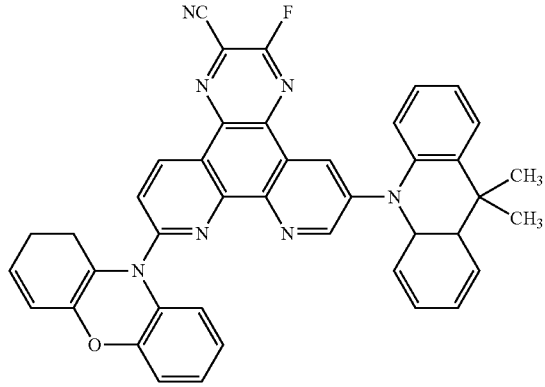
[Chemical Formula 39]
(Compound 32)
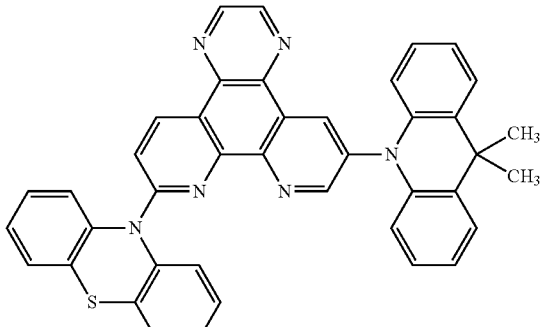
[Chemical Formula 40]
(Compound 33)
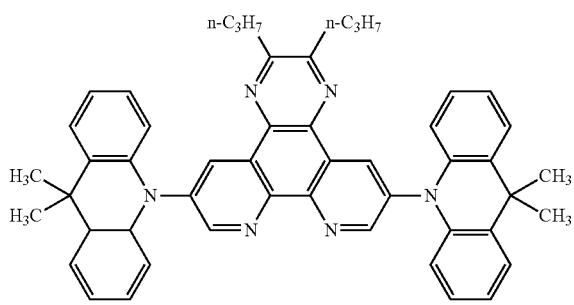
[Chemical Formula 41]
(Compound 34)
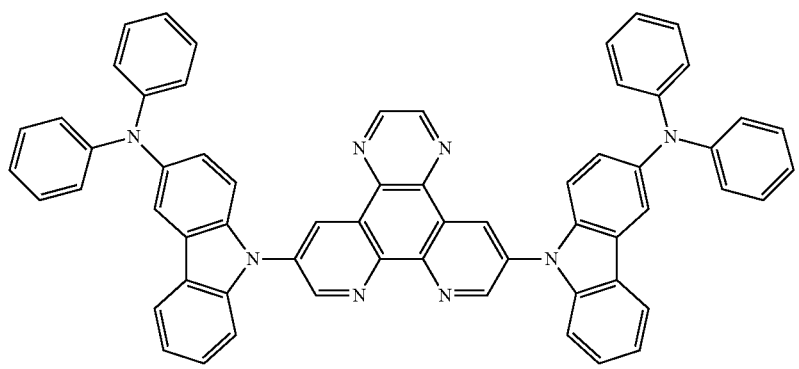

-continued
[Chemical Formula 42]
(Compound 35)
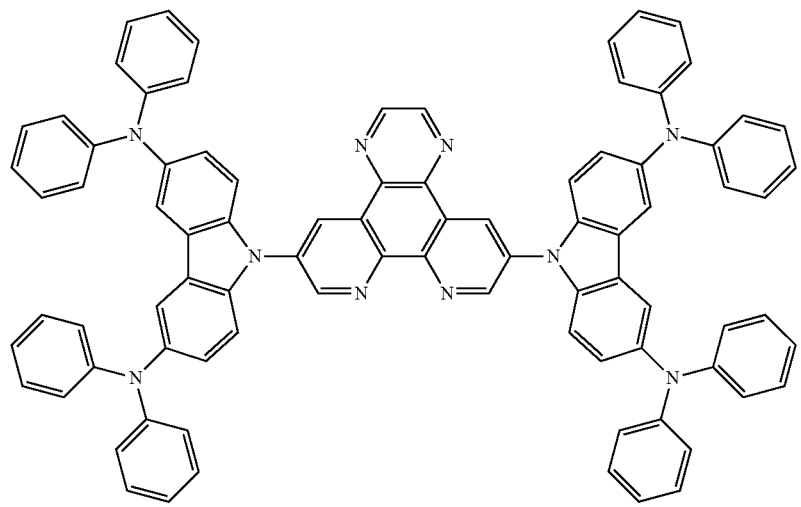
[Chemical Formula 43]
(Compound 36)
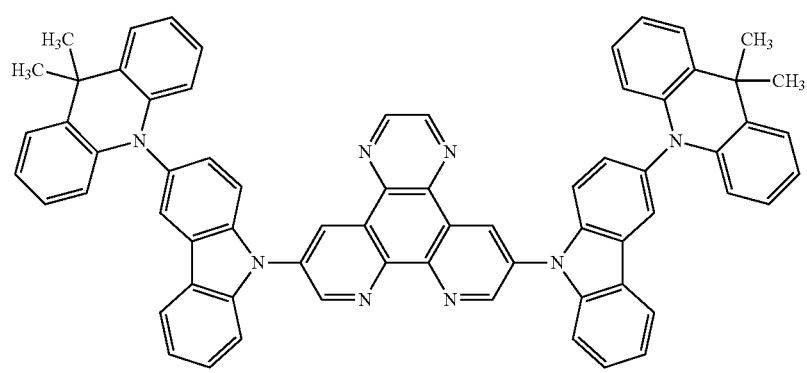
[Chemical Formula 44]
(Compound 37)
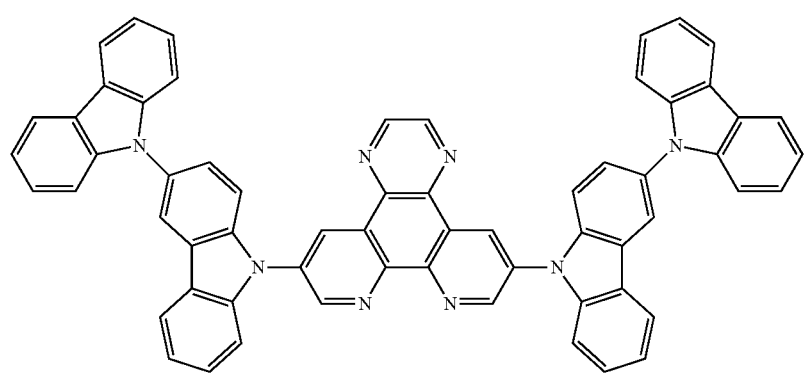

-continued
[Chemical Formula 45]
(Compound 38)
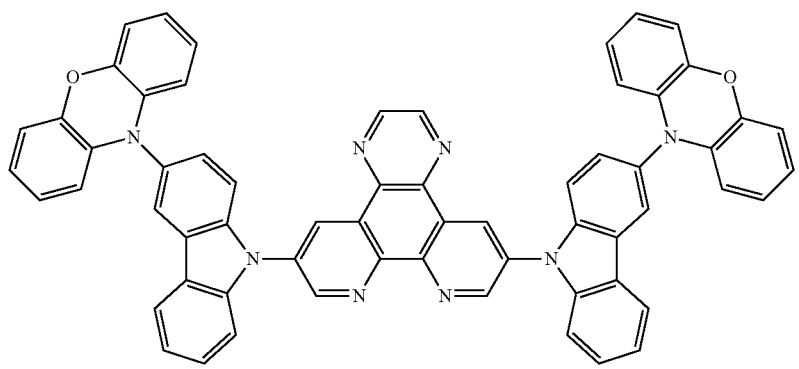
[Chemical Formula 46]
(Compound 39)
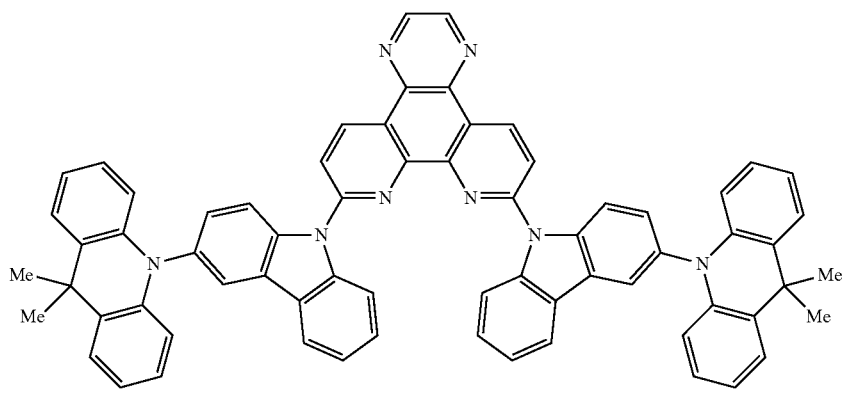
[Chemical Formula 47]
(Compound 40)
[Chemical Formula 48]
(Compound 41)
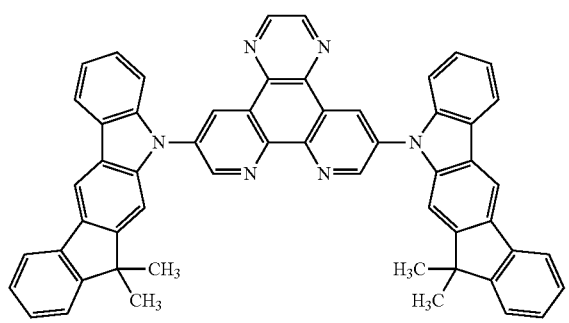 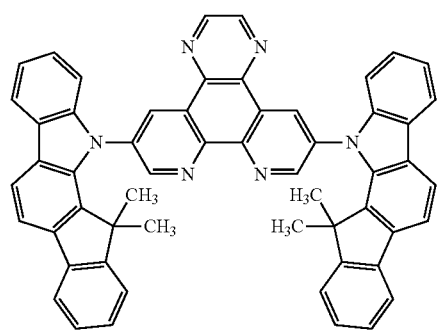
[Chemical Formula 49]
(Compound 42)
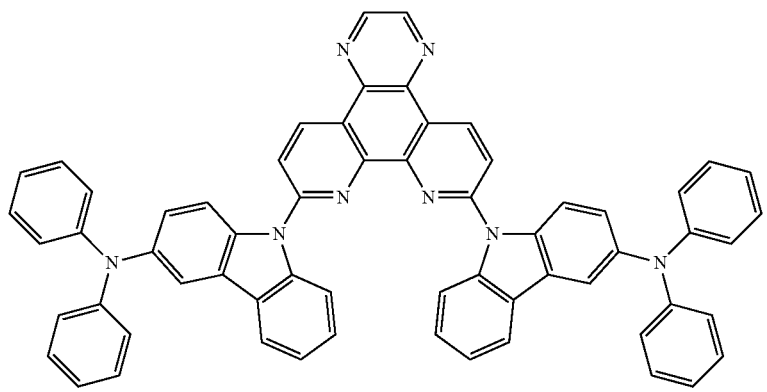

[Chemical Formula 50] (Compound 43)
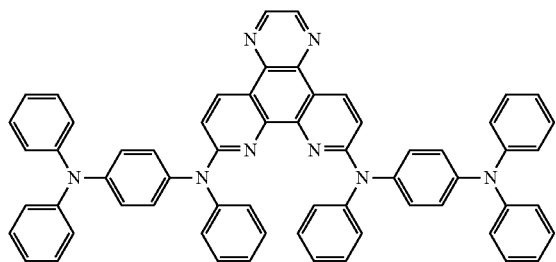
[Chemical Formula 51] (Compound 44)
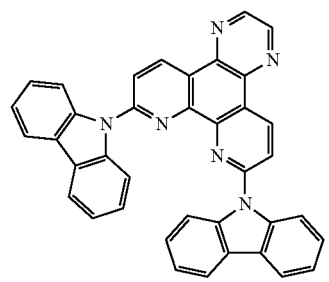
[Chemical Formula 52] (Compound 45)
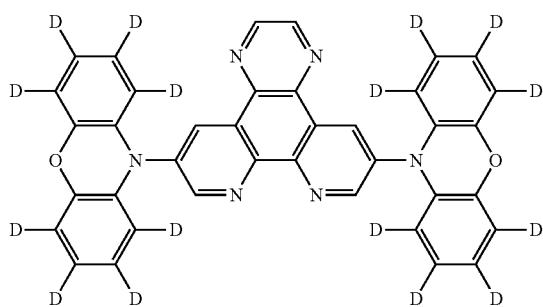
[Chemical Formula 53] (Compound 46)
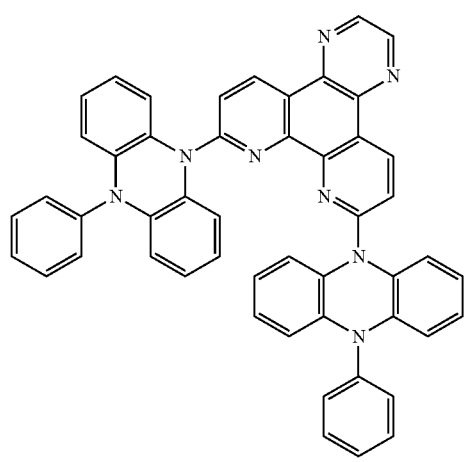
[Chemical Formula 54] (Compound 47)
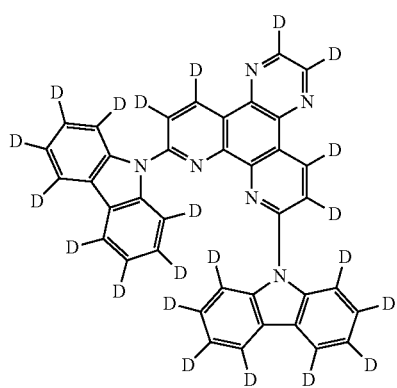
[Chemical Formula 55] (Compound 48)
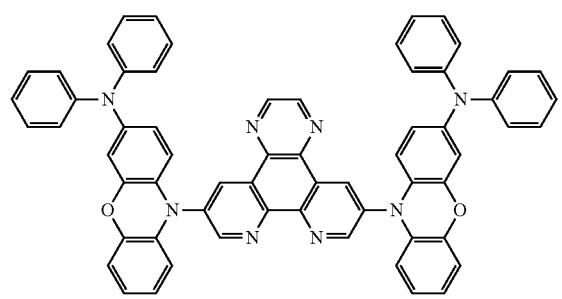

[Chemical Formula 56]
(Compound 49)
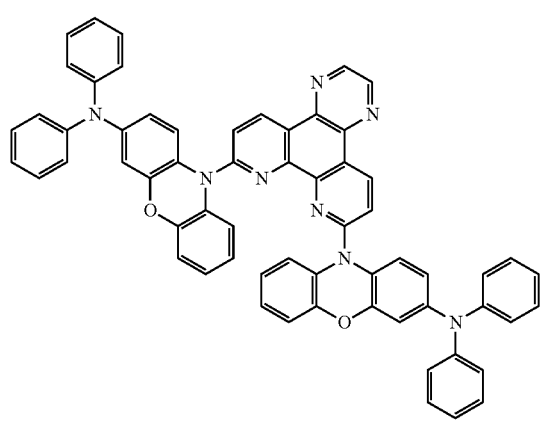
[Chemical Formula 57]
(Compound 50)
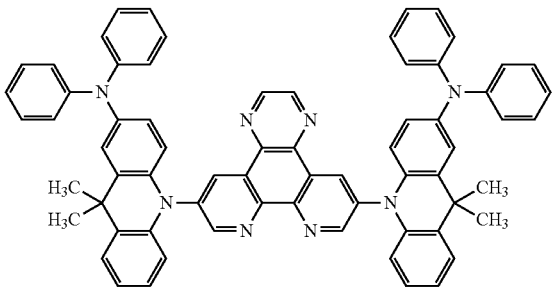
[Chemical Formula 58]
(Compound 51)
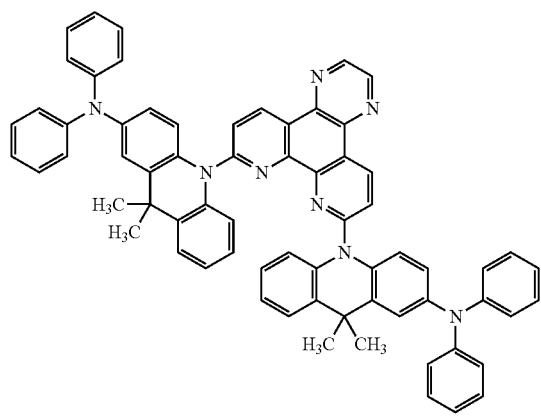
[Chemical Formula 59]
(Compound 52)
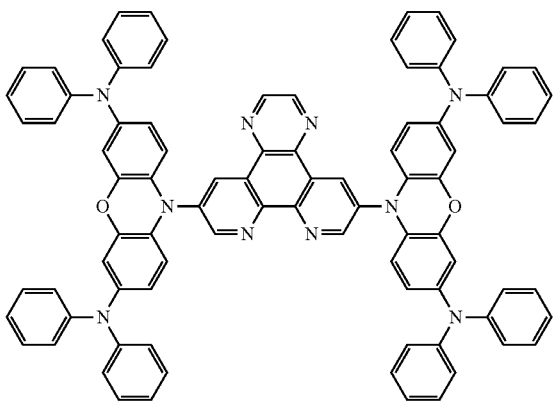
[Chemical Formula 60]
(Compound 53)
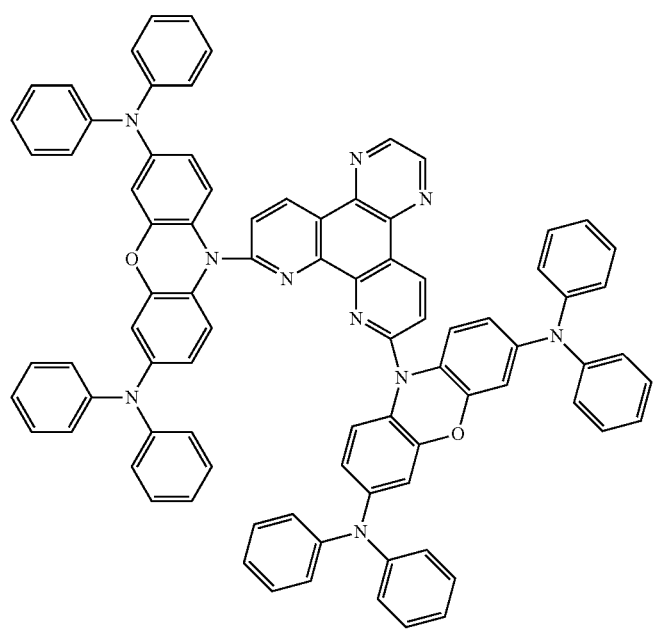

-continued
[Chemical Formula 61]
(Compound 54)
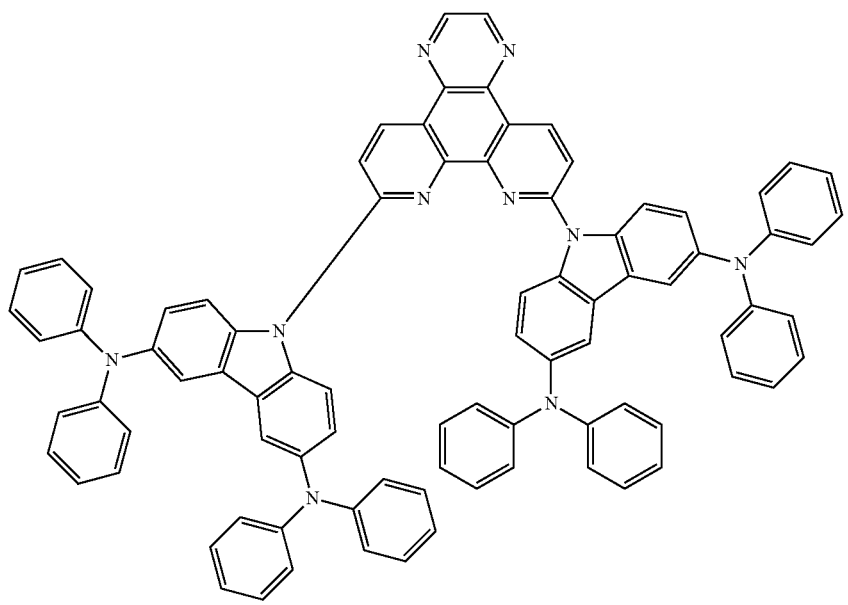
[Chemical Formula 62]
(Compound 55)
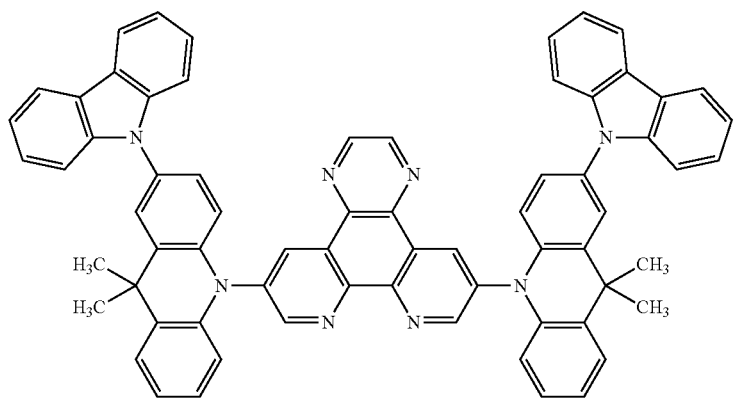
[Chemical Formula 63]
(Compound 56)
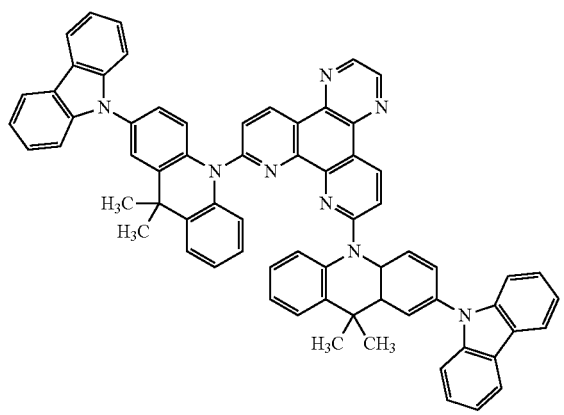
[Chemical Formula 64]
(Compound 57)
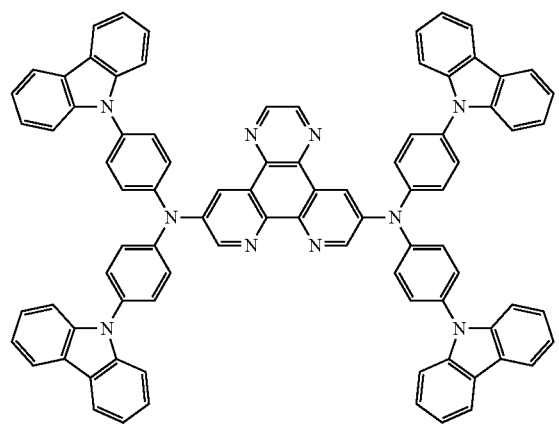

[Chemical Formula 65]
(Compound 58)
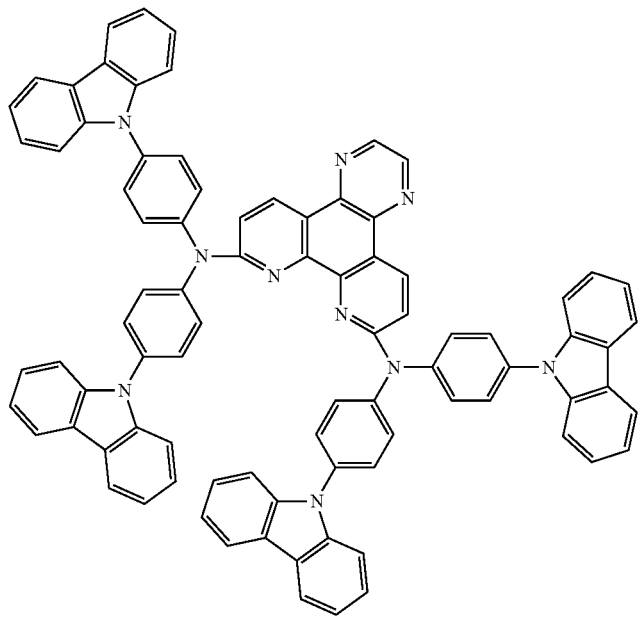
[Chemical Formula 66]
(Compound 59)
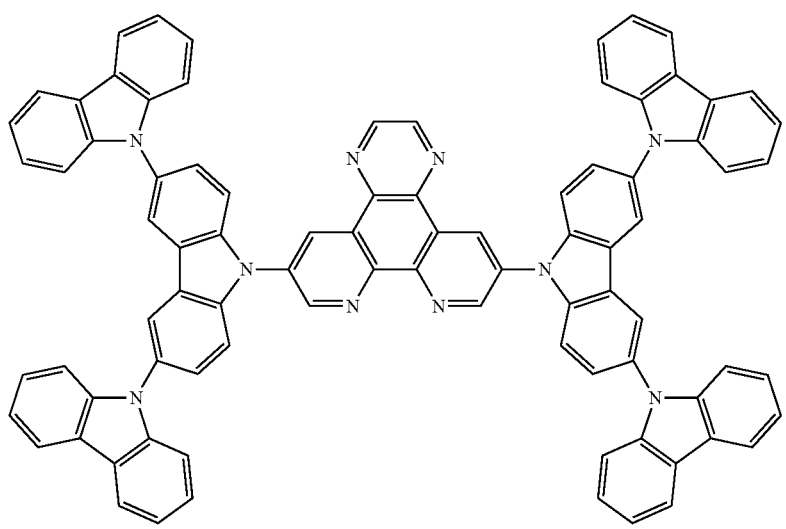
[Chemical Formula 67]
(Compound 60)
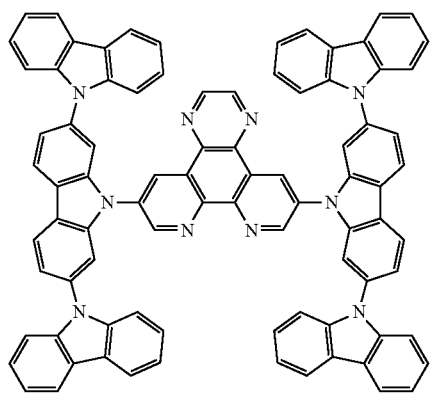
[Chemical Formula 68]
(Compound 61)
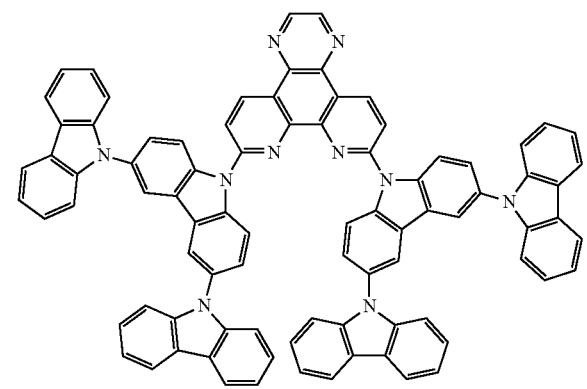

[Chemical Formula 69]
(Compound 62)
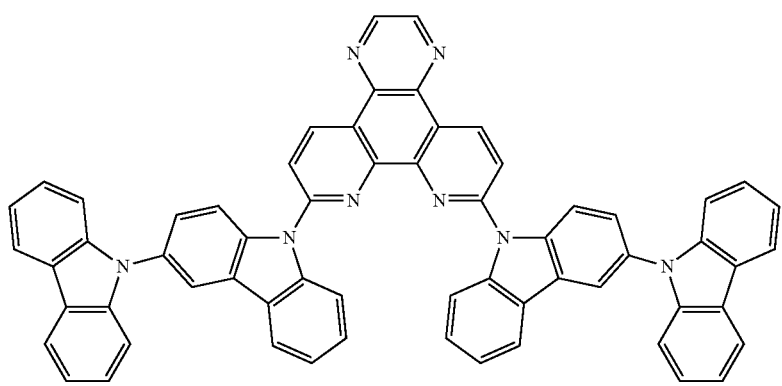
[Chemical Formula 70]
(Compound 63)
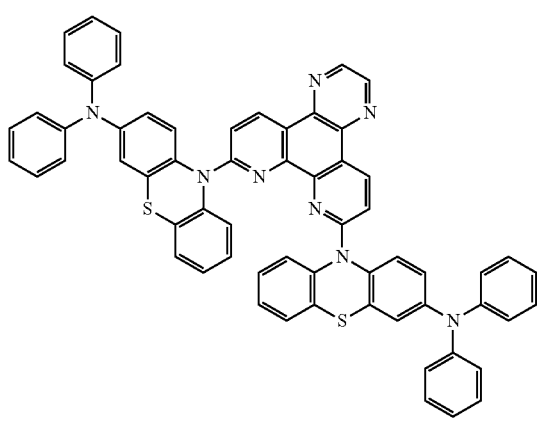
[Chemical Formula 71]
(Compound 64)
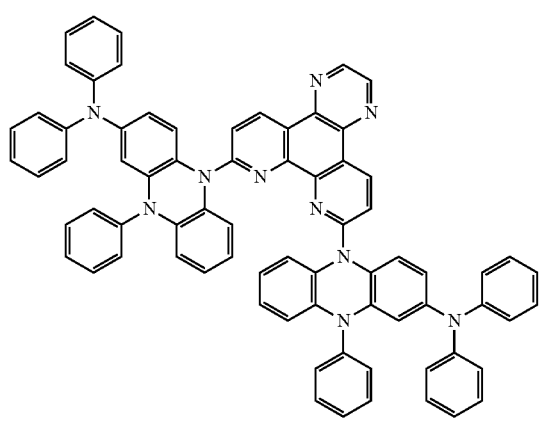
[Chemical Formula 72]
(Compound 65)
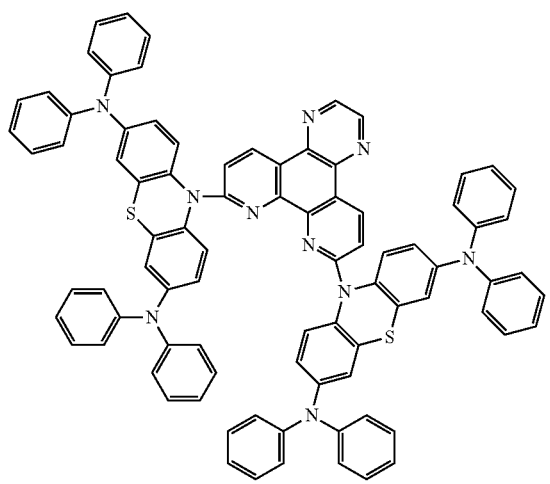
[Chemical Formula 73]
(Compound 66)
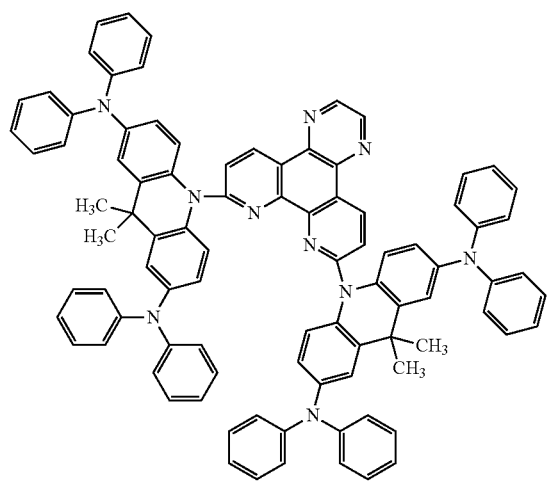

[Chemical Formula 74]
(Compound 67)
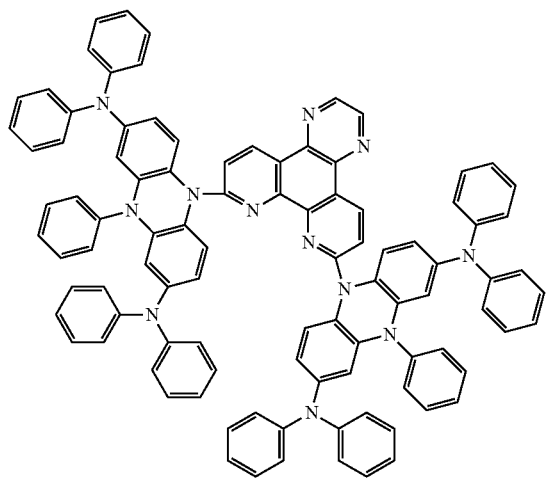
[Chemical Formula 75]
(Compound 68)
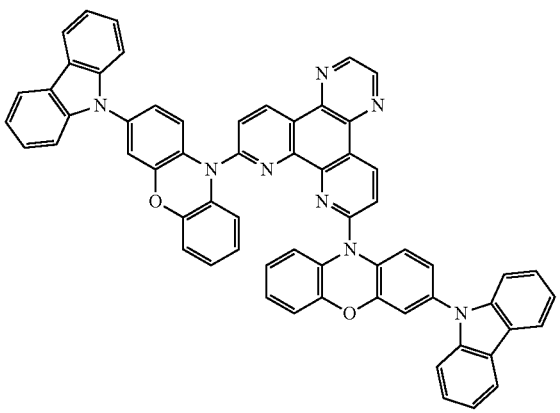
[Chemical Formula 76]
(Compound 69)
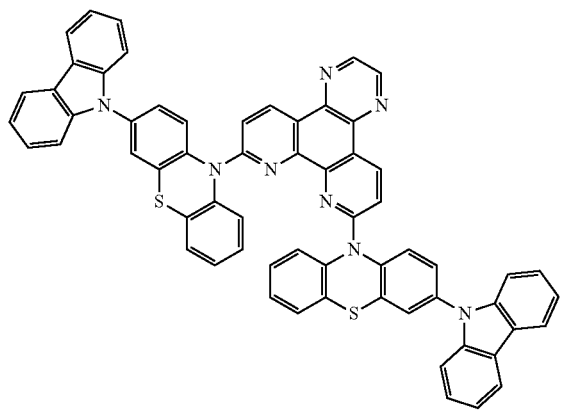
[Chemical Formula 77]
(Compound 70)
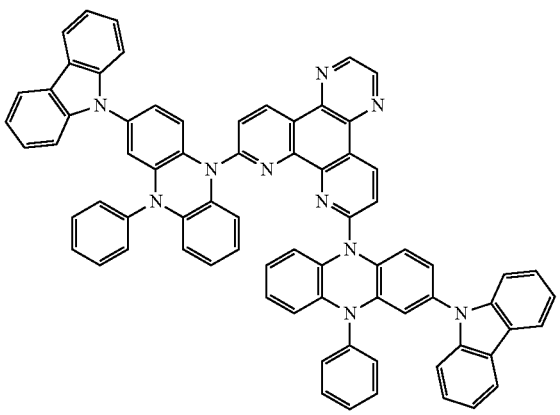
[Chemical Formula 78]
(Compound 71)
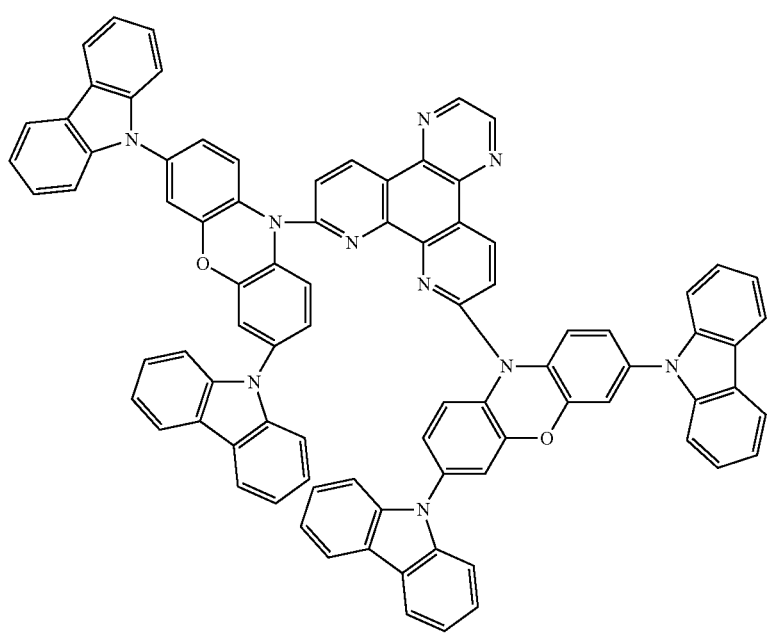

-continued
[Chemical Formula 79]
(Compound 72)
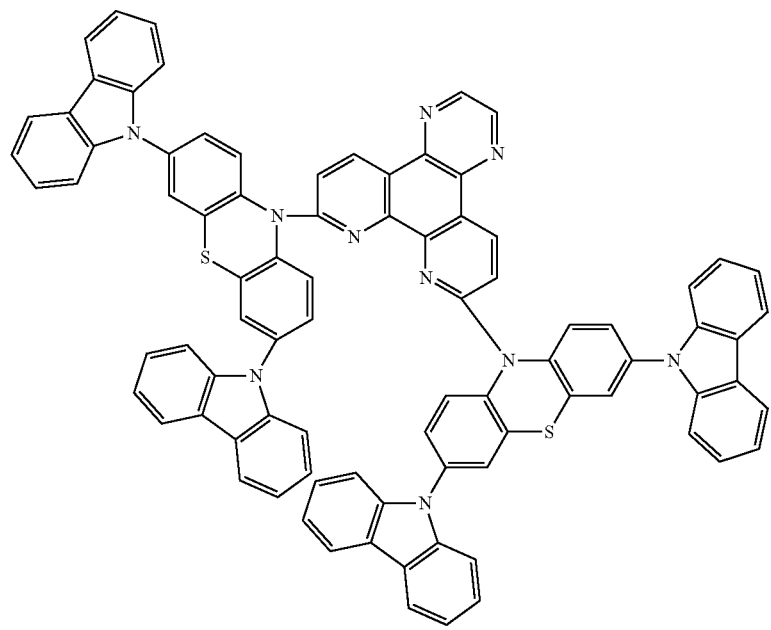
[Chemical Formula 80]
(Compound 73)
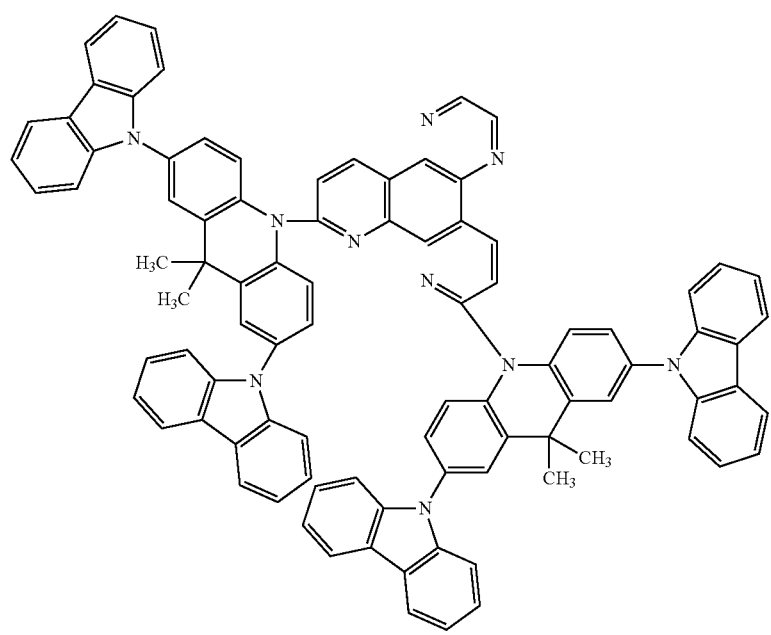

[Chemical Formula 81]
(Compound 74)
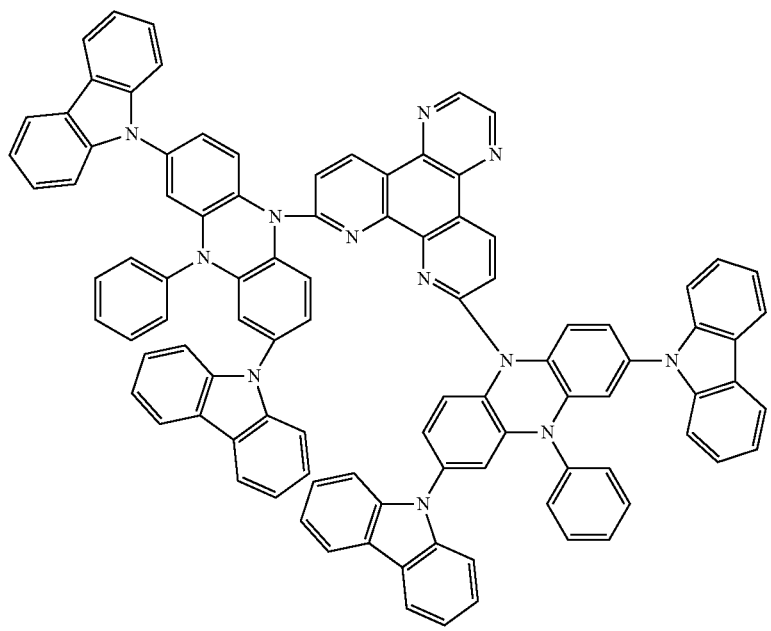
[Chemical Formula 82]
(Compound 75)
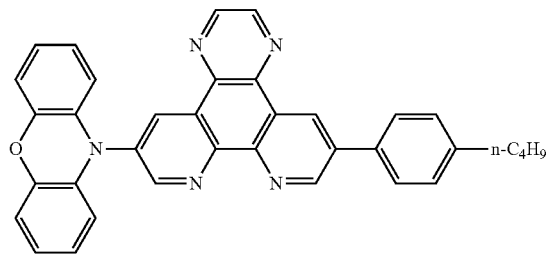
[Chemical Formula 83]
(Compound 76)
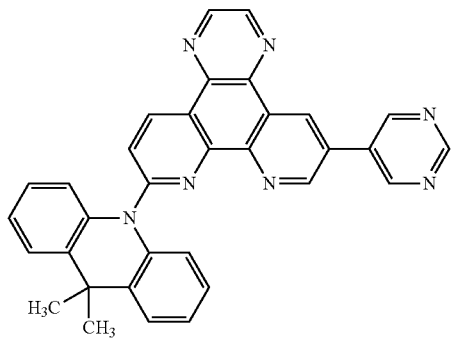
[Chemical Formula 84]
(Compound 77)
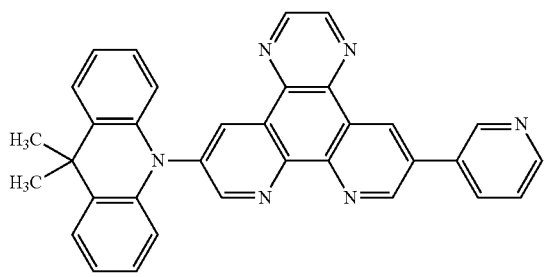
[Chemical Formula 85]
(Compound 78)
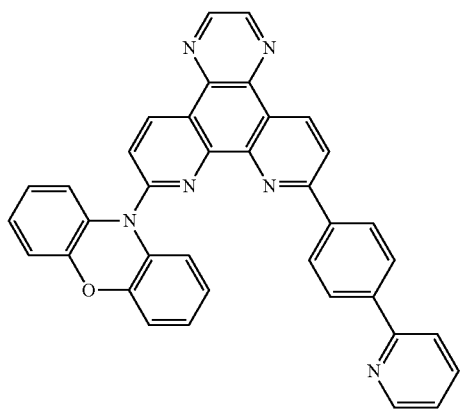

[Chemical Formula 86]
(Compound 79)
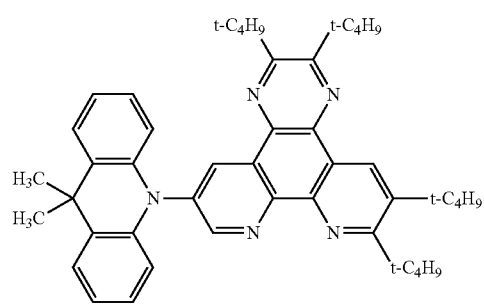
[Chemical Formula 87]
(Compound 80)
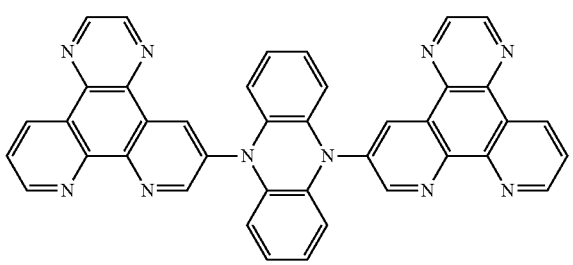
[Chemical Formula 88]
(Compound 81)
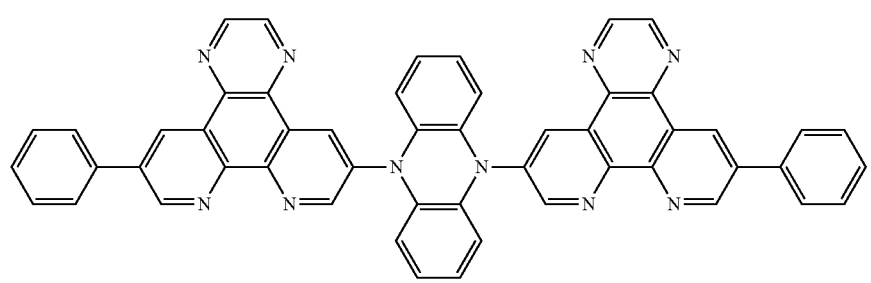
[Chemical Formula 89]
(Compound 82)
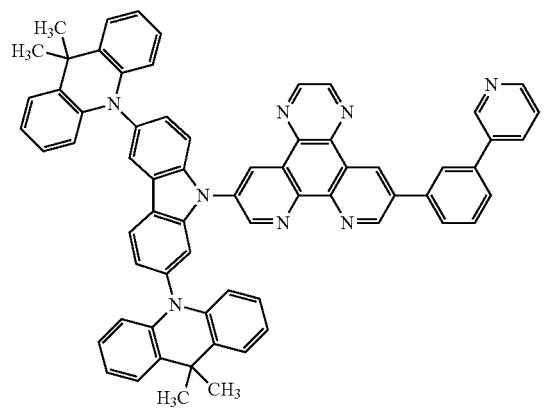
[Chemical Formula 90]
(Compound 83)
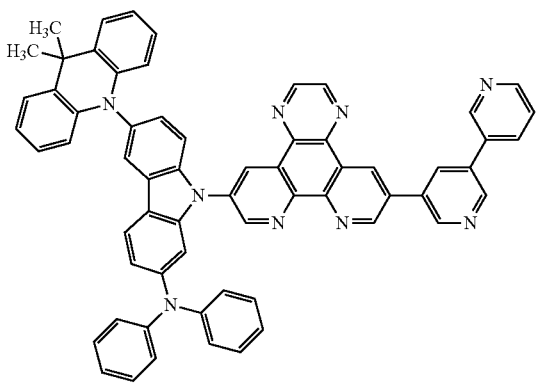
[Chemical Formula 91]
(Compound 84)
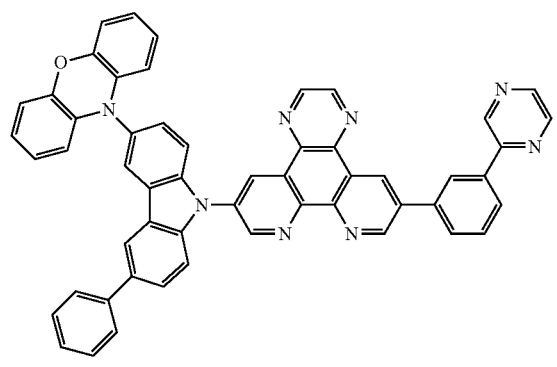
[Chemical Formula 92]
(Compound 85)
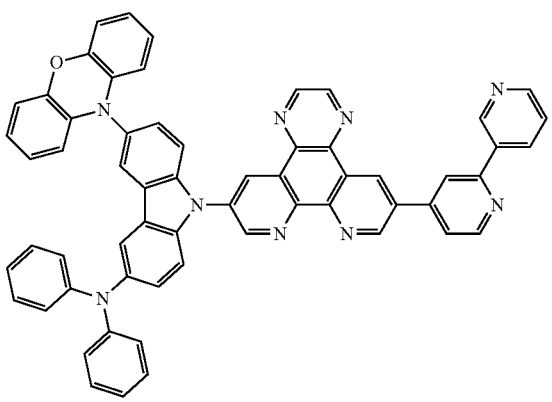

[Chemical Formula 93]
(Compound 86)
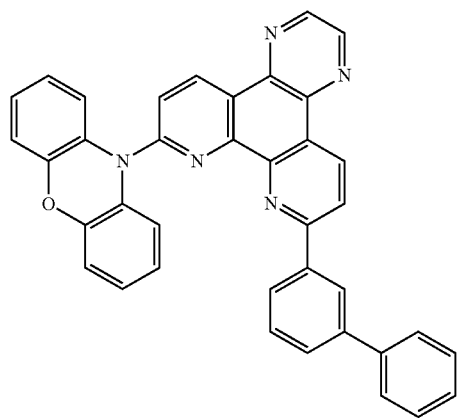
[Chemical Formula 94]
(Compound 87)
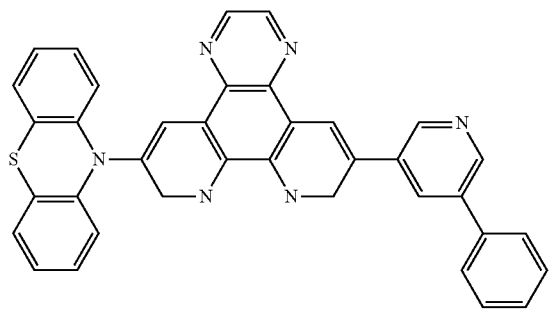
[Chemical Formula 95]
(Compound 88)
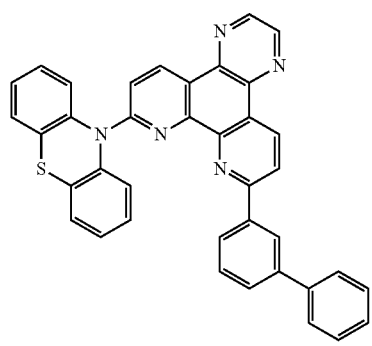
[Chemical Formula 96]
(Compound 89)
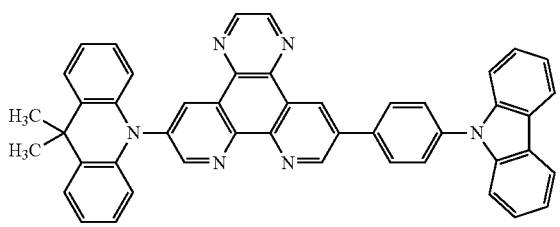
[Chemical Formula 97]
(Compound 90)
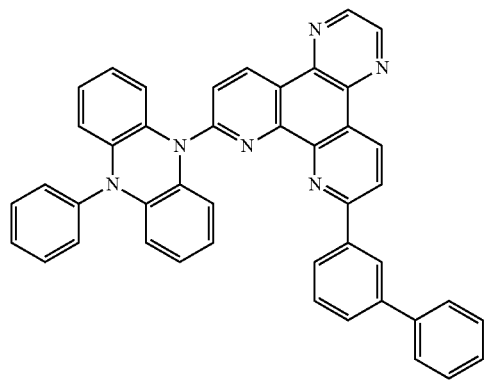
[Chemical Formula 98]
(Compound 91)
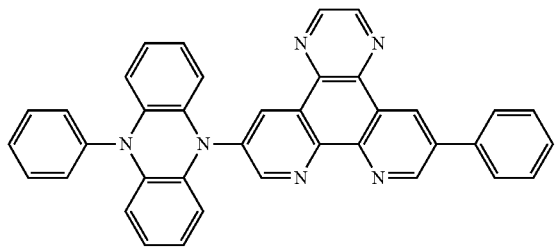

[Chemical Formula 99]
(Compound 92)
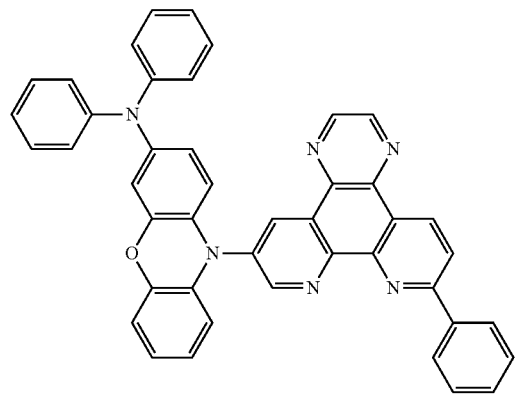
[Chemical Formula 100]
(Compound 93)
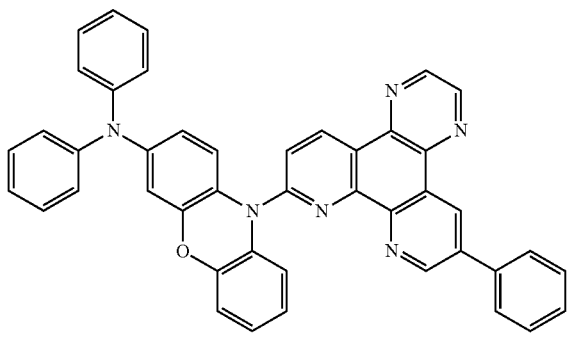
[Chemical Formula 101]
(Compound 94)
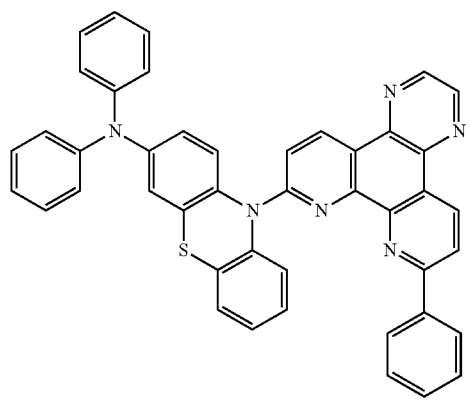
[Chemical Formula 102]
(Compound 95)
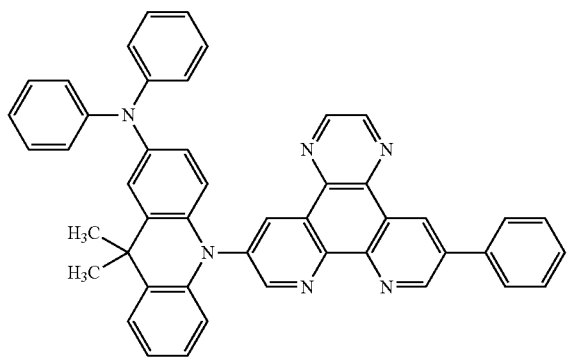
[Chemical Formula 103]
(Compound 96)
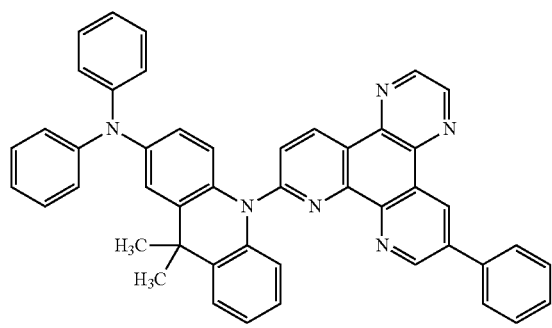
[Chemical Formula 104]
(Compound 97)
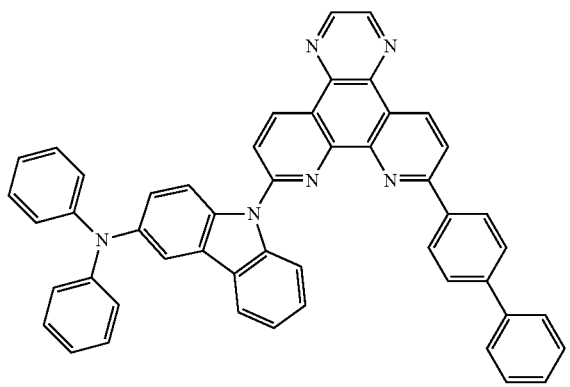

-continued
[Chemical Formula 105]
(Compound 98)
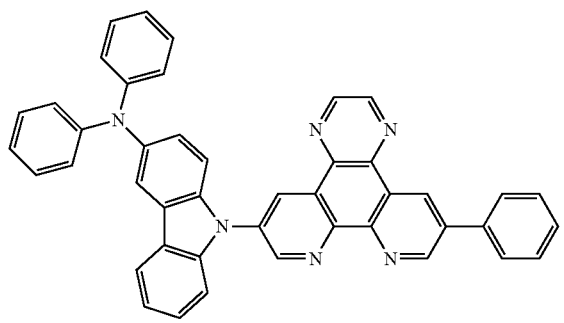
[Chemical Formula 106]
(Compound 99)
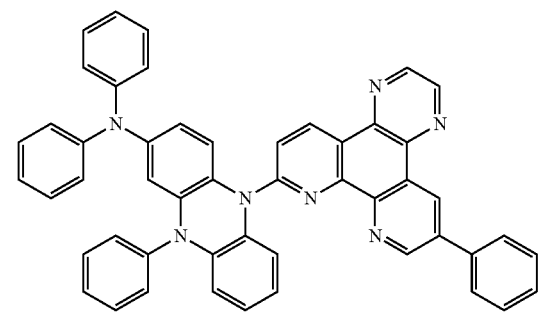
[Chemical Formula 107]
(Compound 100)
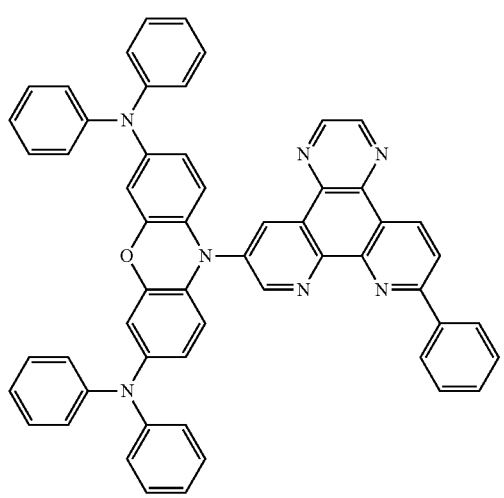
[Chemical Formula 108]
(Compound 101)
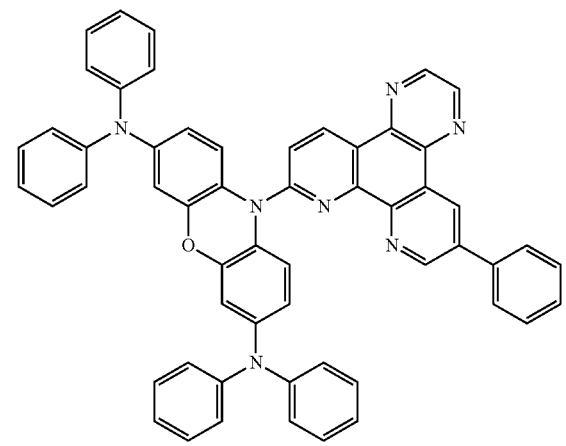
[Chemical Formula 109]
(Compound 102)
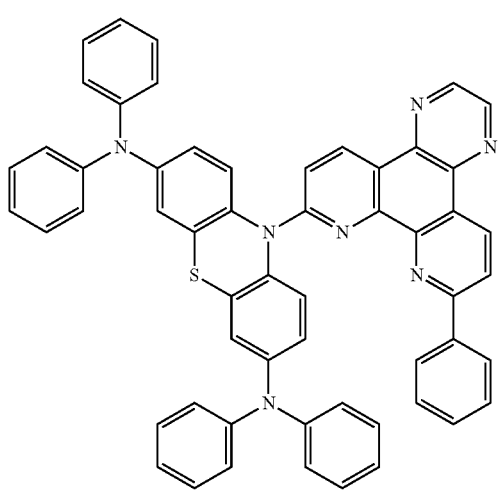
[Chemical Formula 110]
(Compound 103)
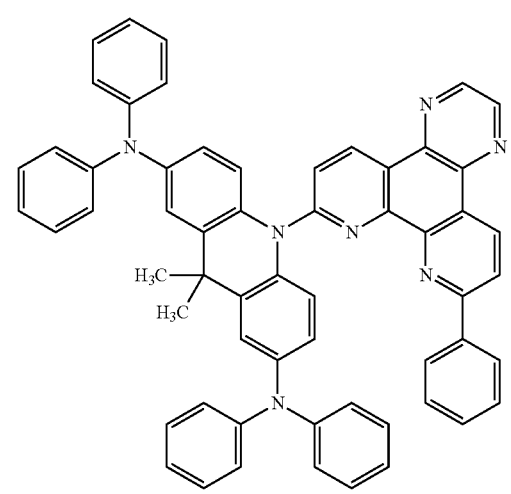

-continued
[Compound Formula 111]
(Compound 104)
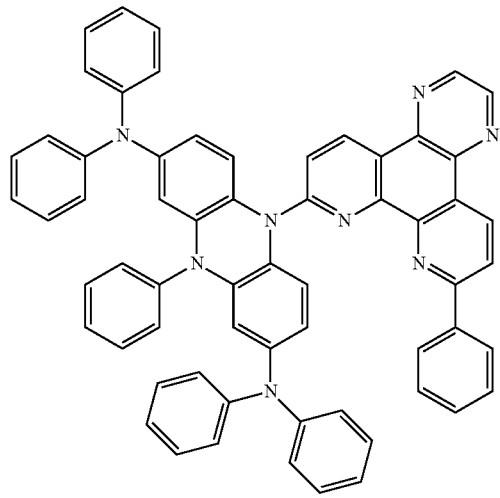
[Compound Formula 112]
(Compound 105)
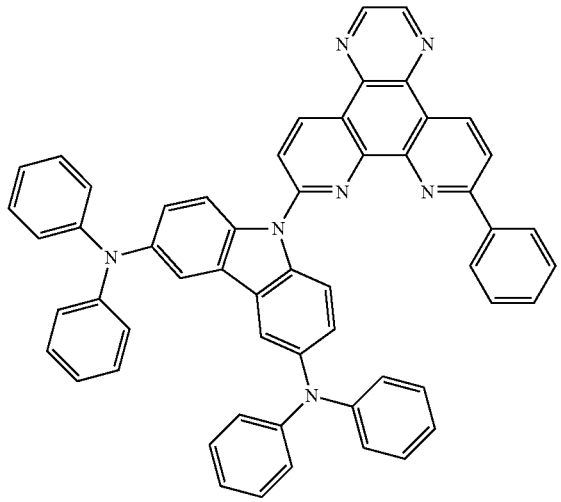
[Compound Formula 113]
(Compound 106)
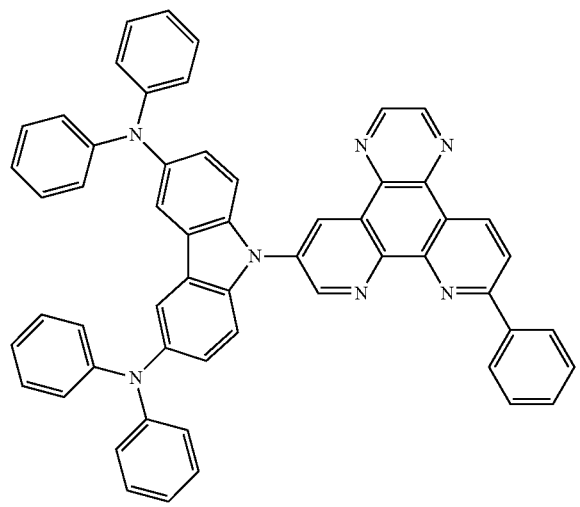
[Compound Formula 114]
(Compound 107)
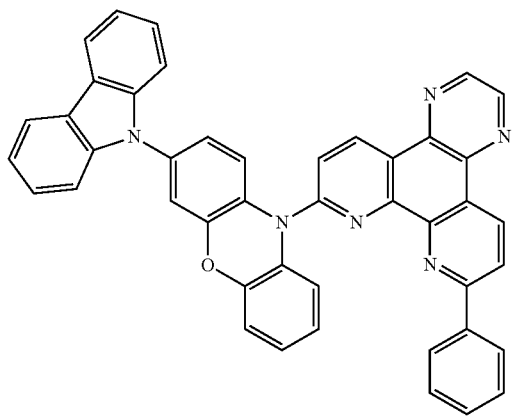
[Chemical Formula 115]
(Compound 108)
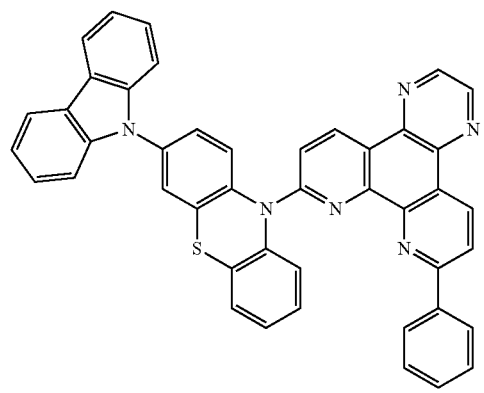
[Chemical Formula 116]
(Compound 109)
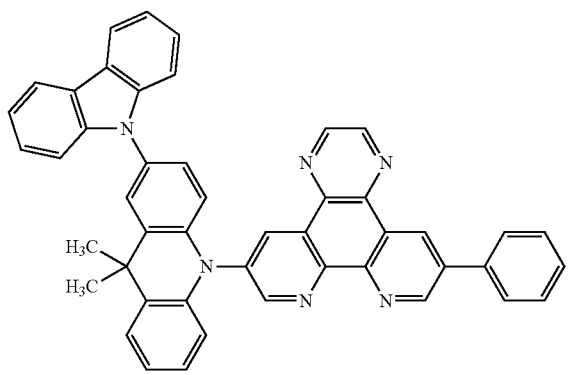

-continued
[Chemical Formula 117]
(Compound 110)
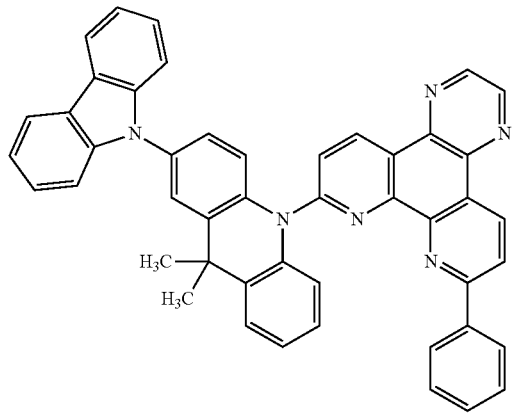
[Chemical Formula 118]
(Compound 111)
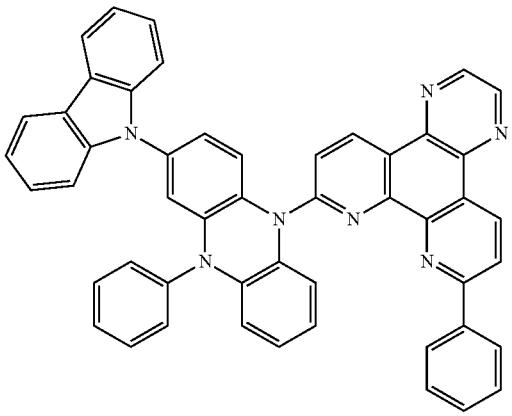
[Chemical Formula 119]
(Compound 112)
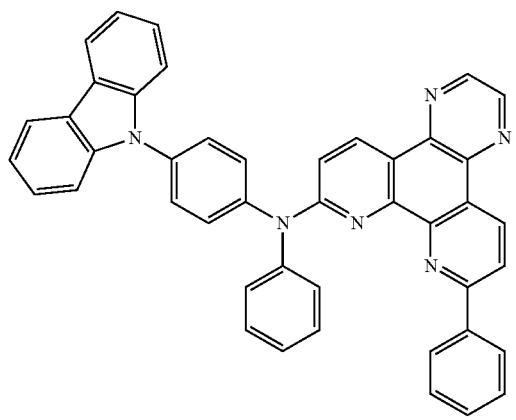
[Chemical Formula 120]
(Compound 113)
[Chemical Formula 121]
(Compound 114)
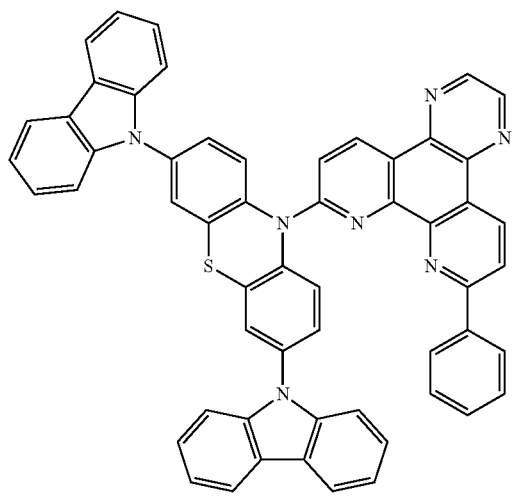
[Chemical Formula 122]
(Compound 115)
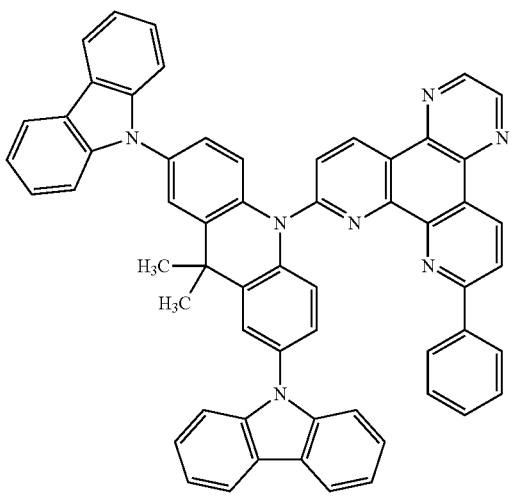

[Chemical Formula 123]
(Compound 116)
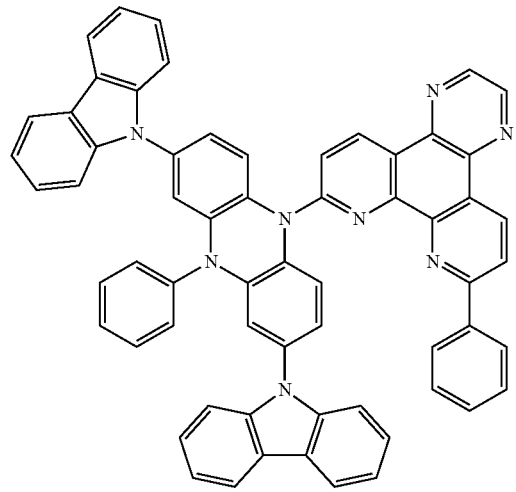
[Chemical Formula 124]
(Compound 117)
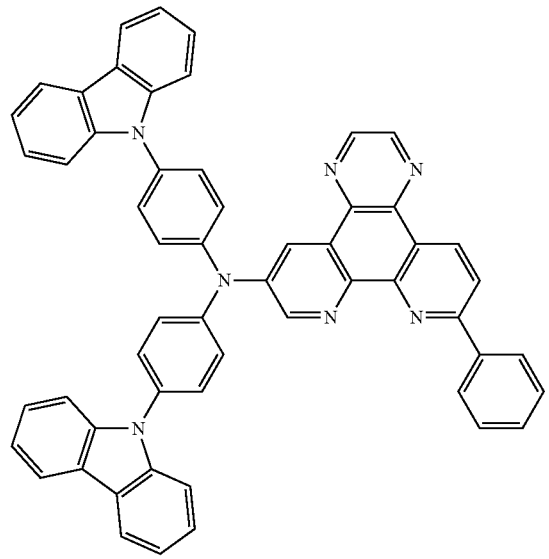
[Chemical Formula 125]
(Compound 118)
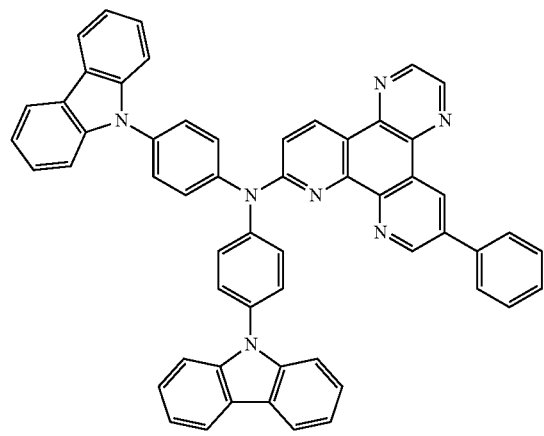
[Chemical Formula 126]
(Compound 119)
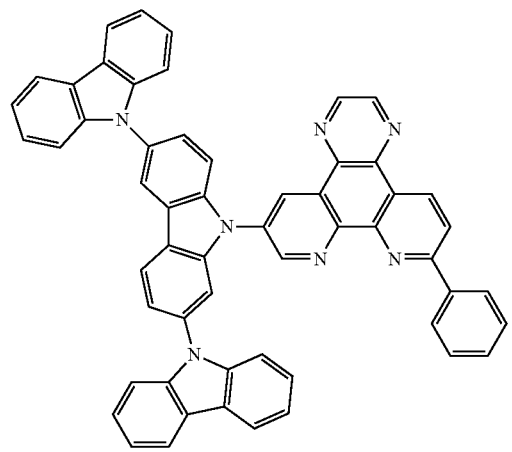

[Chemical Formula 127]

(Compound 120)

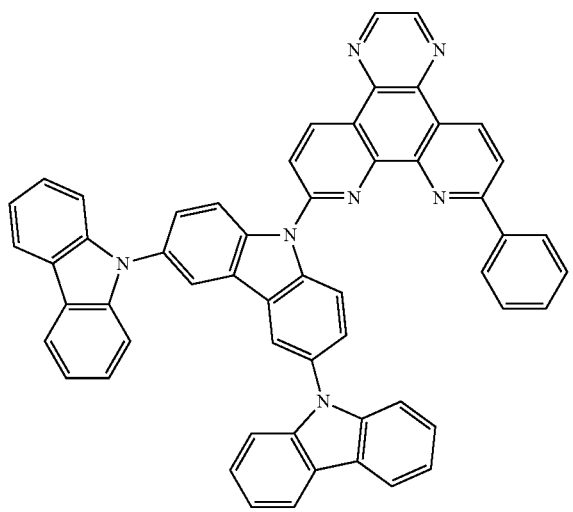

These compounds were purified by methods such as column chromatography; adsorption using, for example, a silica gel, activated carbon, or activated clay; recrystallization or crystallization using a solvent; and sublimation. The compounds were identified by an NMR analysis. A work function was measured as a material property value. The work function can be used as an index of energy level as a material for a light emitting layer, or an index of hole blocking capability.

For the measurement of work function, a 100 nm-thick thin film was fabricated on an ITO substrate, and an atmosphere photoelectron spectrometer (AC-3 produced by Riken Keiki Co., Ltd.) was used.

The organic EL device of the present invention may have a structure including an anode, a hole transport layer, a light emitting layer, a hole blocking layer, an electron transport layer, and a cathode successively formed on a substrate, optionally with a hole injection layer between the anode and the hole transport layer, an electron injection layer between the electron transport layer and the cathode, or an electron blocking layer between the light emitting layer and the hole transport layer. In such a multilayer structure, some of the organic layers may be omitted. For example, the device may be configured to include an anode, a hole transport layer, a light emitting layer, an electron transport layer, and a cathode successively formed on a substrate.

Each of the light emitting layer, the hole transport layer, and the electron transport layer may have a laminate structure of two or more layers.

Electrode materials with high work functions such as ITO and gold are used as the anode of the organic EL device of the present invention. Examples of the material used for the hole injection layer of the organic EL device of the present invention can be naphthalenediamine derivatives; starburst-type triphenylamine derivatives; triphenylamine trimers and tetramers such as an arylamine compound having a structure in which three or more triphenylamine structures are joined within the molecule via a single bond or a divalent group that does not contain a heteroatom; accepting heterocyclic compounds such as hexacyano azatriphenylene; and coating-type polymer materials, in addition to porphyrin compounds as represented by copper phthalocyanine. These materials may be formed into a thin film by a vapor deposition method, or other known methods such as a spin coating method and an inkjet method.

Examples of the material used for the hole transport layer of the organic EL device of the present invention can be benzidine derivatives such as N,N'-diphenyl-N,N'-di(m-tolyl)-benzidine (TPD), N,N'-diphenyl-N,N'-di(α-naphthyl)-benzidine (NPD), and N,N,N',N'-tetrabiphenylylbenzidine; 1,1-bis[(di-4-tolylamino)phenyl]cyclohexane (TAPC); various triphenylamine trimers and tetramers; and carbazole derivatives, in addition to compounds containing a m-carbazolylphenyl group. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer. Examples of the material used for the hole injection/transport layer can be coating-type polymer materials such as poly(3,4-ethylenedioxythiophene) (PEDOT)/poly(styrene sulfonate) (PSS). These materials may be formed into a thin-film by a vapor deposition method, or other known methods such as a spin coating method and an inkjet method.

The material used for the hole injection layer or the hole transport layer may be obtained by p-doping materials such as trisbromophenylamine hexachloroantimony, and radialene derivatives (refer to WO2014/009310, for example) into a material commonly used for these layers, or may be, for example, polymer compounds each having, as a part of the compound structure, a structure of a benzidine derivative such as TPD.

Examples of the material used for the electron blocking layer of the organic EL device of the present invention can be compounds having an electron blocking effect, including carbazole derivatives such as 4,4',4"-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl)adamantane (Ad-Cz); and compounds having a triphenylsilyl group and a triarylamine structure, as represented by 9-[4-(carbazol-9-yl)phenyl]-9-[4-(triphenylsilyl)phenyl]-9 H-fluorene. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer. These materials may be formed into a thin film by a vapor deposition method, or other known methods such as a spin coating method and an inkjet method.

Examples of the material used for the light emitting layer of the organic EL device of the present invention can be the compounds of general formula (1) having a tetraazatriphenylene ring structure of the present invention; delayed fluorescence-emitting materials such as CDCB derivatives of PIC-TRZ (refer to Non-Patent Document 1, for example), CC2TA (refer to Non-Patent Document 3, for example), PXZ-TRZ (refer to Non-Patent Document 4, for example), 4CzIPN or the like (refer to Non-Patent Document 5, for example); various metal complexes including, for example, quinolinol derivative metal complexes such as tris(8-hydroxyquinoline)aluminum ($Alq_3$); anthracene derivatives; bis(styryl)benzene derivatives; pyrene derivatives; oxazole derivatives; and polyparaphenylene vinylene derivatives. Further, the light emitting layer may be made of a host material and a dopant material. In this case, examples of the host material can be the compounds of general formula (1) having a tetraazatriphenylene ring structure of the present invention, mCP, thiazole derivatives, benzimidazole derivatives, and polydialkyl fluorene derivatives. Examples of the dopant material can be the compounds of general formula (1) having a tetraazatriphenylene ring structure of the present invention; delayed fluorescence-emitting materials such as CDCB derivatives of PIC-TRZ, CC2TA, PXZ-TRZ, 4CzIPN or the like; quinacridone, coumarin, rubrene, anthracene, perylene, and derivatives thereof; benzopyran derivatives; rhodamine derivatives; and aminostyryl derivatives. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer.

Further, the light-emitting material may be phosphorescent light-emitting material. Phosphorescent materials as metal complexes of metals such as iridium and platinum may be used as the phosphorescent light-emitting material. Examples of the phosphorescent materials include green phosphorescent materials such as $Ir(ppy)_3$, blue phosphorescent materials such as FIrpic and FIr6, and red phosphorescent materials such as $Btp_2Ir(acac)$ and $Ir(piq)_3$. Here, carbazole derivatives such as 4,4'-di(N-carbazolyl)biphenyl (CBP), TCTA, and mCP may be used as the hole injecting and transporting host material. Compounds such as p-bis(triphenylsilyl)benzene (UGH2), and 2,2',2"-(1,3,5-phenylene)-tris(1-phenyl-1H-benzimidazole) (TPBI) may be used as the electron transporting host material. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer.

In order to avoid concentration quenching, the doping of the host material with the phosphorescent light-emitting material should preferably be made by co-evaporation in a range of 1 to 30 weight percent with respect to the whole light emitting layer.

These materials may be formed into a thin-film by using a vapor deposition method, or other known methods such as a spin coating method and an inkjet method.

It is also possible to produce a device of a structure that includes a light emitting layer produced with the compound of the present invention, and an adjacently laminated light emitting layer produced by using a compound of a different work function as the host material (refer to Non-Patent Document 6, for example).

The hole blocking layer of the organic EL device of the present invention may be formed by using hole blocking compounds such as various rare earth complexes, oxazole derivatives, triazole derivatives, and triazine derivatives, in addition to the compounds of general formula (1) having a tetraazatriphenylene ring structure of the present invention, metal complexes of phenanthroline derivatives such as bathocuproin (BCP), metal complexes of quinolinol derivatives such as aluminum (III) bis(2-methyl-8-quinolinate)-4-phenylphenolate (BAlq), and dibenzothiophene derivatives such as 2,8-bis(diphenylphosphoryl)dibenzo[b,d]thiophene (hereinafter, referred to simply as "PPT"). These materials may also serve as the material of the electron transport layer. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer. These materials may be formed into a thin-film by using a vapor deposition method, or other known methods such as a spin coating method and an inkjet method.

The electron transport layer of the organic EL device of the present invention may be formed by using various metal complexes, triazole derivatives, triazine derivatives, oxadiazole derivatives, thiadiazole derivatives, carbodiimide derivatives, quinoxaline derivatives, phenanthroline derivatives, silole derivatives, and benzimidazole derivatives such as TPBI, in addition to the compounds of general formula (1) having a tetraazatriphenylene ring structure of the present invention, and metal complexes of quinolinol derivatives such as $Alq_3$ and BAlq. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer. These materials may be formed into a thin-film by using a vapor deposition method, or other known methods such as a spin coating method and an inkjet method.

Examples of the material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The material used for the electron injection layer or the electron transport layer may be obtained by N-doping metals such as cesium, or triarylphosphine oxide derivatives (refer to WO2014/195482, for example) into a material commonly used for these layers.

The cathode of the organic EL device of the present invention may be made of an electrode material with a low work function such as aluminum, or an alloy of an electrode material with an even lower work function such as a magnesium-silver alloy, a magnesium-indium alloy, and an aluminum-magnesium alloy.

Specific examples of preferred materials that may be used in the organic EL device of the present invention are shown below, but the materials that may be used in the present invention are not construed as being limited to the following exemplified compounds. The compound that is shown as a material having a particular function may also be used as a material having another function. In the structural formulae of the following exemplary compounds, R and $R_2$ to $R_7$ each independently represent a hydrogen atom or a substituent, and n represents an integer of 3 to 5.

Preferred examples of a compound that may also be used as the host material of the light emitting layer are shown below.

[Chemical Formula 128]

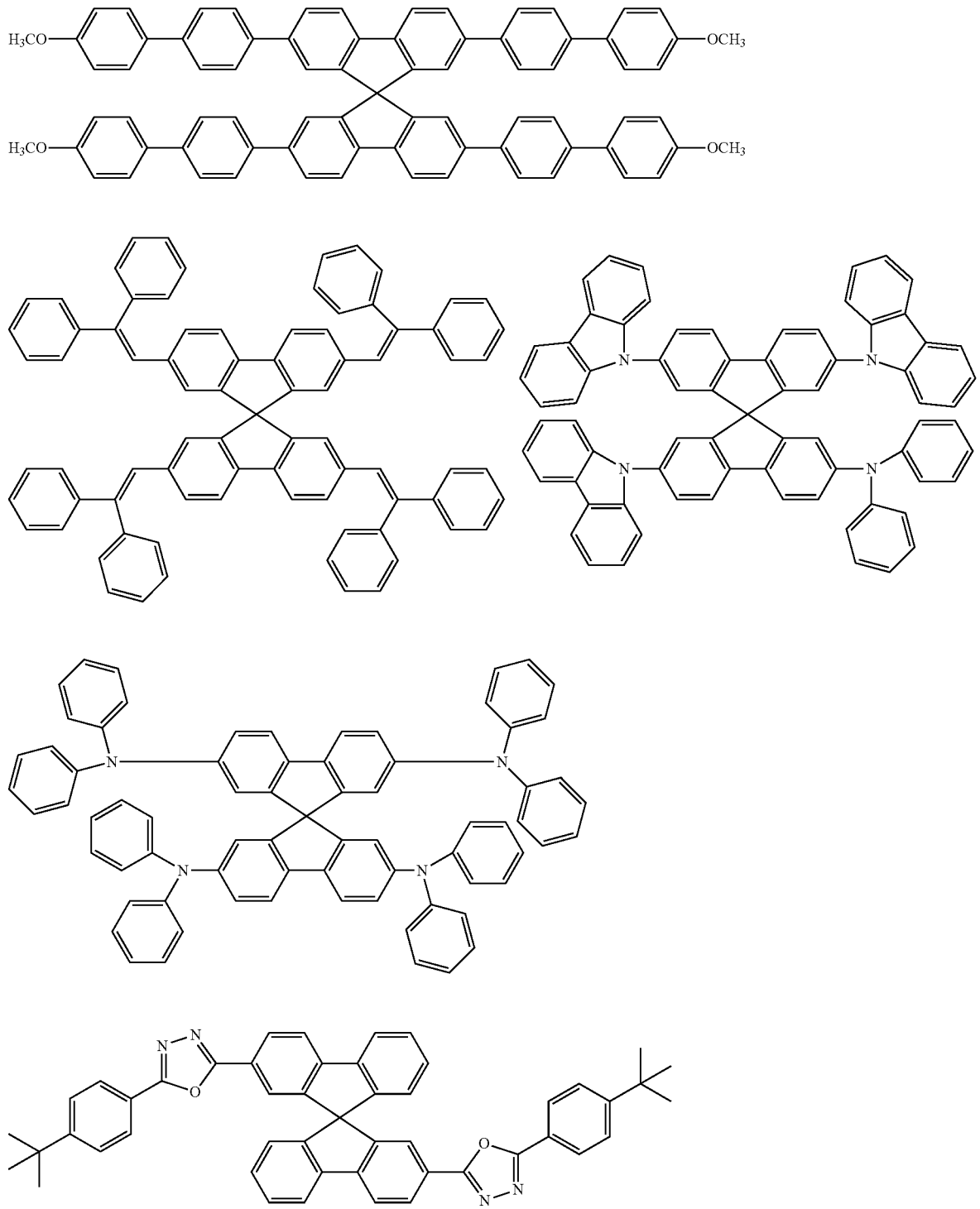

-continued
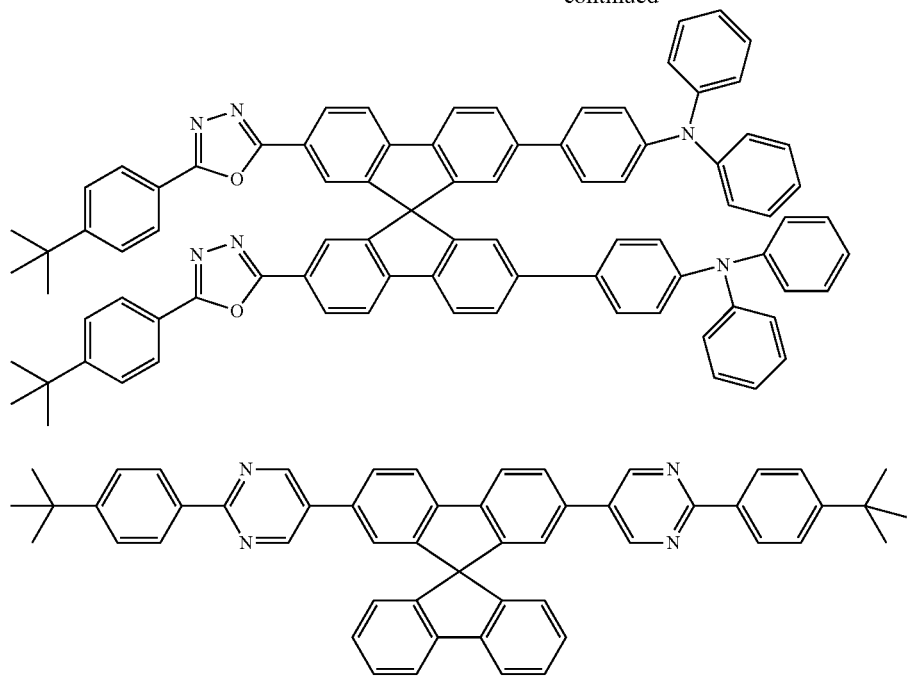
[Chemical Formula 129]
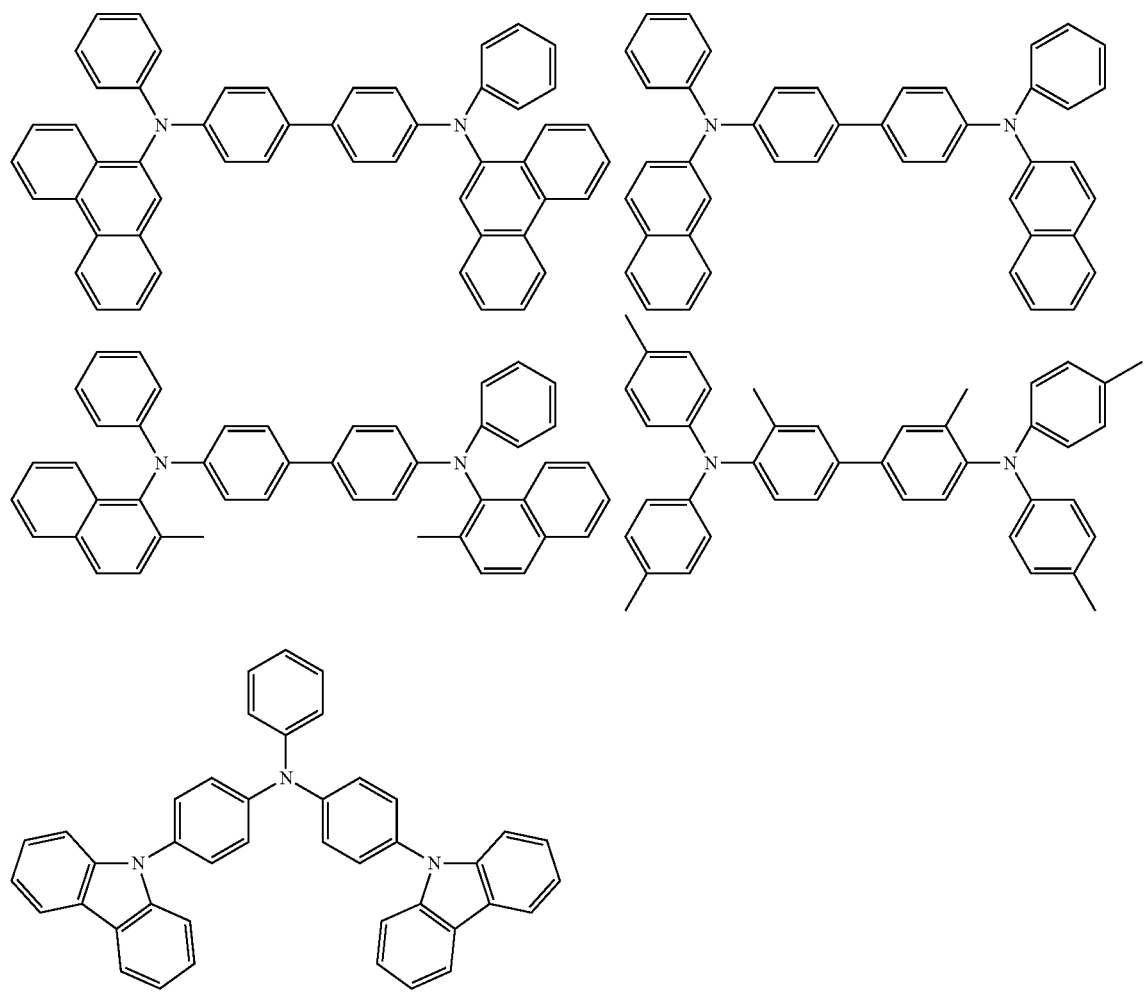

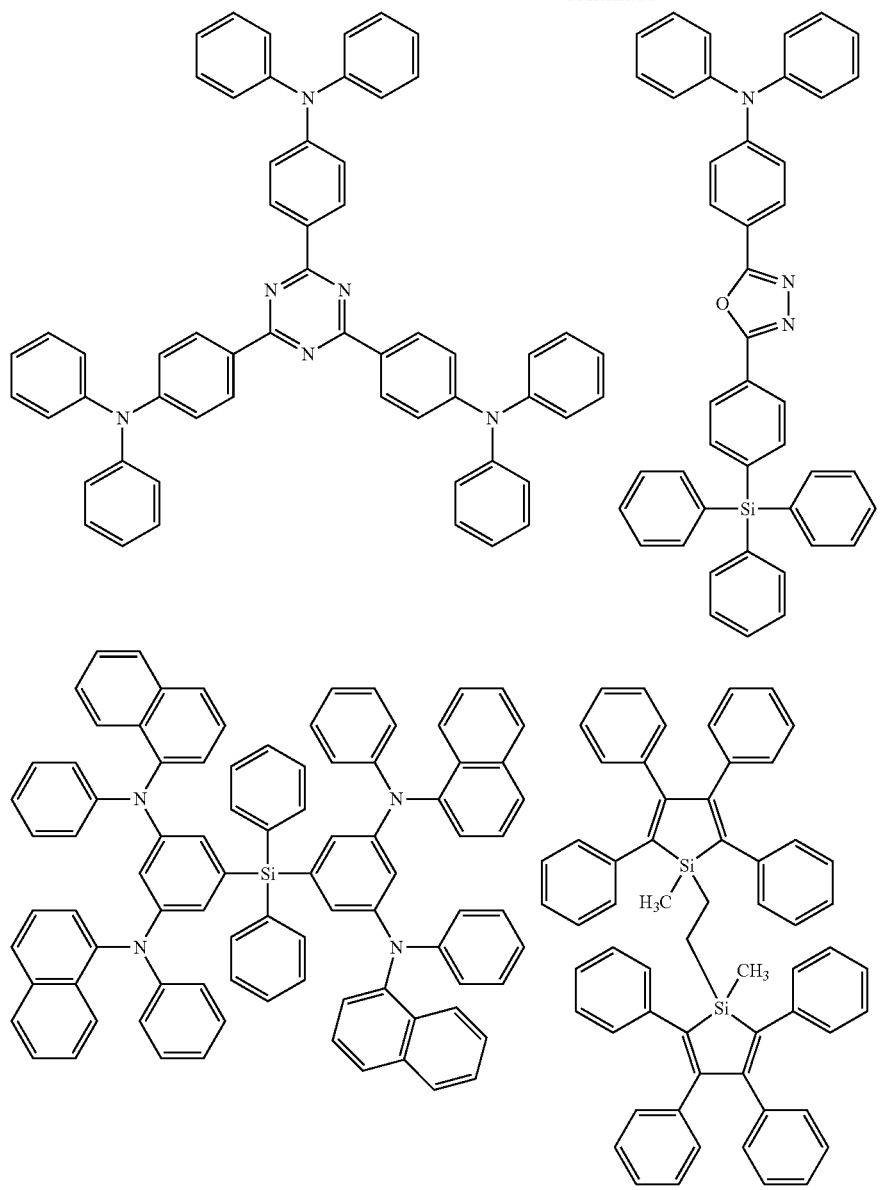
[Chemical Formula 130]
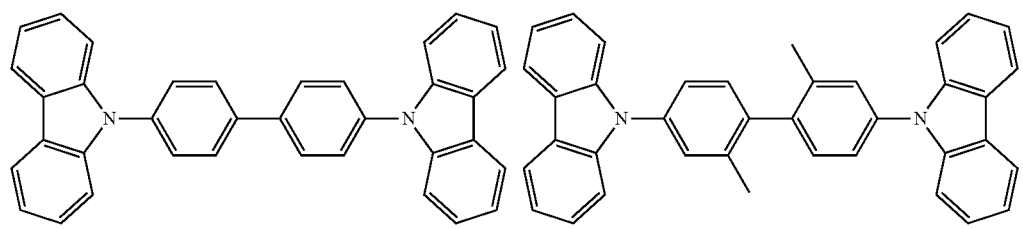

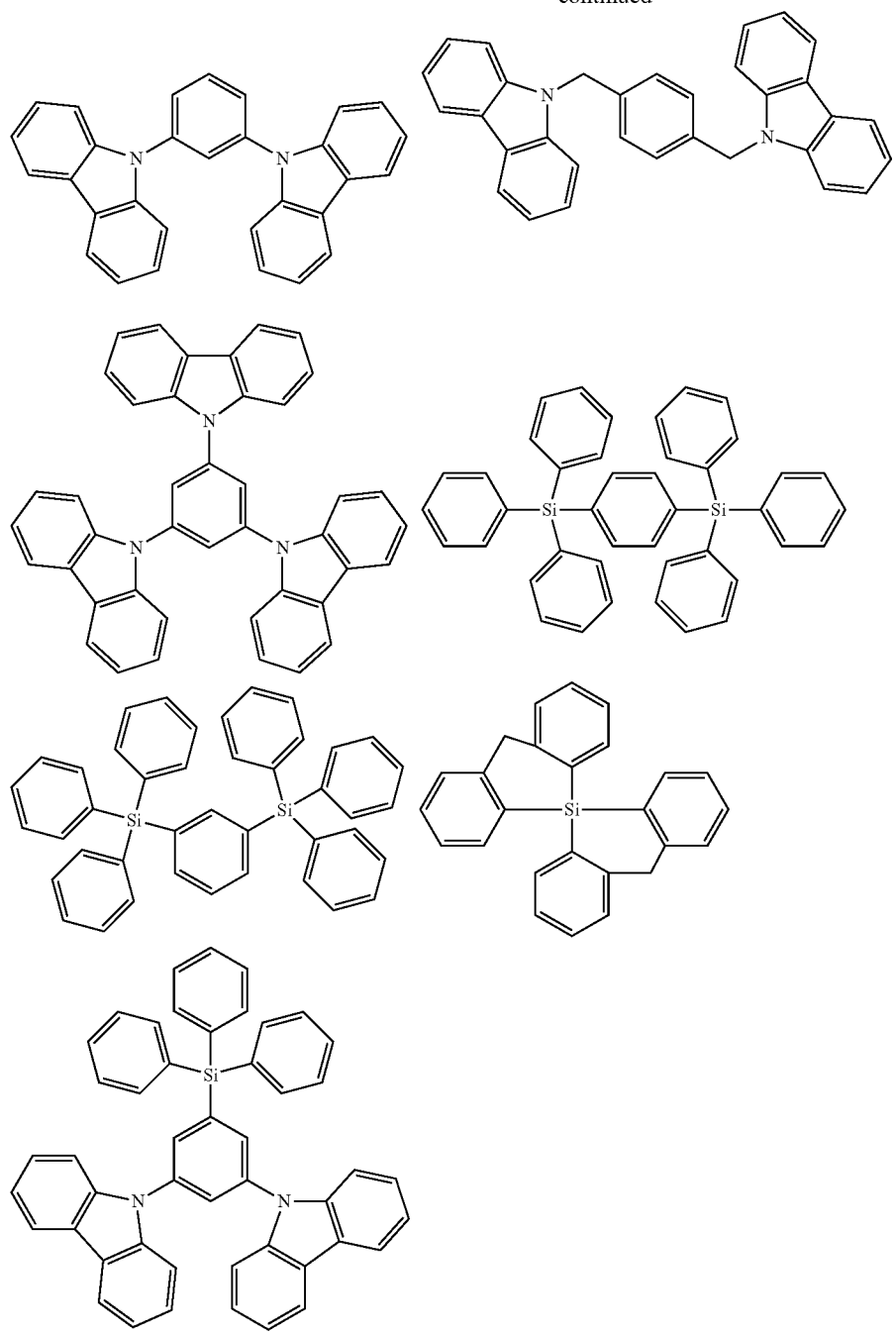
[Chemical Formula 131]
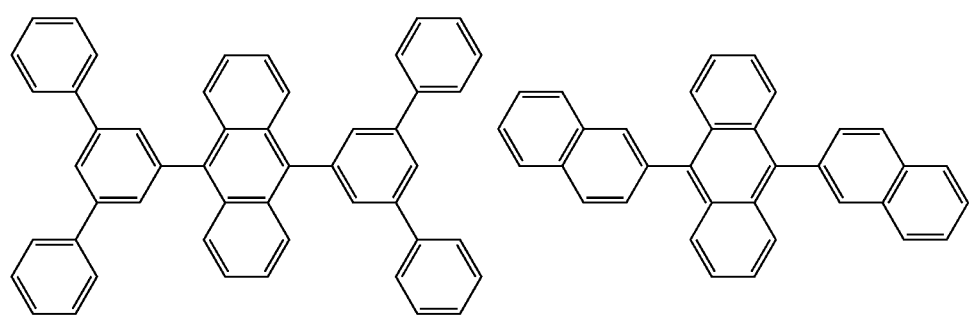

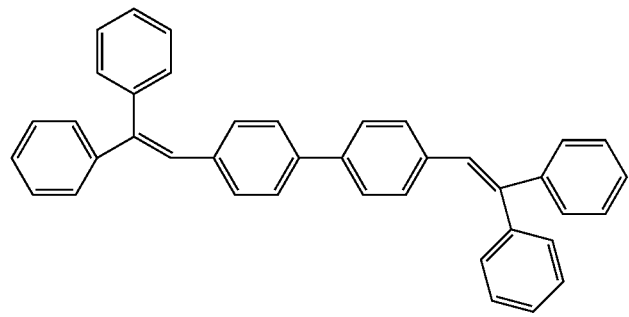
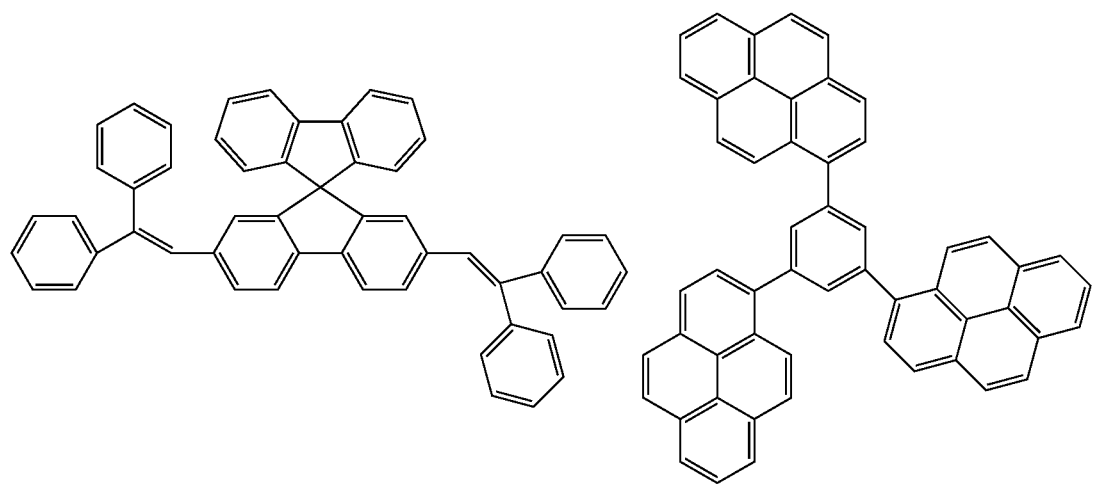
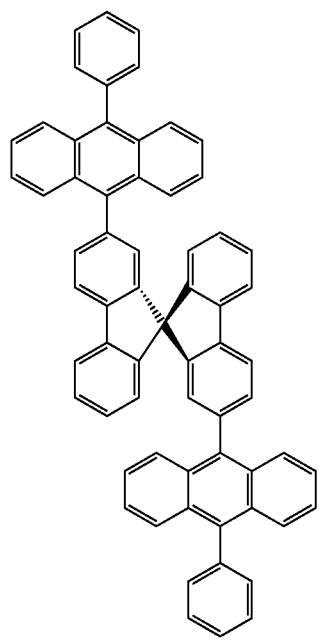

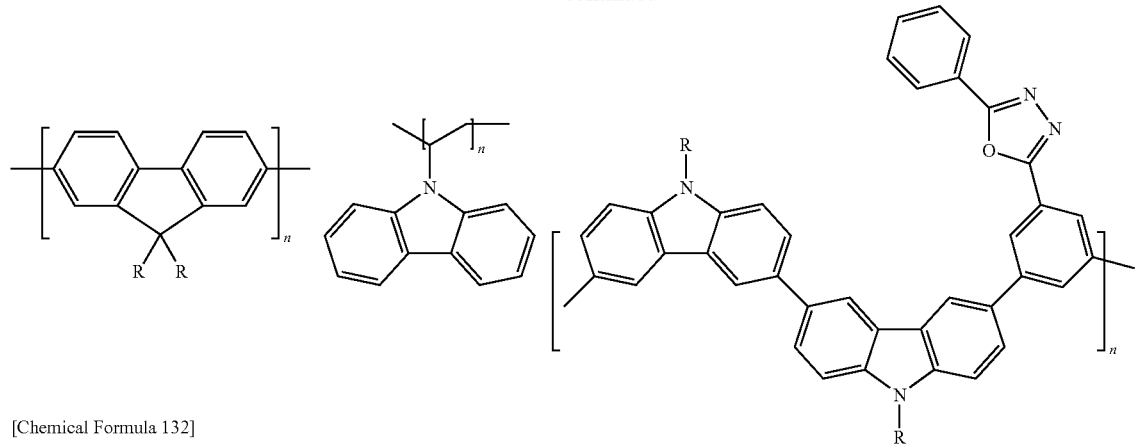
[Chemical Formula 132]
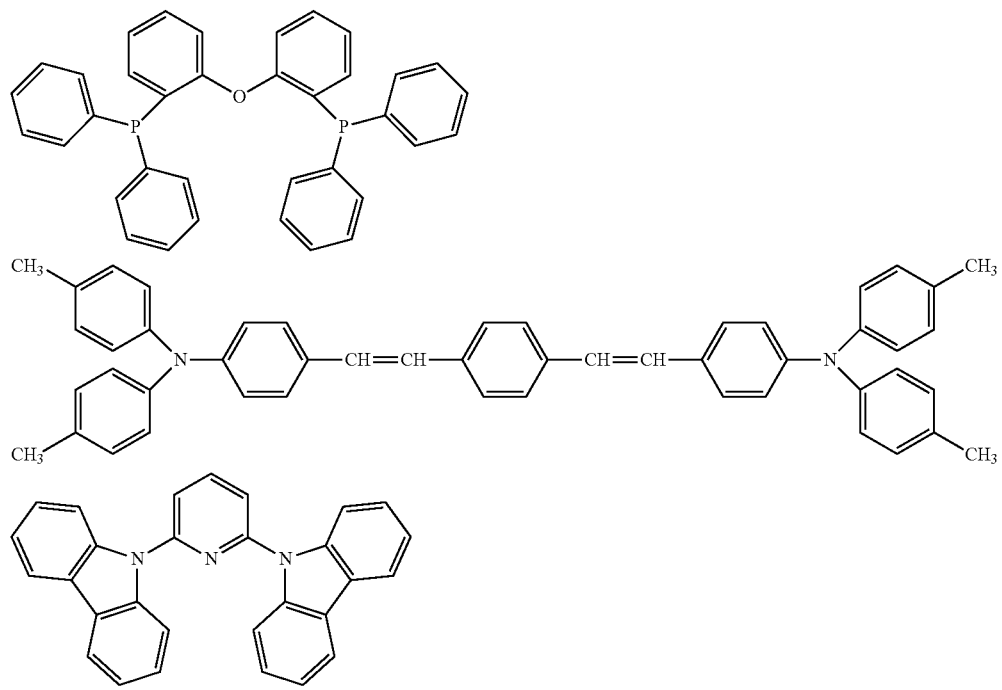
Preferred examples of a compound that may also be used as the material of the hole injection layer are shown below.
[Chemical Formula 133]
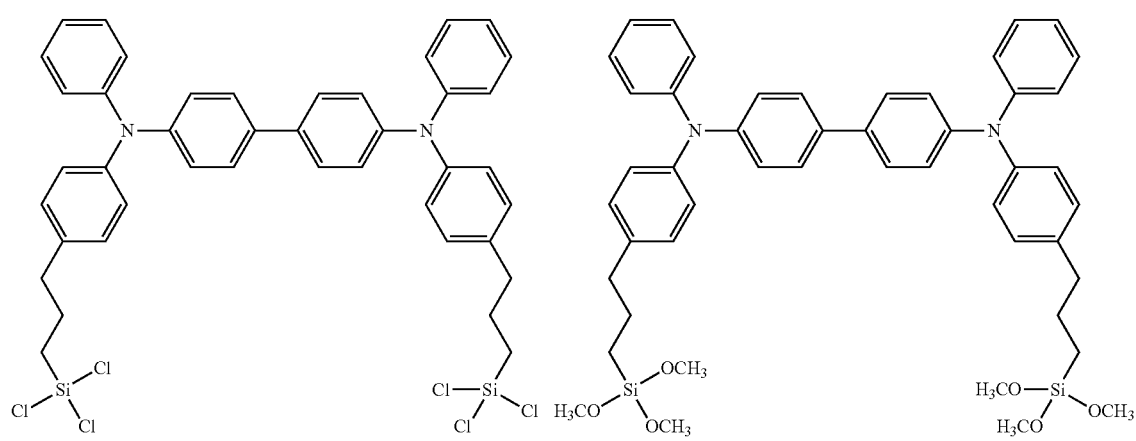

-continued
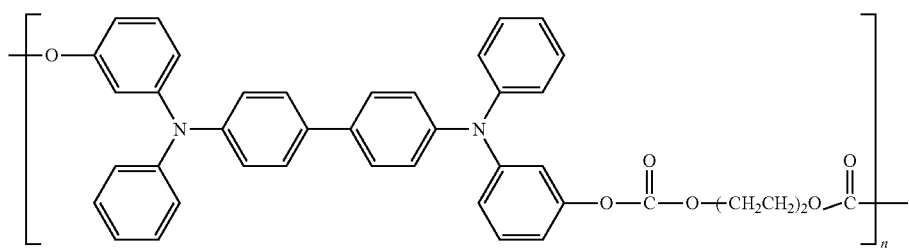
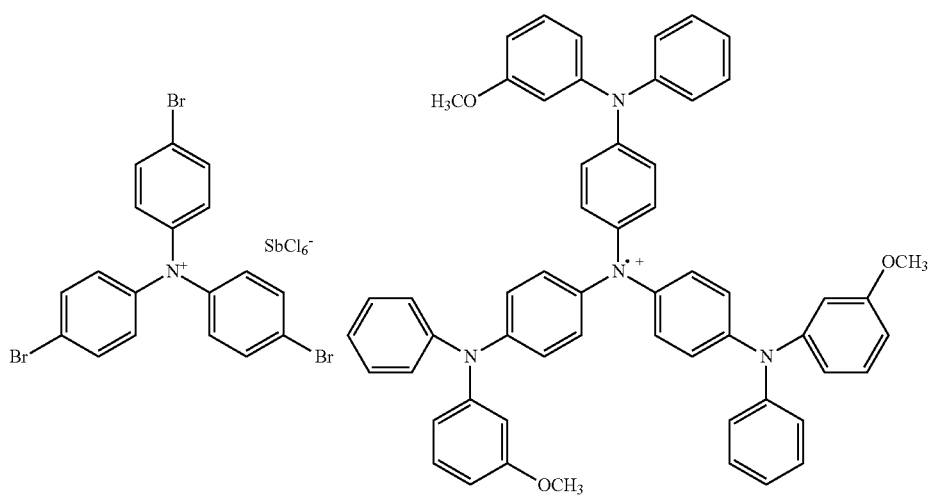
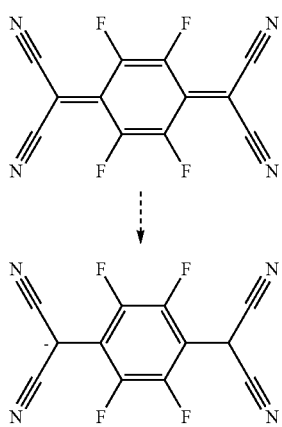
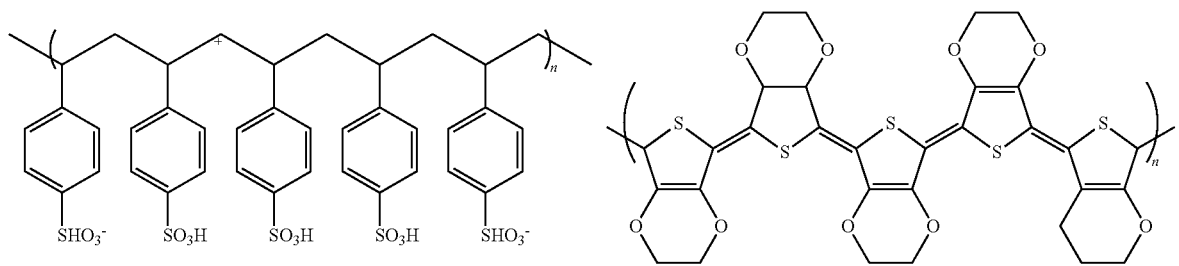

Preferred examples of a compound that may also be used as the material of the hole transport layer are shown below.
[Chemical Formula 134]
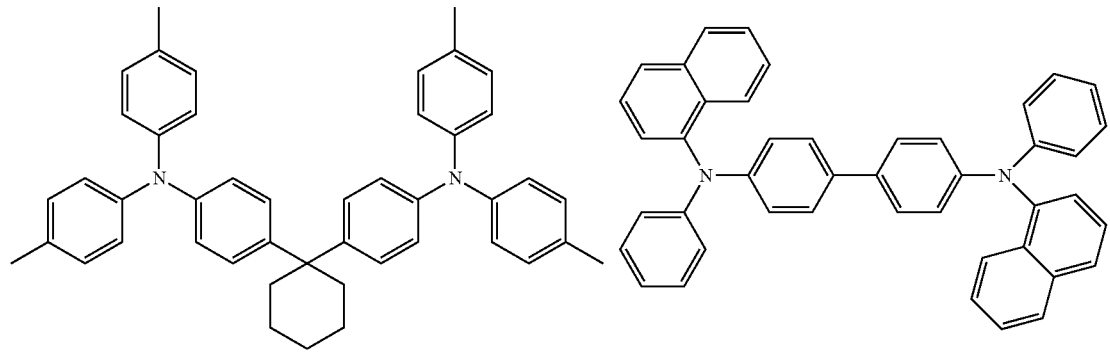
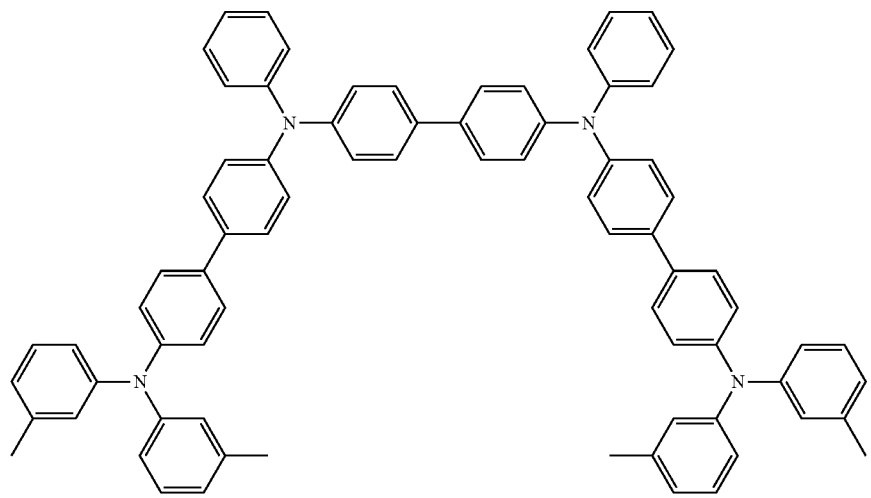
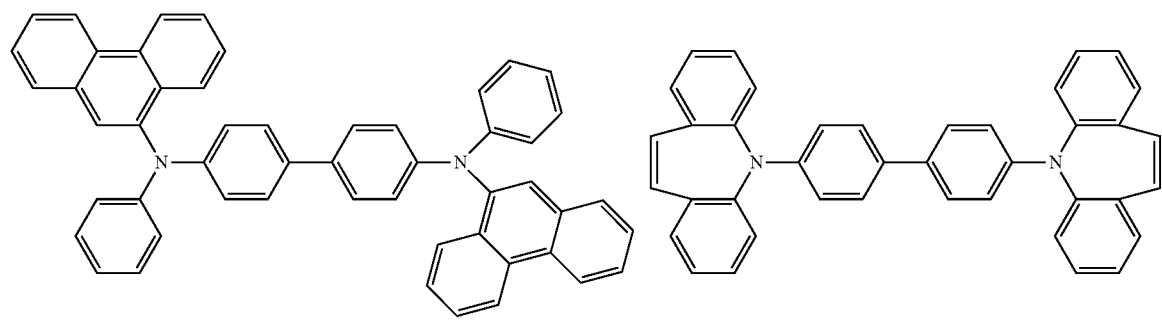

[Chemical Formula 135]
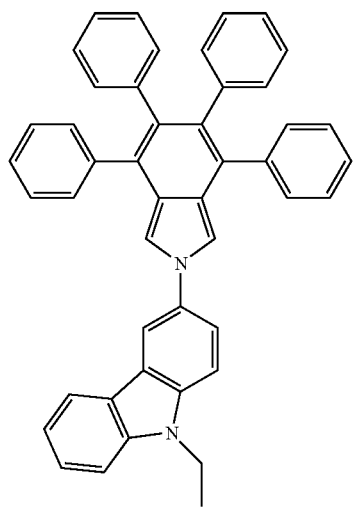
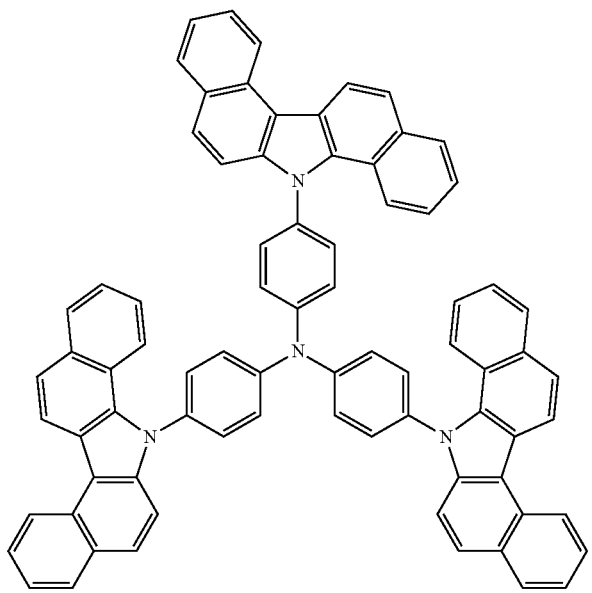
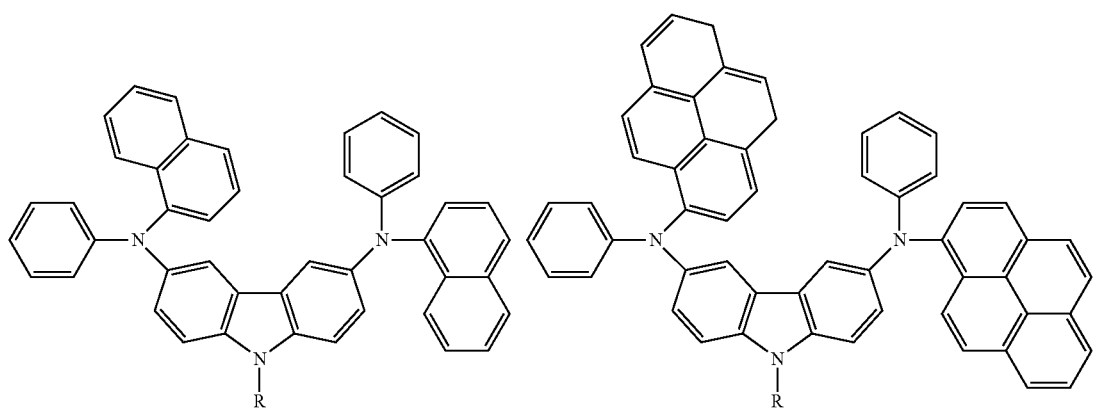
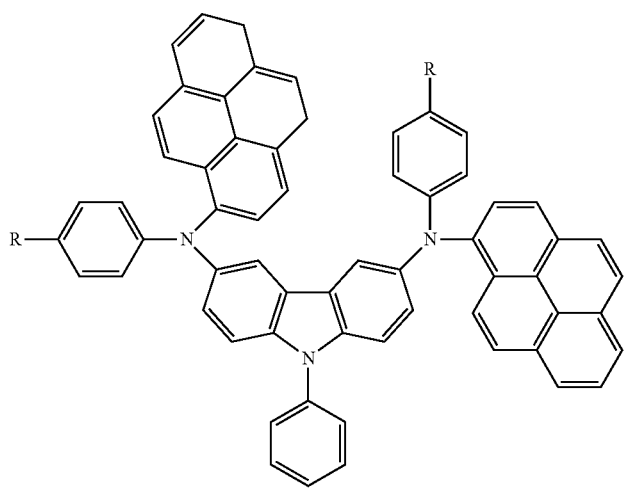

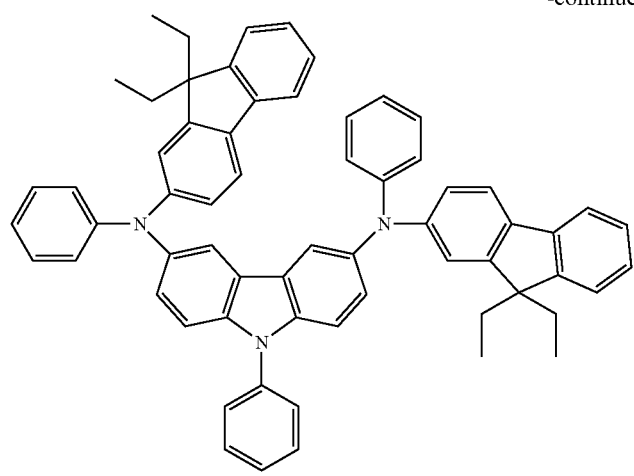
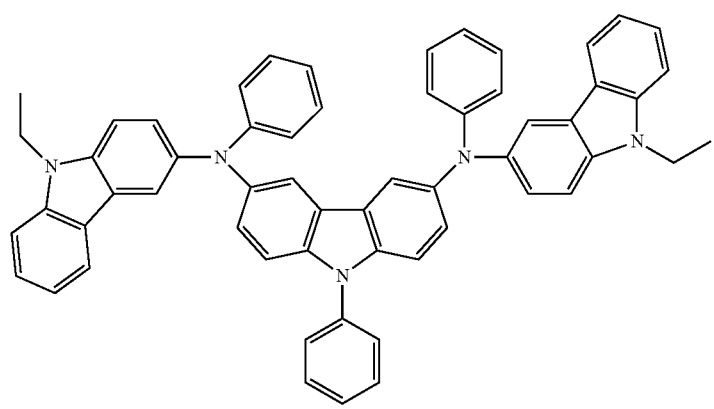
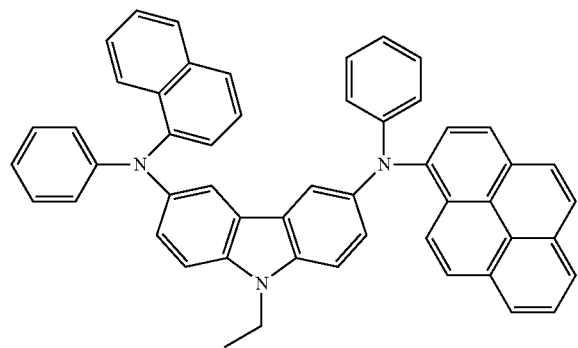

[Chemical Formula 136]
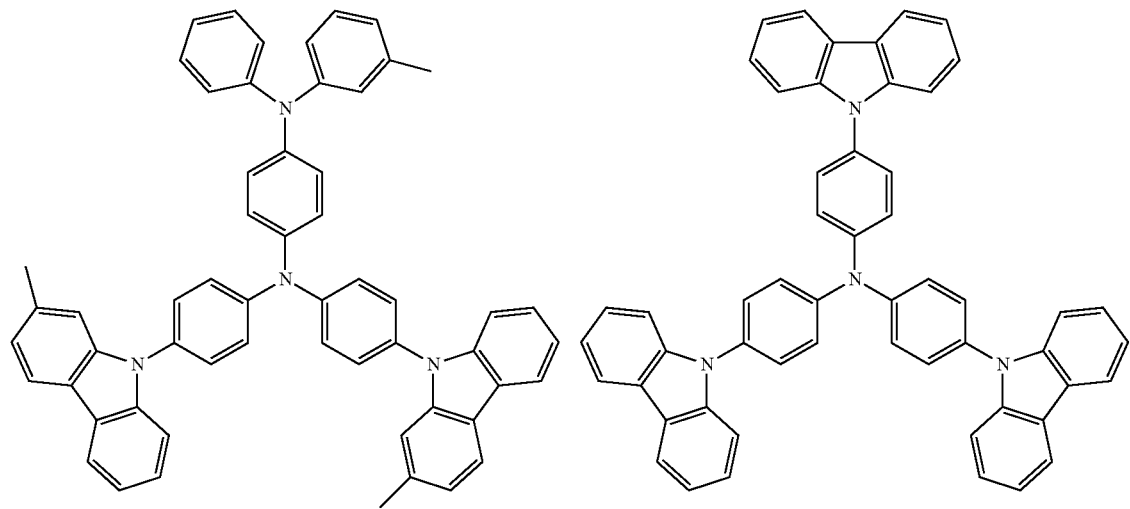
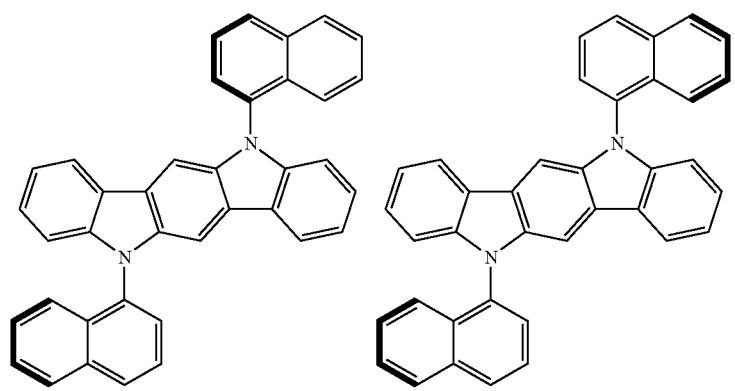
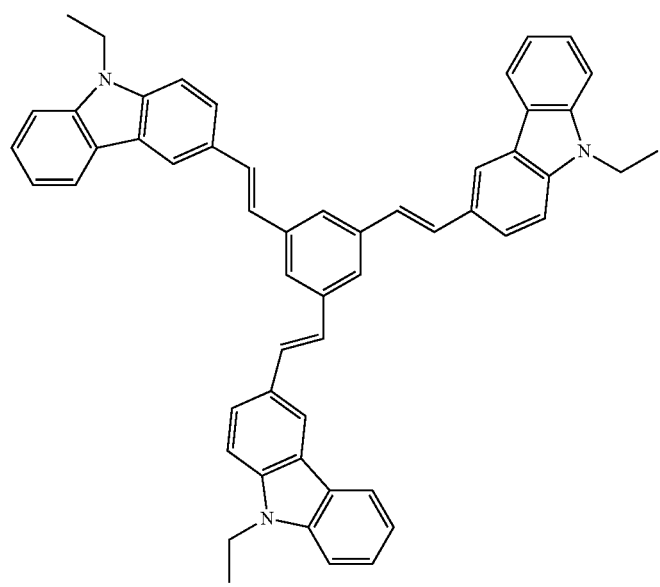

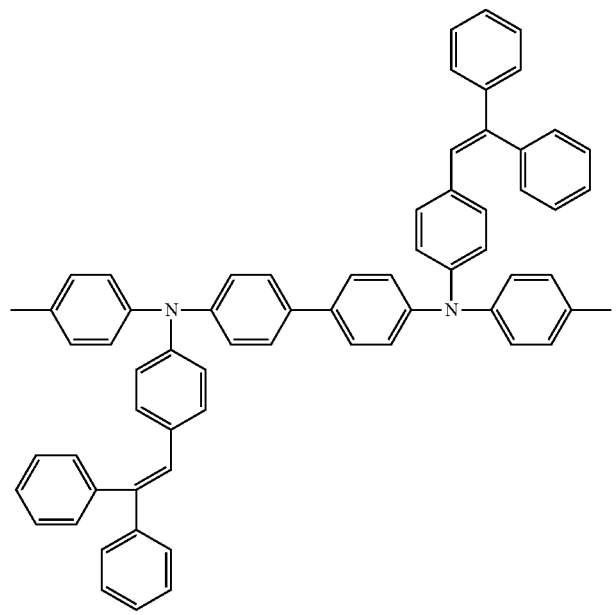
[Chemical Formula 137]
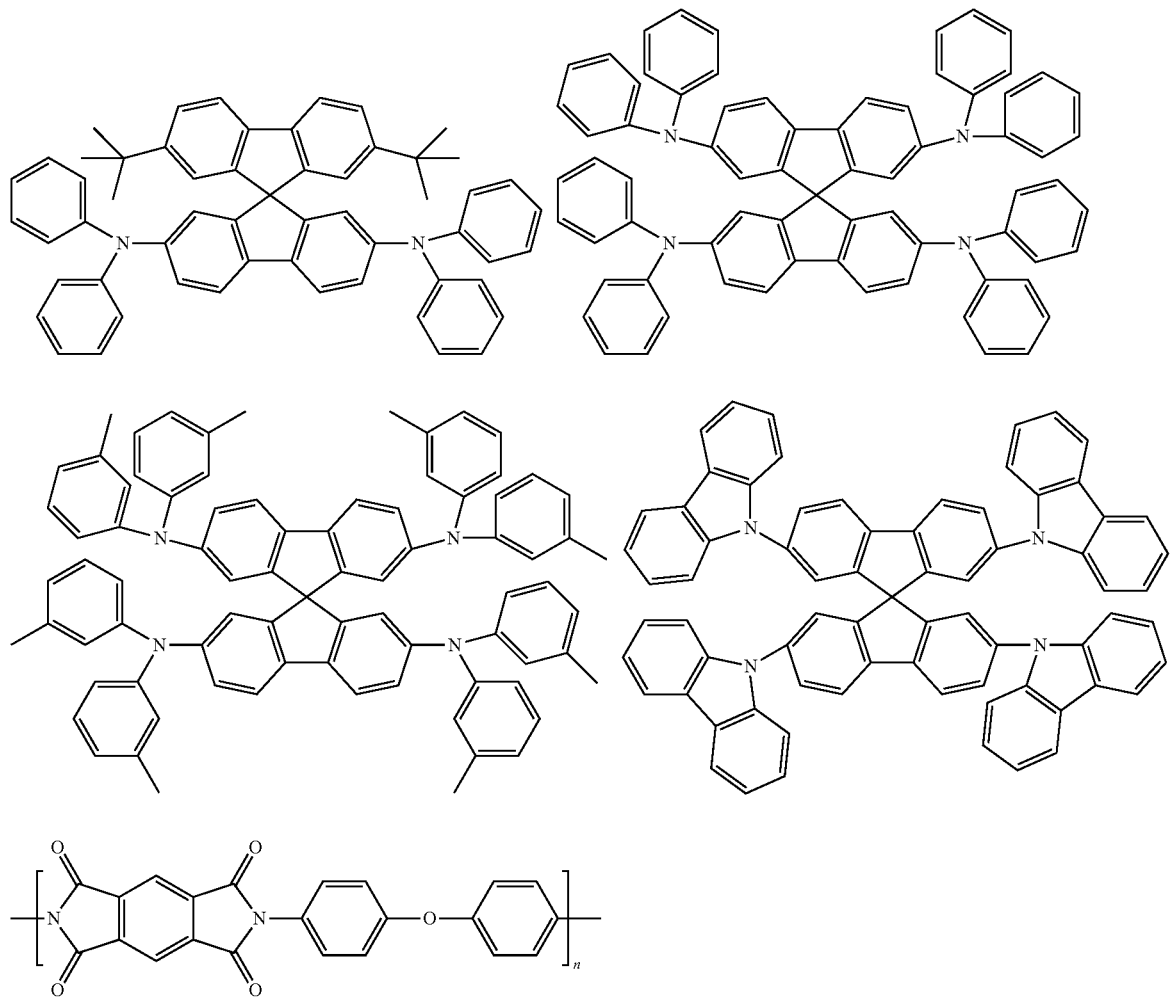

-continued
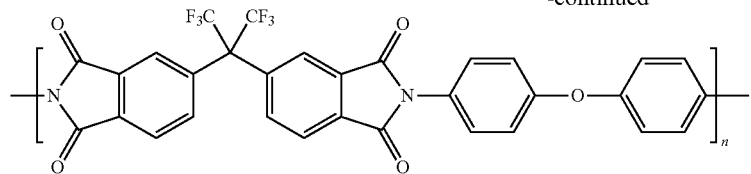
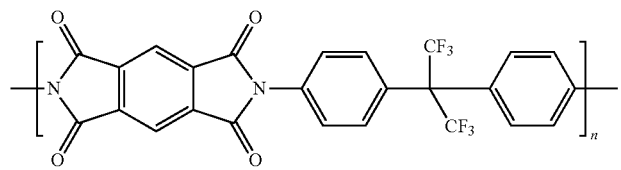
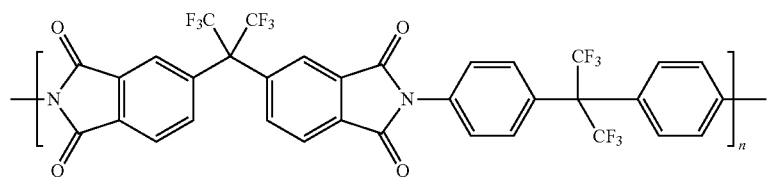
[Chemical Formula 138]
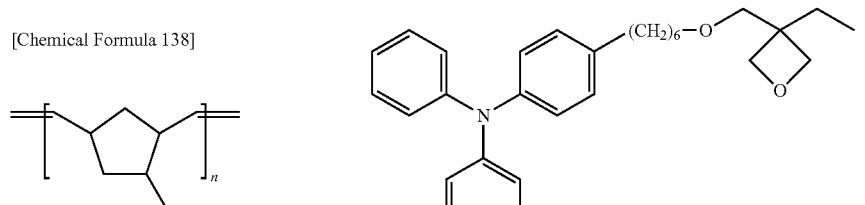
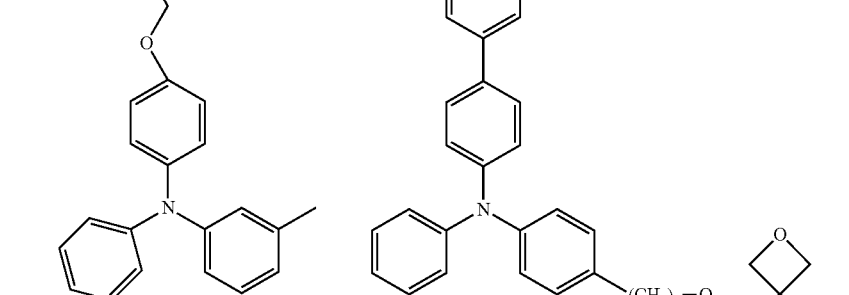
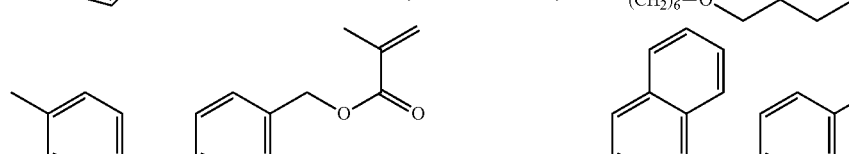
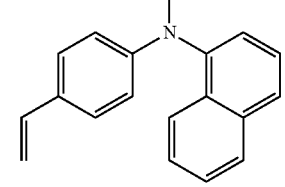

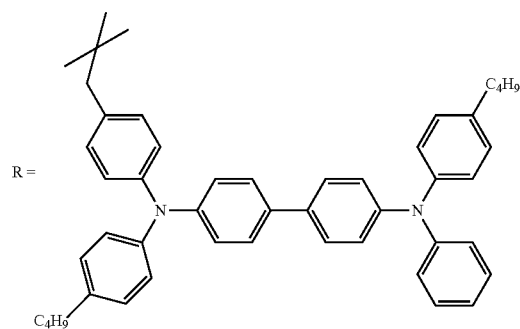
[Chemical Formula 139]
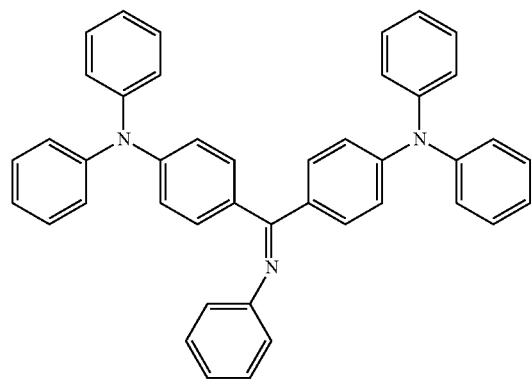
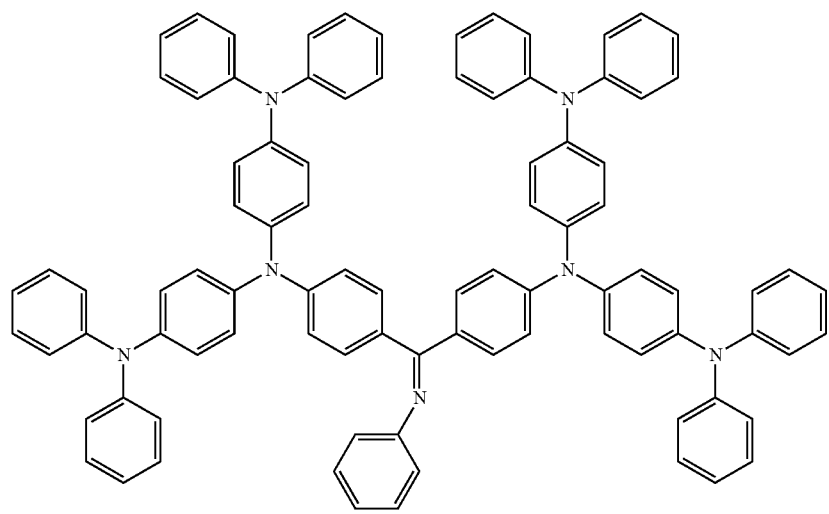

-continued
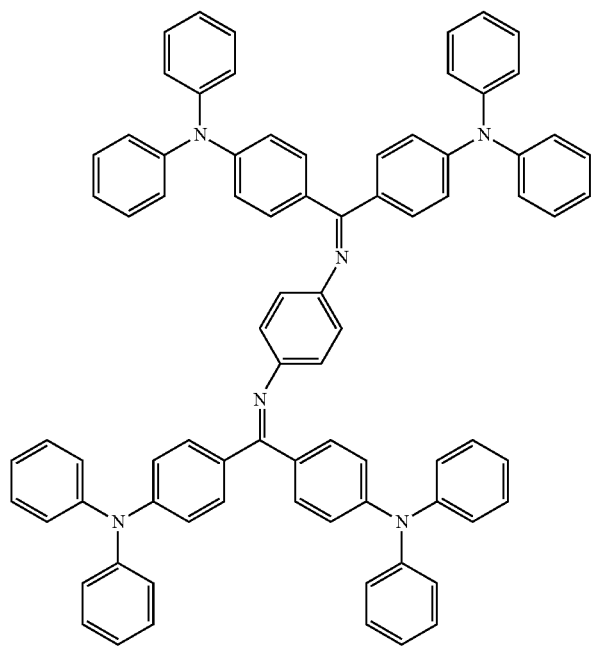
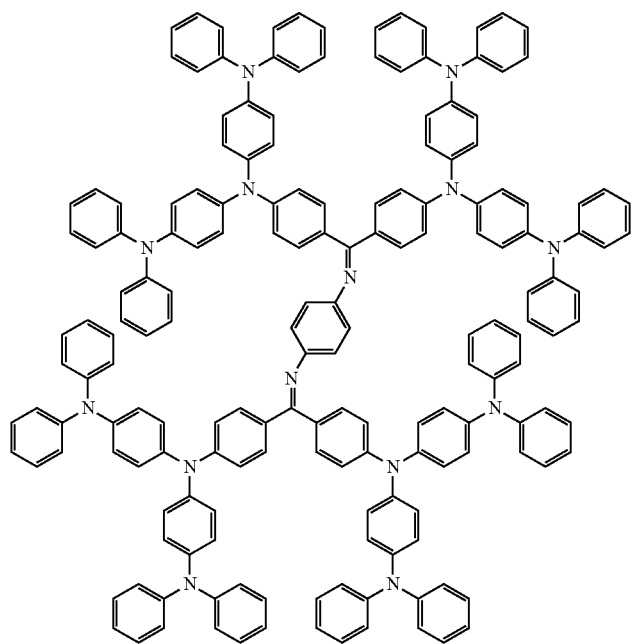

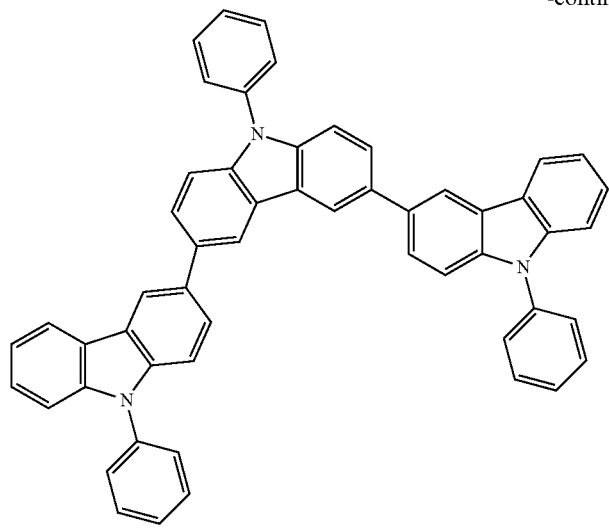
Preferred examples of a compound that may also be used as the material of the electron blocking layer are shown below.
Chemical Formula 140]
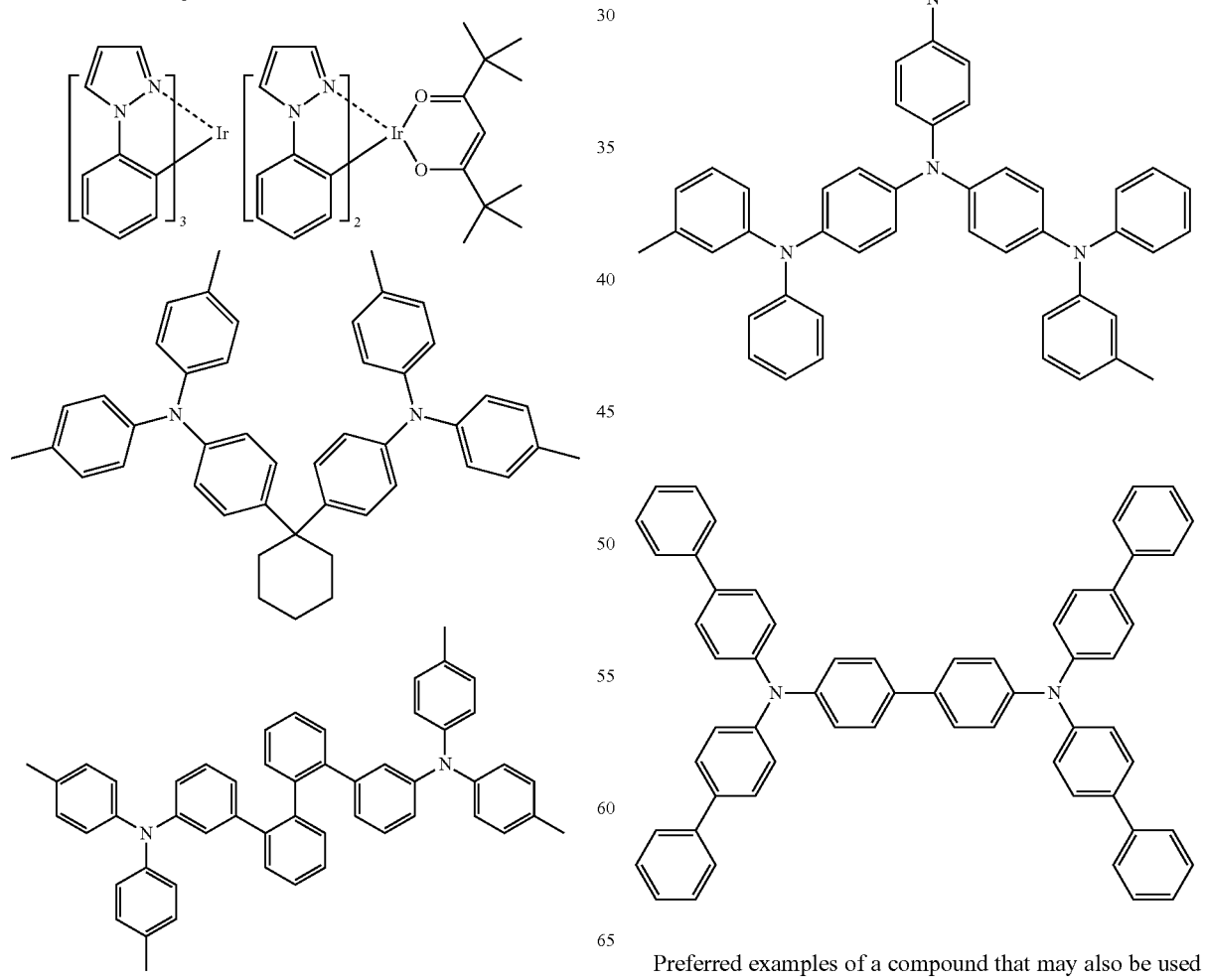
Preferred examples of a compound that may also be used as the material of the hole blocking layer are shown below.

[Chemical Formula 141]
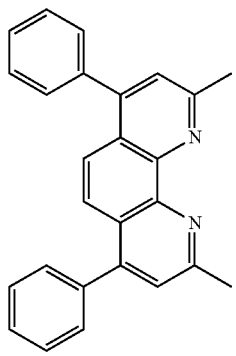
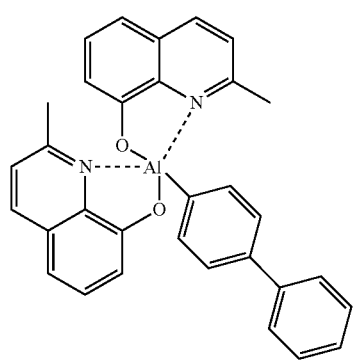
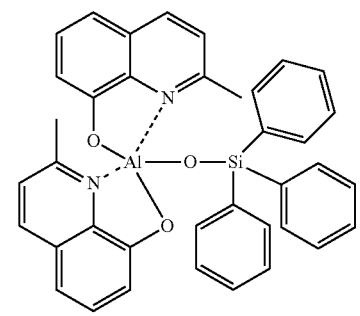
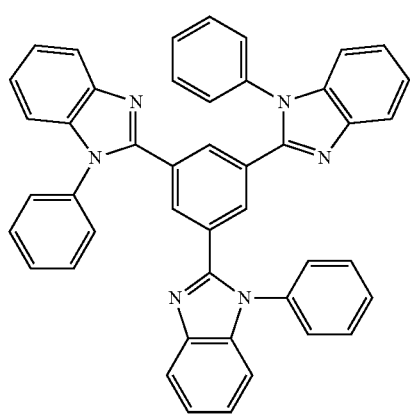
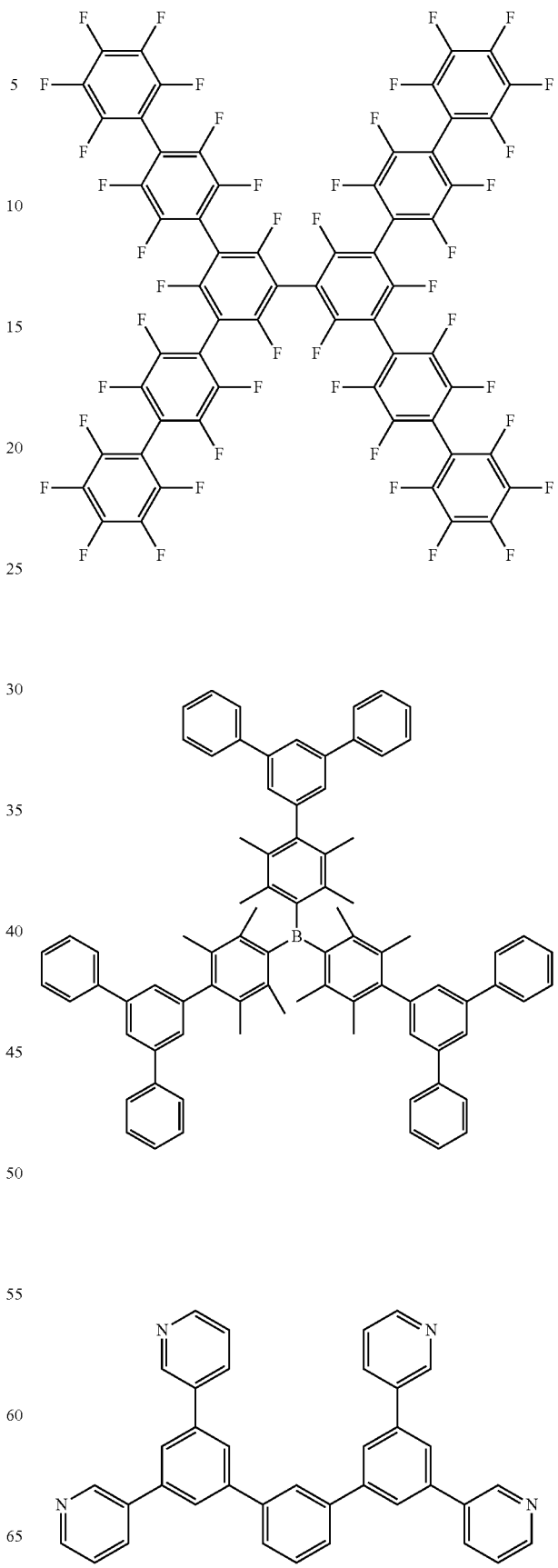

103
-continued
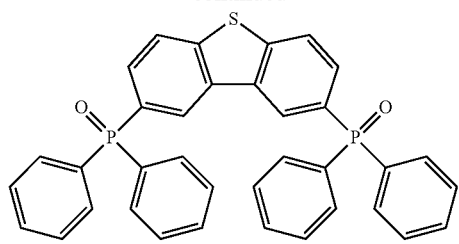
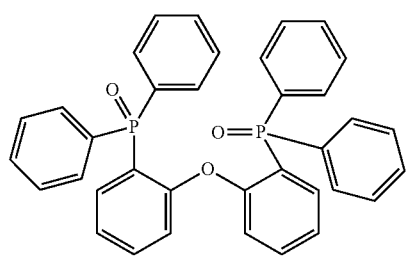
104
-continued
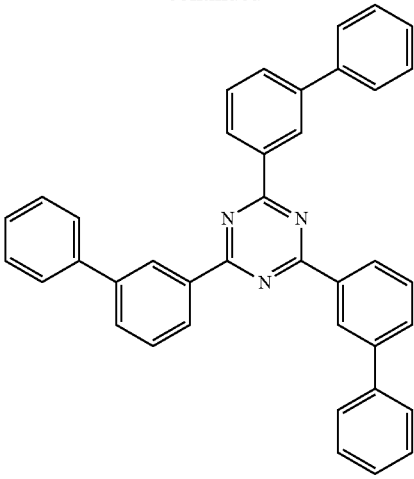
Preferred examples of a compound that may also be used as the material of the electron transport layer are shown below.
[Chemical Formula 142]
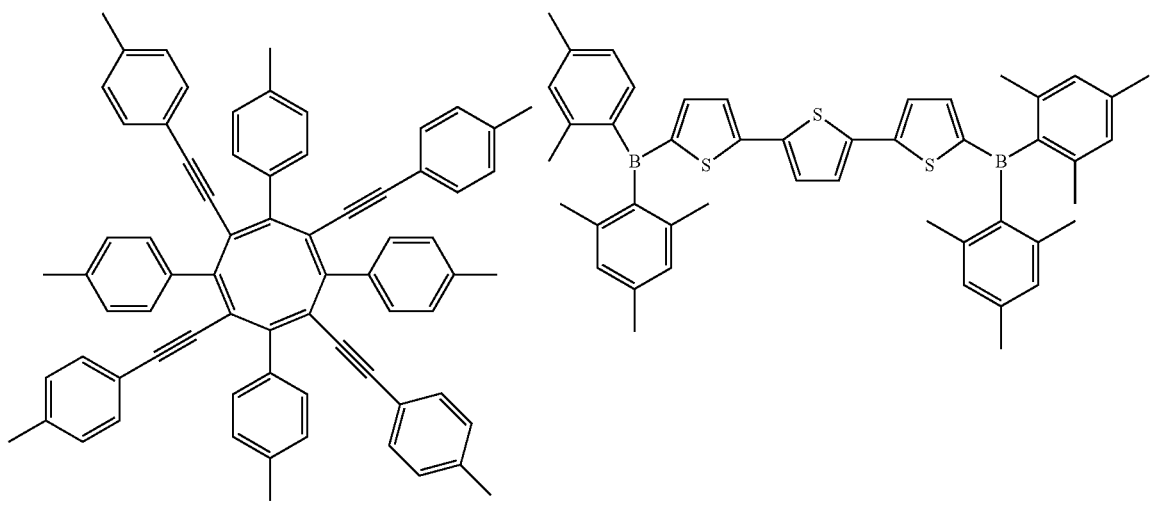
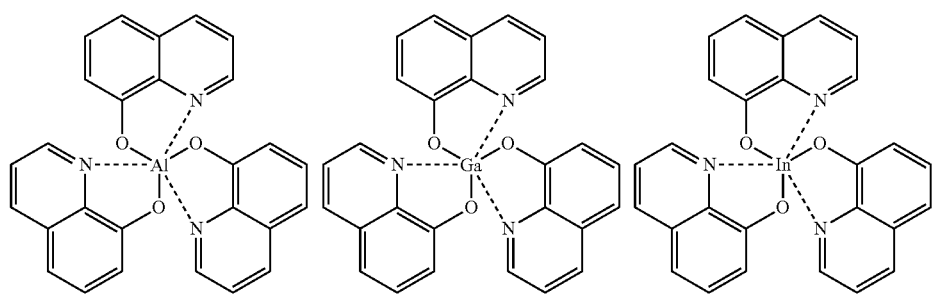

-continued
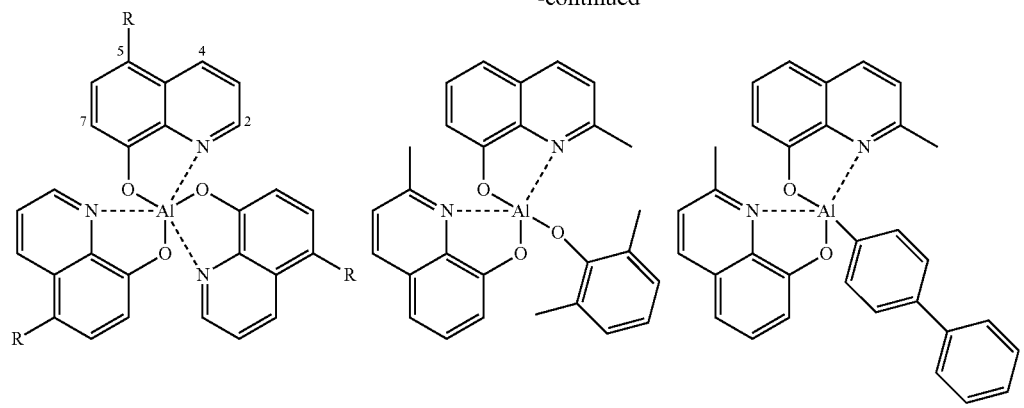
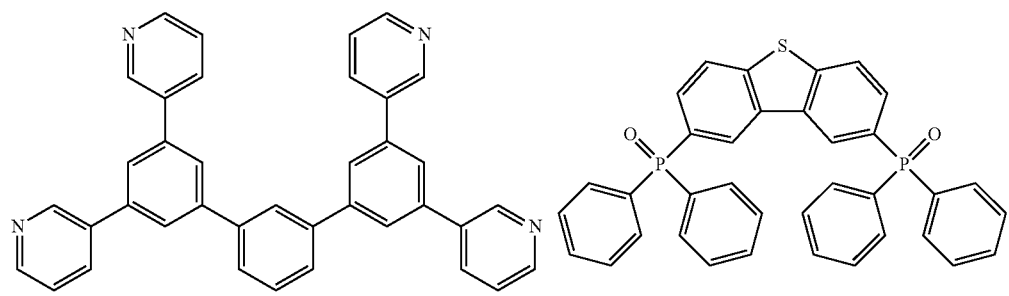
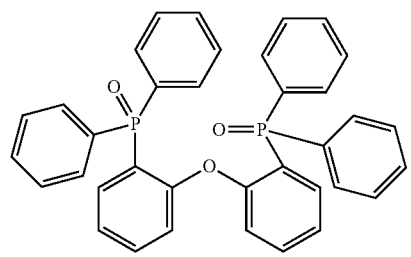
[Chemical Formula 143]
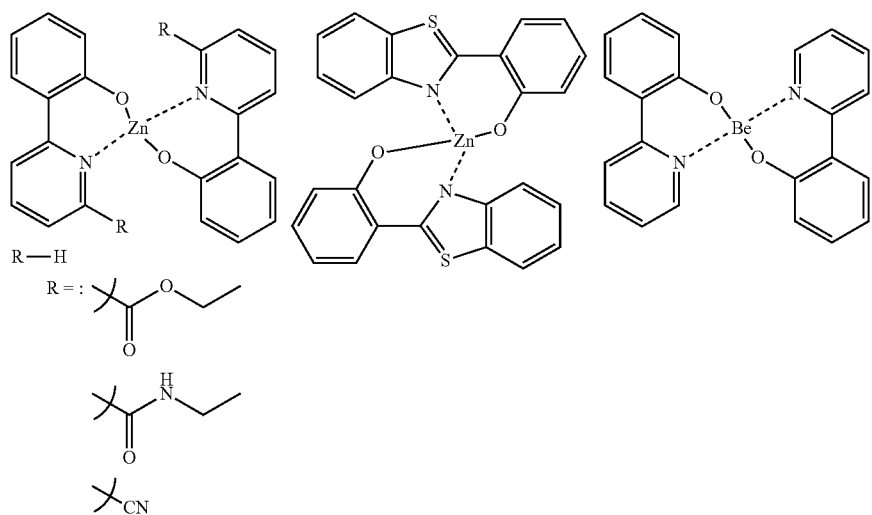

107
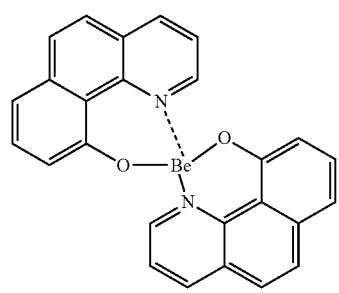
-continued
108
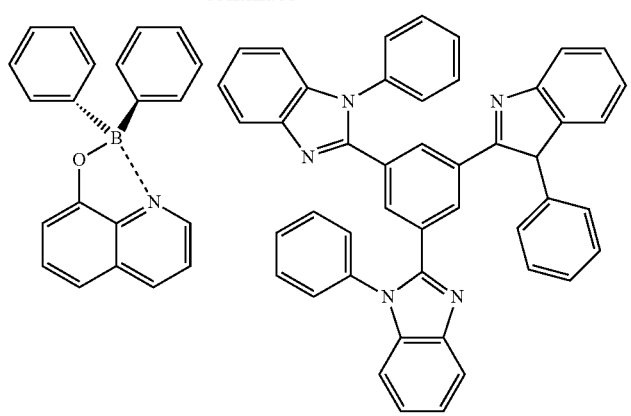
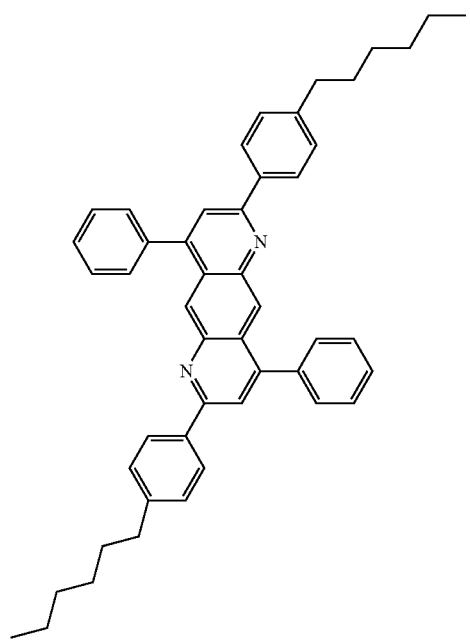
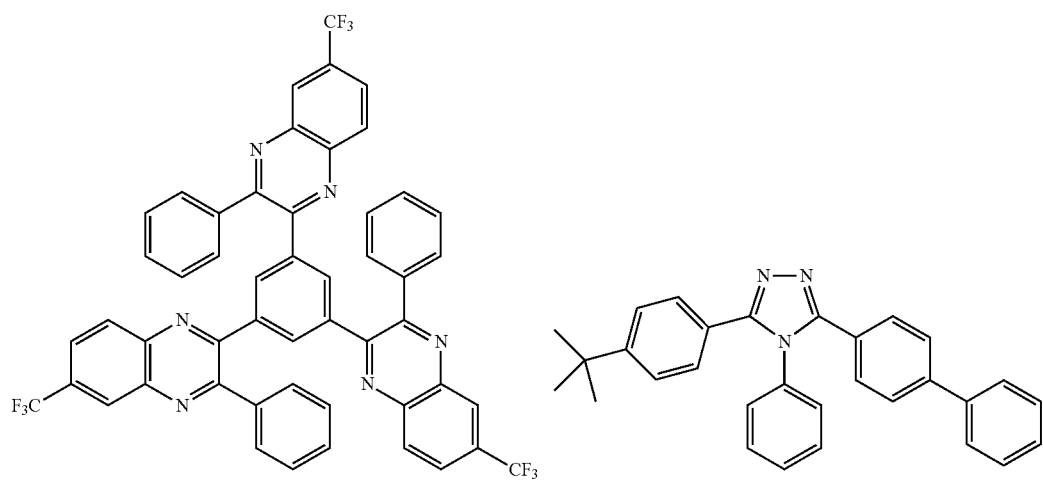

-continued
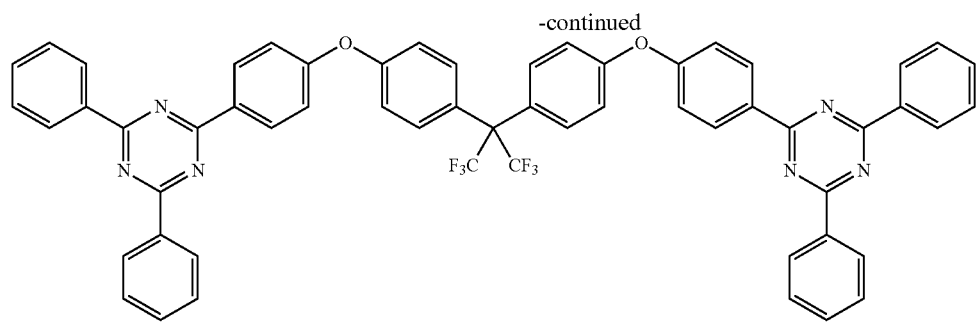
[Chemical Formula 144]
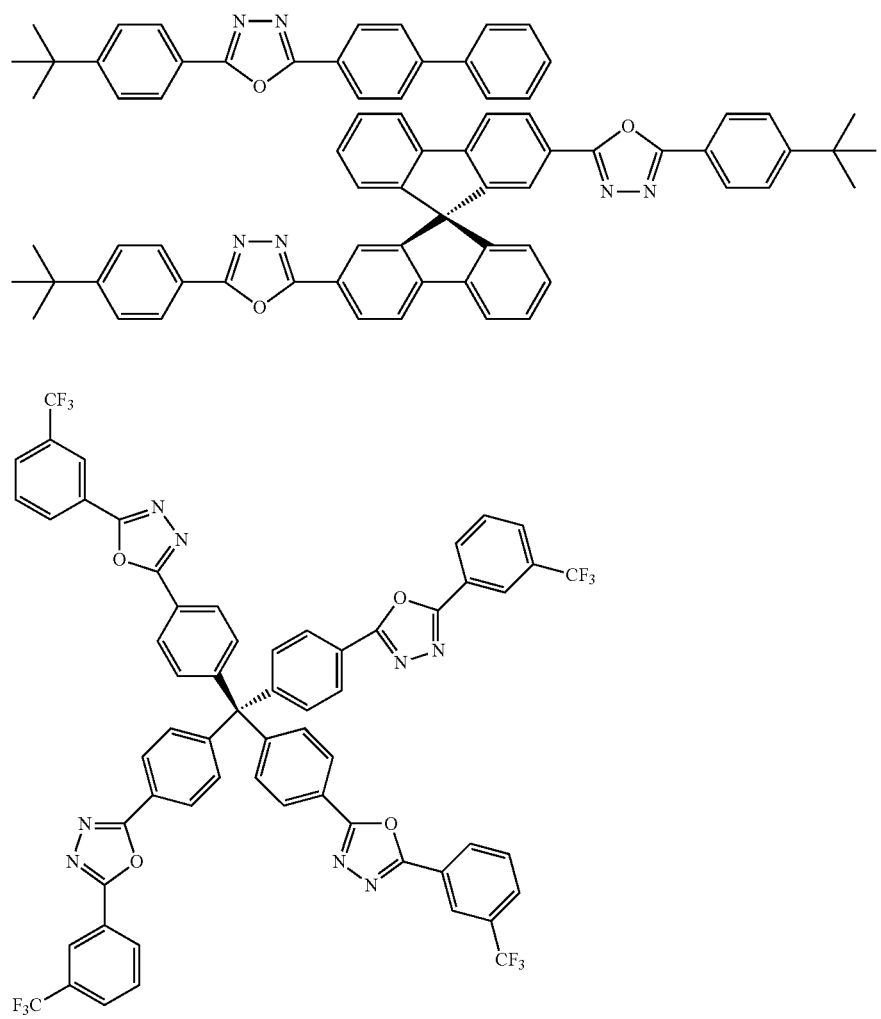
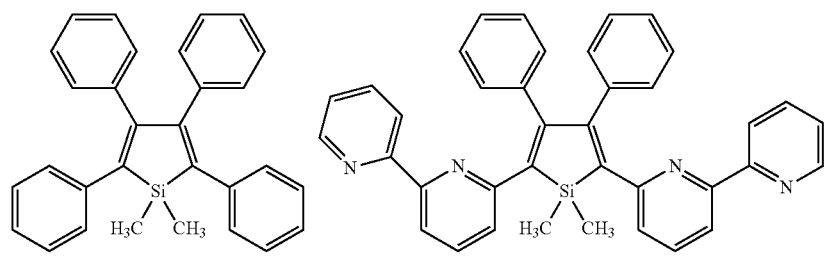

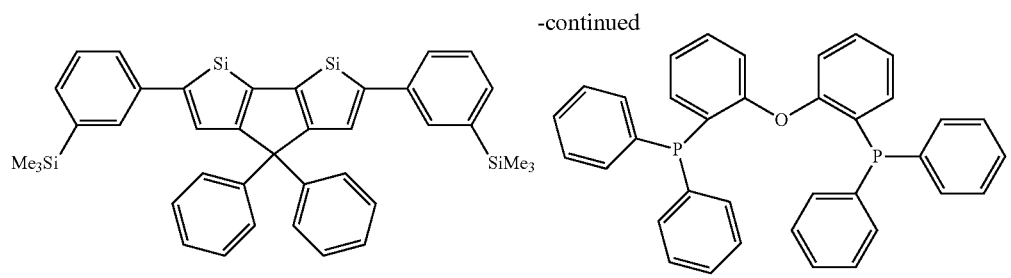

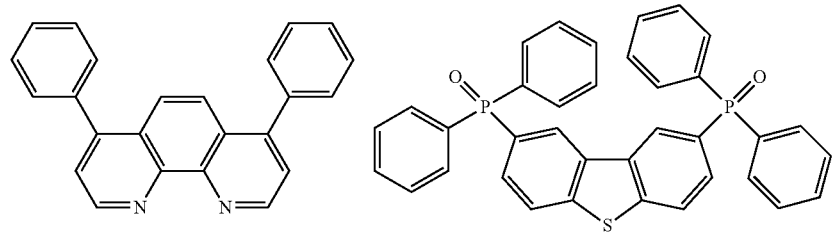

Preferred examples of a compound that may also be used as the material of the electron injection layer are shown below.

[Chemical Formula 145]

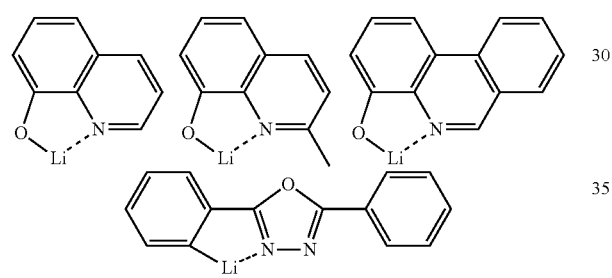

Preferred examples of a compound as a material that may be added are shown below. For example, the compound may be added as a stabilizing material.

[Chemical Formula 146]

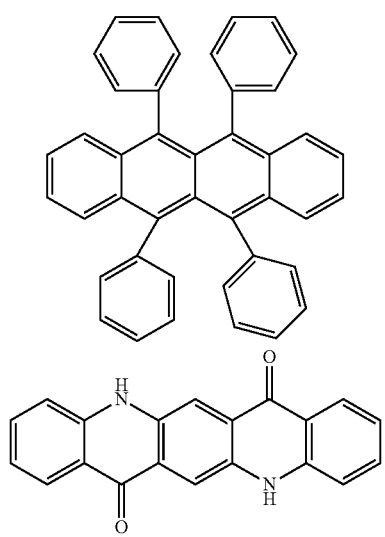

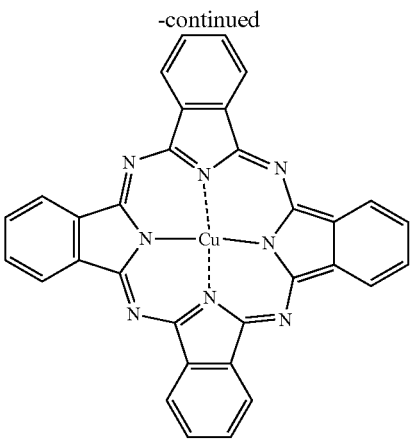

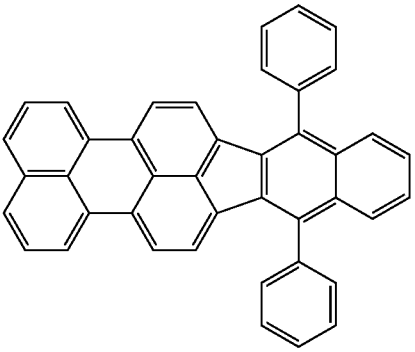

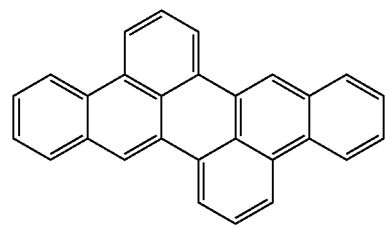

The following describes an embodiment of the present invention in more detail based on Examples. The present invention, however, is not restricted to the following Examples.

EXAMPLE 1

Synthesis of 6,11-bis(Phenoxazin-10-yl)-1,4,8,9-tetraazatriphenylene (Compound 1)

To a nitrogen-substituted reaction vessel were added 1,10-phenanthroline.monohydrate (22 g), disulfur dichloride (49 g), pyridine (30 mL), and 1-chlorobutane (300 mL), and bromine (57 g) was dropped while stirring the mixture. The mixture was then heated while being stirred, and heated to reflux for 6 h. A 18 M sodium hydroxide aqueous solution (300 mL), and chloroform (400 mL) were added after cooling the mixture to room temperature, and the mixture was stirred for 1 h at room temperature, and subjected to filtration using Celite as an auxiliary agent. Through extraction procedures, the chloroform layer was collected, and the solvent was evaporated after washing with saturated brine. The residue was then purified by column chromatography to obtain 3,8-dibromo-1,10-phenanthroline (yield 50%).

The product 3,8-dibromo-1,10-phenanthroline (10 g), and potassium bromide (5 g) were charged into a nitrogen-substituted reaction vessel, and a mixture of sulfuric acid and nitric acid was dropped over the course of 30 min. The mixture was then heated while being stirred, and heated to reflux for 1 h. After being cooled to room temperature, the reaction mixture was dropped into ice water, and a sodium hydroxide aqueous solution was carefully added until the solution pH turned 5. After extraction procedures with chloroform, the solution was dried over anhydrous magnesium sulfate, and the solvent was evaporated. The resulting residue was then washed with ethanol to obtain 3,8-dibromo-1,10-phenanthroline-5,6-dione (yield 98%).

The product 3,8-dibromo-1,10-phenanthroline-5,6-dione (5 g), and THF (50 mL) were added into a nitrogen-substituted reaction vessel, and ethylenediamine (10 mL) was added. The mixture was stirred at room temperature for 1 h, and the solvent of the reaction mixture was evaporated. The resulting residue was washed with methanol. The mixture was heated after adding chloroform (100 mL) and silica gel (10 g), and heated to reflux for 18 h while being stirred. The mixture was then cooled to room temperature, and the insolubles were removed by filtration. After evaporating the solvent, the resulting crude product was washed with methanol to obtain 6,11-dibromo-1,4,8,9-tetraazatriphenylene (yield 35%).

The product 6,11-dibromo-1,4,8,9-tetraazatriphenylene (1.0 g), phenoxazine (1.5 g), sodium-tert-butoxide (0.6 g), tri-tert-butylphosphine (0.1 g), and toluene (80 mL) were added into a nitrogen-substituted reaction vessel, and the reaction mixture was deaerated while being stirred. The mixture was heated after adding a tris(dibenzylideneacetone) palladium.chloroform inclusion compound (0.07 g), and heated to reflux for 10 h while being stirred. After allowing the mixture to cool, methanol was added, and the precipitated crude product was collected by filtration. The precipitate was then purified by silica gel column chromatography to obtain a yellow powder of 6,11-bis(phenoxazin-10-yl)-1,4,8,9-tetraazatriphenylene (Compound 1; yield 30%).

The structure of the yellow powder product was identified by NMR. The $^1$H-NMR measurement result is shown in FIG. 1.

$^1$H-NMR (DMSO-$d_6$) detected 22 hydrogen signals, as follows.

δ (ppm)=9.63 (2H), 9.32 (2H), 9.03 (2H), 6.66-6.57 (12H), 6.07 (4H).

EXAMPLE 2

Synthesis of 6,11-bis{3-(Diphenylamino)carbazol-9-yl}-1,4,8,9-tetraazatriphenylene (Compound 35)

The 6,11-dibromo-1,4,8,9-tetraazatriphenylene (1.0 g) synthesized in Example 1, 3-(diphenylamino)carbazole (2.0 g), sodium-tert-butoxide (0.6 g), tri-tert-butylphosphine (0.1 g), and xylene (60 mL) were added into a nitrogen-substituted reaction vessel. The reaction mixture was then deaerated while being stirred. The mixture was heated after adding a tris(dibenzylideneacetone)palladium.chloroform inclusion compound (0.07 g), and heated to reflux for 5 h while being stirred. After allowing the mixture to cool, methanol was added, and the precipitated crude product was collected by filtration. The precipitate was then purified by silica gel column chromatography to obtain a yellowish white powder of 6,11-bis{3-(diphenylamino)carbazol-9-yl}-1,4,8,9-tetraazat riphenylene (Compound 35; yield 10%).

Figure 2:
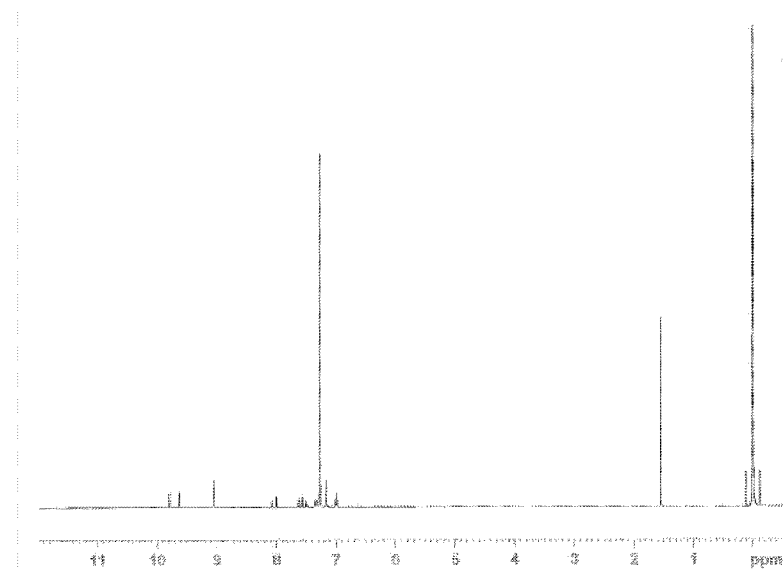
FIG. 2 is a $^1$H-NMR chart of the compound of Example 2 of the present invention (Compound 35).

The structure of the yellowish white powder product was identified by NMR. The $^1$H-NMR measurement result is shown in FIG. 2.

$^1$H-NMR (DMSO-$d_6$) detected 40 hydrogen signals, as follows.

δ (ppm)=9.79 (2H), 9.63 (2H), 9.05 (2H), 8.07 (2H), 8.00 (2H), 7.62 (2H), 7.57 (2H), 7.49 (2H), 7.39-7.13 (20H), 7.00 (4H).

EXAMPLE 3

Synthesis of 6,11-bis(Diphenylamino)-1,4,8,9-tetraazatriphenylene (Compound 4)

The 6,11-dibromo-1,4,8,9-tetraazatriphenylene (1.0 g) synthesized in Example 1, diphenylamine (1.2 g), sodium-tert-butoxide (0.6 g), tri-tert-butylphosphine (0.1 g), and xylene (60 mL) were added into a nitrogen-substituted reaction vessel. The reaction mixture was then deaerated while being stirred. The mixture was heated after adding a tris(dibenzylideneacetone)palladium.chloroform inclusion compound (0.07 g), and heated to reflux for 5 h while being stirred. After allowing the mixture to cool, methanol was added, and the precipitated crude product was collected by filtration. The precipitate was then purified by silica gel column chromatography to obtain a white powder of 6,11-bis(diphenylamino)-1,4,8,9-tetraazatriphenylene (Compound 4; yield 40%).

Figure 3:
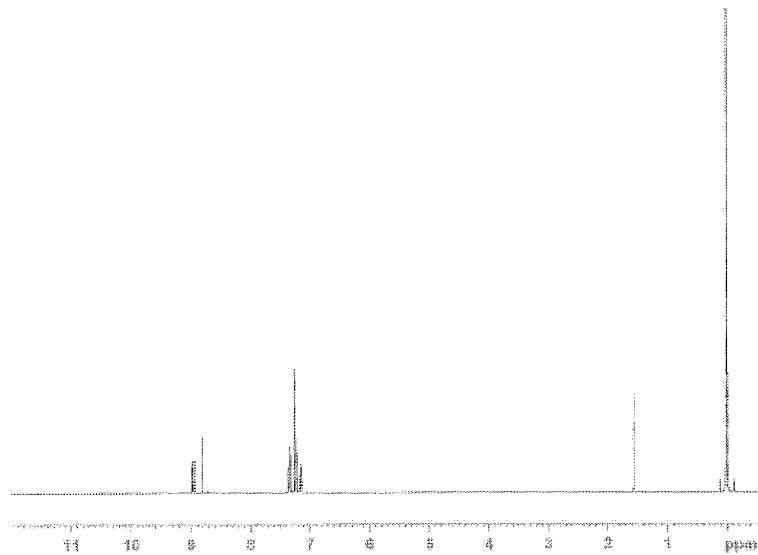
FIG. 3 is a $^1$H-NMR chart of the compound of Example 3 of the present invention (Compound 4).

The structure of the white powder product was identified by NMR. The $^1$H-NMR measurement result is shown in FIG. 3.

$^1$H-NMR (DMSO-$d_6$) detected 26 hydrogen signals, as follows.

δ (ppm)=8.97 (2H), 8.94 (2H), 8.79 (2H), 7.34 (8H), 7.23 (8H), 7.14 (4H).

EXAMPLE 4

Synthesis of 6,11-bis(Carbazol-9-yl)-1,4,8,9-tetraazatriphenylene (Compound 3)

The 6,11-dibromo-1,4,8,9-tetraazatriphenylene (1.0 g) synthesized in Example 1, carbazole (1.2 g), sodium-tert-butoxide (0.6 g), tri-tert-butylphosphine (0.1 g), and xylene (60 mL) were added into a nitrogen-substituted reaction vessel. The reaction mixture was then deaerated while being stirred. The mixture was heated after adding a tris(dibenzylideneacetone)palladium.chloroform inclusion compound (0.07 g), and heated to reflux for 5 h while being stirred. After allowing the mixture to cool, methanol was added, and the precipitated crude product was collected by filtration. The precipitate was then purified by silica gel column chromatography to obtain a yellowish white powder of 6,11-bis(carbazol-9-yl)-1,4,8,9-tetraazatriphenylene (Compound 3; yield 36%).

Figure 4:
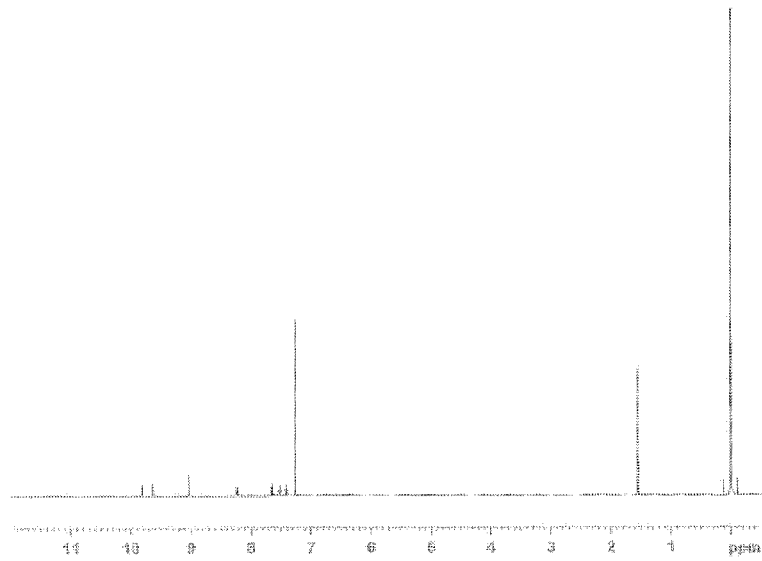
FIG. 4 is a $^1$H-NMR chart of the compound of Example 4 of the present invention (Compound 3).

The structure of the yellowish white powder product was identified by NMR. The $^1$H-NMR measurement result is shown in FIG. 4.

$^1$H-NMR (DMSO-$d_6$) detected 22 hydrogen signals, as follows.

δ (ppm)=9.81 (2H), 9.63 (2H), 9.05 (2H), 8.23 (4H), 7.65 (4H), 7.52 (4H), 7.41 (4H).

EXAMPLE 5

A 100 nm-thick vapor-deposited film was fabricated on an ITO substrate using the compounds of Examples 1 and 3 (Compounds 1 and 4). The work function was measured using an atmosphere photoelectron spectrometer (AC-3 produced by Riken Keiki Co., Ltd.).

| | Work function |
|---|---|
| Compound of Example 1 of the present invention | 5.70 eV |
| Compound of Example 3 of the present invention | 5.60 eV |

As demonstrated above, the compounds of Examples 1 and 3 (Compounds 1 and 4) of the present invention have larger work function values than the work function, 5.4 eV, of common hole transport materials such as NPD and TPD, and are highly capable of blocking holes.

EXAMPLE 6

A $10^{-5}$ mol/L toluene solution was prepared for the compound of Example 1 of the present invention (Compound 1). This toluene solution was irradiated with ultraviolet light at 300 K while being aerated with nitrogen, and fluorescence having a peak wavelength of 587 nm was observed.

The time-resolved spectrum of the above toluene solution was also measured before and after the aeration with nitrogen, using a compact fluorescence lifetime spectrometer (Model Quantaurus-tau produced by Hamamatsu Photonics K.K.). The emission lifetime was observed as fluorescence of 0.02 μs, and delayed fluorescence of 1.08 μs.

The photoluminescence (hereinafter, "PL") quantum efficiency of the above toluene solution was also measured before and after the aeration with nitrogen, using an absolute PL quantum yield measurement device (Quantaurus-QY produced by Hamamatsu Photonics K.K.) at 300 K. The PL quantum efficiency was 2.9% before the aeration with nitrogen, and 9.1% after the aeration with nitrogen.

EXAMPLE 7

A $10^{-5}$ mol/L toluene solution was prepared for the compound of Example 2 of the present invention (Compound 35), instead of the compound of Example 1 of the present invention (Compound 1) used in Example 6, and the characteristics of the toluene solution were evaluated in the same manner as in Example 6. As a result, fluorescence having a peak wavelength of 584 nm was observed. The emission lifetime was observed as fluorescence of 4.82 ns, and delayed fluorescence of 0.02 μs and 1.29 μs.

The PL quantum efficiency was 5.3% before the aeration with nitrogen, and 10.6% after the aeration with nitrogen.

EXAMPLE 8

A $10^{-5}$ mol/L toluene solution was prepared for the compound of Example 3 of the present invention (Compound 4), instead of the compound of Example 1 of the present invention (Compound 1) used in Example 6, and the characteristics of the toluene solution were evaluated in the same manner as in Example 6. As a result, fluorescence having a peak wavelength of 532 nm was observed.

The PL quantum efficiency was 13.3% before the aeration with nitrogen, and 19.2% after the aeration with nitrogen.

EXAMPLE 9

A $10^{-5}$ mol/L toluene solution was prepared for the compound of Example 4 of the present invention (Compound 3), instead of the compound of Example 1 of the present invention (Compound 1) used in Example 6, and the characteristics of the toluene solution were evaluated in the same manner as in Example 6. As a result, fluorescence having a peak wavelength of 584 nm was observed. The emission lifetime was observed as fluorescence of 7 ns, and delayed fluorescence of 0.2 μs.

The PL quantum efficiency was 14.8% before the aeration with nitrogen, and 17.4% after the aeration with nitrogen.

EXAMPLE 10

A 100 nm-thick thin film was fabricated as an organic PL device by performing dual vapor deposition of mCP and the compound of Example 1 (Compound 1) of the present invention on a glass substrate at a deposition rate ratio of 94:6 (mCP:the compound of Example 1 (Compound 1) of the present invention). The device had PL quantum efficiency of 39.1% as measured by an absolute PL quantum yield measurement device (Model Quantaurus-QY manufactured by Hamamatsu Photonics K.K.) under a stream of nitrogen at 300 K. The time-resolved spectrum of the organic PL device was also evaluated with a streak camera (Model C4334 manufactured by Hamamatsu Photonics K.K.) after applying 337-nm light from a $N_2$ laser. A component with an emission lifetime of 115 μs or less was determined as fluorescence, and a component with an emission lifetime of longer than 115 μs was determined as delayed fluorescence. The emission from the device was 40% fluorescence, and 60% delayed fluorescence.

EXAMPLE 11

An organic PL device was fabricated under the same conditions used in Example 6, except that mCP and the compound of Example 3 (Compound 4) of the present invention were used instead of mCP and the compound of Example 1 (Compound 1) of the present invention. The characteristics of the organic PL device were evaluated in the same manner as in Example 6. The PL quantum efficiency was 52.6%. The emission from the device was 19% fluorescence, and 81% delayed fluorescence.

EXAMPLE 12

Figure 5:
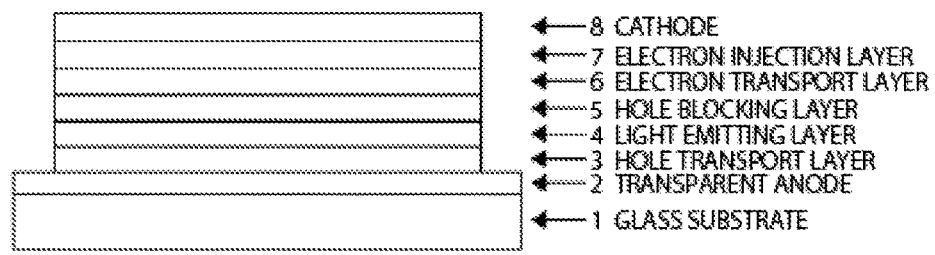
FIG. 5 is a diagram illustrating the configuration of the EL devices of Example 12 and Comparative Example 1.

An organic EL device was fabricated by vapor-depositing a hole transport layer 3, a light emitting layer 4, a hole blocking layer 5, an electron transport layer 6, an electron injection layer 7, and a cathode (aluminum electrodes) 8 in this order on a glass substrate 1 on which an ITO electrode was formed as a transparent anode 2 beforehand, as shown in FIG. 5.

Specifically, the glass substrate 1 having ITO (a thickness of 100 nm) formed thereon was washed with an organic solvent, and subjected to a UV ozone treatment to wash the surface. The glass substrate with the ITO electrode was then installed in a vacuum vapor deposition apparatus, and the pressure was reduced to 0.001 Pa or less.

This was followed by formation of the hole transport layer 3 by vapor depositing NPD over the transparent anode 2 in a thickness of 35 nm at a vapor deposition rate of 2.0 Å/sec. Then, the light emitting layer 4 was formed on the hole transport layer 3 in a thickness of 15 nm by dual vapor deposition of mCP and the compound of Example 1 of the present invention (Compound 1) at a vapor deposition rate ratio of 95:5 (mCP: compound of Example 1 of the present invention (Compound 1)). The hole blocking layer 5 was then formed on the light emitting layer 4 by forming PPT in a thickness of 10 nm at a deposition rate of 2.0 Å/sec. The electron transport layer 6 was then formed on the hole blocking layer 5 by forming TPBI in a thickness of 55 nm at a deposition rate of 2.0 Å/sec. The electron injection layer 7 was then formed on the electron transport layer 6 by forming lithium fluoride in a thickness of 0.8 nm at a deposition rate of 0.1 Å/sec. Finally, the cathode 8 was formed by vapor depositing aluminum in a thickness of 70 nm. The characteristics of the organic EL device thus fabricated were measured in the atmosphere at ordinary temperature.

The organic EL device fabricated with the compound of Example 1 of the present invention (compound 1) was measured for emission characteristics by applying DC voltage. Table 1 summarizes the measurement results.

Comparative Example 1

For comparison, an organic EL device was fabricated in the same manner as in Example 12, except that mCP and the compound of the following structural formula (Comparative Compound A) described in JP-A-2010-505241 were used as materials of the light emitting layer 4, instead of using mCP and the compound of Example 1 (Compound 1) of the present invention. The characteristics of the organic EL device were measured in the atmosphere at ordinary temperature. Table 1 summarizes the results of the emission characteristics measurements after applying DC voltage to the organic EL device.

[Chemical Formula 147]

(Comparative Compound A)

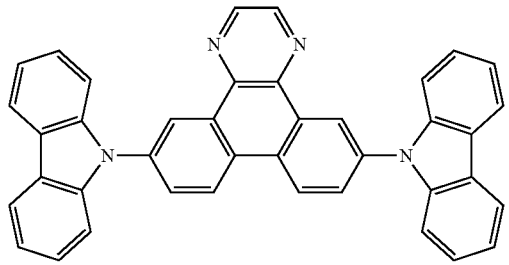

TABLE 1

|  | Compounds | Voltage [V] (@10 mA/cm$^2$) | Luminance [cd/m$^2$] (@10 mA/cm$^2$) | Current efficiency [cd/A] (@10 mA/cm$^2$) | Power efficiency [lm/W] (@10 mA/cm$^2$) |
| --- | --- | --- | --- | --- | --- |
| Ex. 12 | Compound 1 | 7.8 | 2,396 | 22.1 | 8.9 |
| Com. Ex. 1 | Comparative Compound A | 8.4 | 82 | 0.9 | 0.4 |

As shown in Table 1, the luminance upon passing current at a current density of 10 mA/cm$^2$ was much higher in the organic EL device of Example 12, which had a luminance of 2,396 cd/m$^2$, than in the organic EL device of Comparative Example 1 in which Comparative Compound A was used, and the luminance was 82 cd/m$^2$. The organic EL device of Example 12 also had a much higher luminous efficiency of 22.1 cd/A than the luminous efficiency, 0.9 cd/A, of the organic EL device of Comparative Example 1 in which Comparative Compound A was used. The power efficiency also greatly improved in the organic EL device of Example 12 with the yielded value 8.9 lm/W, far greater than the power efficiency 0.4 lm/W of the organic EL device of Comparative Example 1 using Comparative Compound A.

As demonstrated above, the organic EL devices using the compounds of the present invention were shown to be capable of achieving much higher luminous efficiency than achievable with the organic EL device using Comparative Compound A.

INDUSTRIAL APPLICABILITY

The compounds having a tetraazatriphenylene ring structure of the present invention can emit delayed fluorescence and have desirable thin-film stability, and the compounds are excellent as material of a light emitting layer, especially as a dopant material of a light emitting layer. An organic EL device produced by using the compounds can achieve much higher luminance and luminous efficiency than organic EL devices of related art.

REFERENCE SIGNS LIST

1 Glass substrate
2 Transparent anode
3 Hole transport layer
4 Light emitting layer
5 Hole blocking layer
6 Electron transport layer
7 Electron injection layer
8 Cathode

The invention claimed is:
1. An organic electroluminescent device comprising a pair of electrodes, and one or more organic layers sandwiched between the pair of electrodes, wherein
the one or more organic layers comprises a light emitting layer,
the light emitting layer comprises a compound of the following general formula (1) and a host material not represented by the following general formula (1) and does not comprise a phosphorescent light-emitting metal complex, wherein the light emitting layer comprises the compound of the general formula (1) in an amount of 5% to 6% by weight:

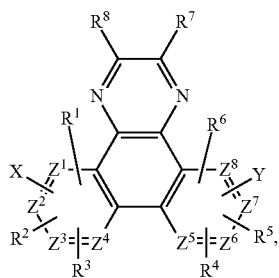

(1)

wherein X represents a substituted or unsubstituted aromatic hydrocarbon group, a substituted or unsubstituted aromatic heterocyclic group, a substituted or unsubstituted condensed polycyclic aromatic group, or a disubstituted amino group substituted with groups selected from aromatic hydrocarbon groups, aromatic heterocyclic groups, and condensed polycyclic aromatic groups, Y represents a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, $R^1$ to $R^8$ may be the same or different from each other, and represent a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, wherein $R^1$ to $R^8$ may bind to each other via a single bond, a substituted or unsubstituted methylene group, an oxygen atom, or a sulfur atom to form a ring, and $Z^1$ to $Z^8$ represent a carbon atom or a nitrogen atom, wherein at least one of $Z^1$ to $Z^4$ is a nitrogen atom, and at least one of $Z^5$ to $Z^8$ is a nitrogen atom, and in these cases the nitrogen atoms do not have the hydrogen atoms or the substituents of $R^1$ to $R^6$.

2. The organic electroluminescent device according to claim 1, wherein only one of $Z^1$ to $Z^4$ is a nitrogen atom.

3. The organic electroluminescent device according to claim 1, wherein only one of $Z^5$ to $Z^8$ is a nitrogen atom.

4. The organic electroluminescent device according to claim 1, wherein only one of $Z^1$ to $Z^4$ is a nitrogen atom and only one of $Z^5$ to $Z^8$ is a nitrogen atom.

5. The organic electroluminescent device according to claim 1, wherein the compound of the general formula (1) is a dopant of the light emitting layer.

6. The organic electroluminescent device according to claim 1, wherein the compound of the general formula (1) emits light.

7. The organic electroluminescent device according to claim 1, which emits delayed fluorescence.

8. The organic electroluminescent device according to claim 1, wherein the compound of the general formula (1) emits delayed fluorescence.

9. The organic electroluminescent device according to claim 1, wherein the compound is represented by the following general formula (1a):

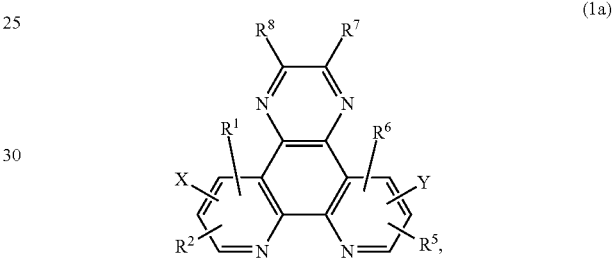

(1a)

wherein X represents a substituted or unsubstituted aromatic hydrocarbon group, a substituted or unsubstituted aromatic heterocyclic group, a substituted or unsubstituted condensed polycyclic aromatic group, or a disubstituted amino group substituted with groups selected from aromatic hydrocarbon groups, aromatic heterocyclic groups, and condensed polycyclic aromatic groups, Y represents a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, and $R^1$ to $R^2$, and $R^5$ to $R^8$ may be the same or different from each other, and represent a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, wherein $R^1$ to $R^2$, and $R^5$ to $R^8$ may bind to each other via a single bond, a substituted or unsubstituted methylene group, an oxygen atom, or a sulfur atom to form a ring.

10. The organic electroluminescent device according to claim 1, wherein the compound is represented by the following general formula (1a-1):

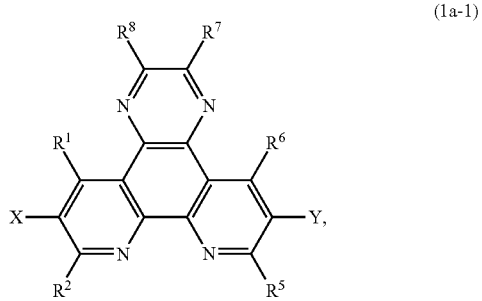

(1a-1)

wherein X represents a substituted or unsubstituted aromatic hydrocarbon group, a substituted or unsubstituted aromatic heterocyclic group, a substituted or unsubstituted condensed polycyclic aromatic group, or a disubstituted amino group substituted with groups selected from aromatic hydrocarbon groups, aromatic heterocyclic groups, and condensed polycyclic aromatic groups, Y represents a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, and $R^1$ to $R^2$, and $R^5$ to $R^8$ may be the same or different from each other, and represent a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, wherein $R^1$ to $R^2$, and $R^5$ to $R^8$ may bind to each other via a single bond, a substituted or unsubstituted methylene group, an oxygen atom, or a sulfur atom to form a ring.

11. The organic electroluminescent device according to claim 1, wherein the compound is represented by the following general formula (1a-2):

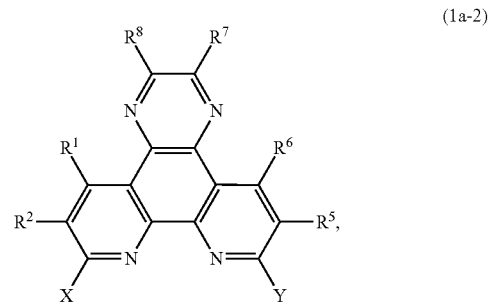

(1a-2)

wherein X represents a substituted or unsubstituted aromatic hydrocarbon group, a substituted or unsubstituted aromatic heterocyclic group, a substituted or unsubstituted condensed polycyclic aromatic group, or a disubstituted amino group substituted with groups selected from aromatic hydrocarbon groups, aromatic heterocyclic groups, and condensed polycyclic aromatic groups, Y represents a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, and $R^1$ to $R^2$, and $R^5$ to $R^8$ may be the same or different from each other, and represent a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, wherein $R^1$ to $R^2$, and $R^5$ to $R^8$ may bind to each other via a single bond, a substituted or unsubstituted methylene group, an oxygen atom, or a sulfur atom to form a ring.

12. The organic electroluminescent device according to claim 1, wherein the compound is represented by the following general formula (1a-3):

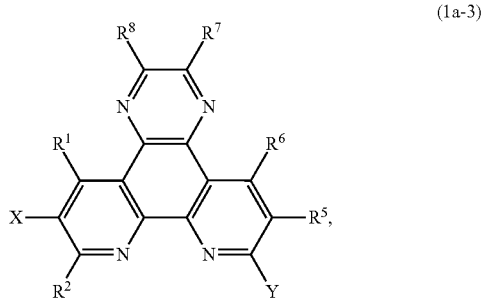

(1a-3)

wherein X represents a substituted or unsubstituted aromatic hydrocarbon group, a substituted or unsubstituted aromatic heterocyclic group, a substituted or unsubstituted condensed polycyclic aromatic group, or a disubstituted amino group substituted with groups selected from aromatic hydrocarbon groups, aromatic heterocyclic groups, and condensed polycyclic aromatic groups, Y represents a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, and $R^1$ to $R^2$, and $R^5$ to $R^8$ may be the same or different from each other, and represent a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, wherein $R^1$ to $R^2$, and $R^5$ to $R^8$ may bind to each other via a single bond, a substituted or unsubstituted methylene group, an oxygen atom, or a sulfur atom to form a ring.

13. The organic electroluminescent device according to claim 1, wherein the compound is represented by the following general formula (1a-4):

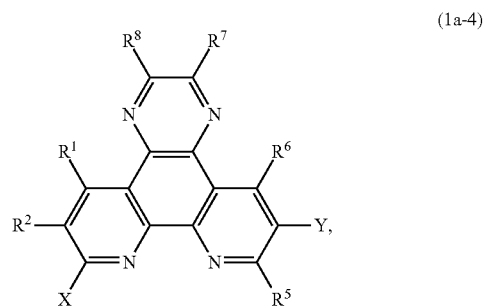

(1a-4)

wherein X represents a substituted or unsubstituted aromatic hydrocarbon group, a substituted or unsubstituted aromatic heterocyclic group, a substituted or unsubstituted condensed polycyclic aromatic group, or a disubstituted amino group substituted with groups selected from aromatic hydrocarbon groups, aromatic heterocyclic groups, and condensed polycyclic aromatic groups, Y represents a hydrogen atom, a deuterium atom, a fluorine atom, a chlorine atom, a cyano group, a nitro group, a linear or branched alkyl group of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, and $R^1$ to $R^2$, and $R^5$ to $R^8$ may be the same or different from each other, and represent a hydrogen atom, a deuterium atom, a fluorine atom, a chlorine atom, a cyano group, a nitro group, a linear or branched alkyl of 1 to 6 carbon atoms that may have a substituent, a cycloalkyl group of 5 to 10 carbon atoms that may have a substituent, a linear or branched alkenyl group of 2 to 6 carbon atoms that may have a substituent, a linear or branched alkyloxy group of 1 to 6 carbon atoms that may have a substituent, a cycloalkyloxy group of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with groups selected from aromatic hydrocarbon groups, aromatic heterocyclic groups, and condensed polycyclic aromatic groups, wherein $R^1$ to $R^2$, and $R^5$ to $R^8$ may bind to each other via a single bond, a substituted or unsubstituted methylene group, an oxygen atom, or a sulfur atom to form a ring.

14. The organic electroluminescent device according to claim 1, wherein X and Y in the general formula (1) may be the same or different, and represent a group selected from substituted or unsubstituted carbazolyl groups, substituted or unsubstituted phenoxazinyl groups, substituted or unsubstituted phenothiazinyl groups, substituted or unsubstituted acridinyl groups, substituted or unsubstituted phenazinyl groups, and disubstituted amino groups substituted with aromatic hydrocarbon groups or condensed polycyclic aromatic groups.

* * * * *